(12) United States Patent
Jeanmart et al.

(10) Patent No.: US 8,956,999 B2
(45) Date of Patent: Feb. 17, 2015

(54) HERBICIDES

(75) Inventors: Stephane André Marie Jeanmart, Stein (CH); Christopher John Mathews, Bracknell (GB); John Benjamin Taylor, Bracknell (GB); Mangala Govenkar, Ilhas Goa (IN); Stephen Christopher Smith, Bracknell (GB)

(73) Assignees: Syngenta Limited, Guildford, Surrey (GB); Syngenta Crop Protection LLC, Greensboro, NC (US)

( * ) Notice: Subject to any disclaimer, the term of this patent is extended or adjusted under 35 U.S.C. 154(b) by 651 days.

(21) Appl. No.: 12/666,405

(22) PCT Filed: Jun. 26, 2008

(86) PCT No.: PCT/EP2008/005197
§ 371 (c)(1),
(2), (4) Date: Jun. 18, 2010

(87) PCT Pub. No.: WO2009/000533
PCT Pub. Date: Dec. 31, 2008

(65) Prior Publication Data
US 2010/0279868 A1 Nov. 4, 2010

(30) Foreign Application Priority Data
Jun. 28, 2007 (GB) .................................. 0712653.5

(51) Int. Cl.
| | |
|---|---|
| *A01N 43/16* | (2006.01) |
| *C07D 311/00* | (2006.01) |
| *C07D 263/32* | (2006.01) |
| *C07D 277/24* | (2006.01) |
| *C07D 293/06* | (2006.01) |
| *C07D 333/22* | (2006.01) |
| *C07D 403/04* | (2006.01) |
| *C07D 409/04* | (2006.01) |
| *C07D 417/04* | (2006.01) |
| *C07D 421/04* | (2006.01) |
| *C07D 493/08* | (2006.01) |
| *C07D 493/20* | (2006.01) |

(52) U.S. Cl.
CPC .......... *C07D 263/32* (2013.01); *C07D 277/24* (2013.01); *C07D 293/06* (2013.01); *C07D 333/22* (2013.01); *C07D 403/04* (2013.01); *C07D 409/04* (2013.01); *C07D 417/04* (2013.01); *C07D 421/04* (2013.01); *C07D 493/08* (2013.01); *C07D 493/20* (2013.01)
USPC .......... 504/209; 504/292; 549/396; 549/414; 549/417; 549/423

(58) Field of Classification Search
USPC .......... 504/209, 292; 549/396, 414, 417, 423
See application file for complete search history.

(56) References Cited

U.S. PATENT DOCUMENTS

| | | | |
|---|---|---|---|
| 4,175,135 A | 11/1979 | Haines et al. | |
| 4,209,532 A | 6/1980 | Wheeler et al. | |
| 4,338,122 A | 7/1982 | Wheeler | |
| 4,409,153 A | 10/1983 | Hodakowski et al. | |
| 4,489,012 A | 12/1984 | Hodakowski | |
| 4,526,723 A | 7/1985 | Wheeler et al. | |
| 4,659,372 A | 4/1987 | Wheeler et al. | |
| 4,678,501 A | 7/1987 | Manning et al. | |
| 5,840,661 A | 11/1998 | Fischer et al. | |
| 6,458,965 B1 | 10/2002 | Lieb et al. | |
| 6,894,005 B1 | 5/2005 | Maetzke et al. | |
| 8,058,210 B2 | 11/2011 | Lieb et al. | |
| 8,084,649 B2 | 12/2011 | Muehlebach et al. | |
| 2003/0216260 A1 | 11/2003 | Ruther et al. | |
| 2005/0164883 A1 | 7/2005 | Maetzke et al. | |
| 2006/0166829 A1 | 7/2006 | Fischer et al. | |
| 2010/0113270 A1 | 5/2010 | Mathews et al. | |
| 2010/0210466 A1 | 8/2010 | Muehlebach et al. | |
| 2012/0040826 A1 | 2/2012 | Jeanmart et al. | |

FOREIGN PATENT DOCUMENTS

| | | |
|---|---|---|
| CA | 2322158 | 8/2000 |
| CA | 2325526 | 9/2000 |

(Continued)

OTHER PUBLICATIONS

M. Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.
J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.
J. Wenger, T. Niderrmann and C. Mathews, "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

*Primary Examiner* — Noble Jarrell
*Assistant Examiner* — Valerie Rodriguez-Garcia
(74) *Attorney, Agent, or Firm* — R. Kody Jones

(57) ABSTRACT

Pyrandione, thiopyrandione and cyclohexanetrione compounds of formula (I), which are suitable for use as herbicides.

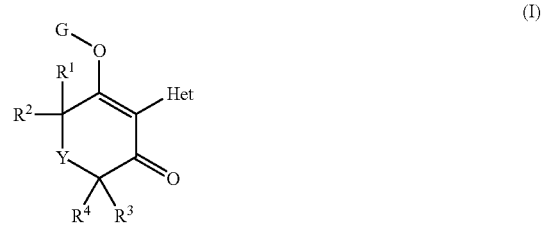

25 Claims, No Drawings

(56) References Cited

FOREIGN PATENT DOCUMENTS

| | | |
|---|---|---|
| CA | 2382432 | 2/2002 |
| CA | 2382435 | 2/2002 |
| CA | 2456776 | 2/2004 |
| DE | 2813341 | 4/1983 |
| WO | 96/01798 | 1/1996 |
| WO | 96/16061 | 5/1996 |
| WO | 99/43646 | 9/1999 |
| WO | 99/48869 | 9/1999 |
| WO | 1999/47525 | 9/1999 |
| WO | 00/47585 | 8/2000 |
| WO | 01/17972 | 3/2001 |
| WO | 2001/17973 | 3/2001 |
| WO | 01/74770 | 10/2001 |
| WO | 0174770 | 10/2001 |
| WO | 02/088098 | 11/2002 |
| WO | 03/013249 | 2/2003 |
| WO | 03/035643 | 5/2003 |
| WO | 2004/37749 | 5/2004 |
| WO | 2004037749 | 5/2004 |
| WO | 04/111042 | 12/2004 |
| WO | 2006/034446 | 3/2006 |
| WO | 2006034315 | 3/2006 |
| WO | 2008/71405 | 6/2008 |
| WO | 2008071405 | 6/2008 |
| WO | 2009/015877 | 7/2008 |
| WO | 2008/145336 | 8/2008 |
| WO | 2008/110307 | 9/2008 |
| WO | 2008/110308 | 9/2008 |
| WO | 2009/030450 | 9/2008 |
| WO | 2009/074314 | 6/2009 |
| WO | 2009/086041 | 9/2009 |

HERBICIDES

This application is a 371 of International Application No. PCT/EP2008/005197 filed Jun. 26, 2008, which claims priority to GB 0712653.5 filed Jun. 28, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants such as rice, corn, cereals, cotton, soya, sugarbeet, oilseed rape or canola, sugar cane, or in inhibiting plant growth.

Cyclic diones having herbicidal action are described, for example, in WO 01/74770.

Novel pyrandione, thiopyrandione and cyclohexanetrione compounds having herbicidal and growth-inhibiting properties have now been found.

The present invention accordingly relates to compounds of formula I

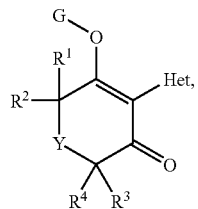

(I)

wherein
$R^1$, $R^2$, $R^3$ and $R^4$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$ haloalkyl or halogen; cyclobutyl or cyclobutyl substituted by $C_1$- or $C_2$ alkyl; oxetanyl or oxetanyl substituted by $C_1$- or $C_2$ alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$ alkyl; oxetanyl$C_1$-$C_5$alkyl or oxetanyl$C_1$-$C_5$alkyl substituted by $C_1$- or $C_2$alkyl; $C_5$-$C_7$cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$ alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$ alkoxy, $C_1$-$C_4$haloalkyl, halogen, nitro, cyano, $C_1$-$C_4$ alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or $R^1$ and $R^2$, or $R^3$ and $R^4$, are joined to form a 3-7 membered saturated ring in which a methylene group is optionally replaced by an oxygen or sulfur atom, and which may be optionally substituted by $C_1$- or $C_2$-alkyl, halogen or $C_1$-$C_2$ alkoxy, or a 5-7 membered unsaturated ring in which a methylene group is optionally replaced by an oxygen or sulfur atom, and which may be optionally substituted by $C_1$- or $C_2$-alkyl, halogen or $C_1$-$C_2$ alkoxy; or $R^1$ and $R^3$ are joined to form a 5-7 membered saturated or unsaturated ring or a 5-7 membered saturated or unsaturated ring optionally substituted by $C_1$- or $C_2$alkyl, $C_1$- or $C_2$alkoxy, hydroxy or halogen;

Y is O, C=O, $S(O)_m$ or $S(O)_nNR^5$; provided that when Y is C=O, $R^3$ and $R^4$ are different from hydrogen when either $R^1$ or $R^2$ is hydrogen, and $R^1$ and $R^2$ are different from hydrogen when either $R^3$ or $R^4$ is hydrogen; m is 0 or 1 or 2 and n is 0 or 1;

$R^5$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by $R^6$; benzylcarbonyl or benzylcarbonyl substituted by $R^6$; pyridylcarbonyl or pyridylcarbonyl substituted by $R^6$; phenoxycarbonyl or phenoxycarbonyl substituted by $R^6$; benzyloxycarbonyl or benzyloxycarbonyl substituted by $R^6$;

$R^6$ is $C_1$-$C_6$haloalkyl, $C_1$-$C_6$alkoxycarbonyl, nitro, cyano, formyl, carboxyl or halogen;

Het is a an optionally substituted monocyclic or bicyclic heteroaromatic ring; and G is hydrogen, an alkali metal, alkaline earth metal, sulfonium, ammonium or a latentiating group.

In the substituent definitions of the compounds of the formula I, the alkyl substituents and alkyl moieties of alkoxy, alkylamino etc. having 1 to 6 carbon atoms are preferably methyl, ethyl, propyl, butyl, pentyl and hexyl, in the form of their straight and branched isomers. The alkenyl and alkynyl radicals having 2 to 6 carbon atoms as well as up to 10 carbon atoms can be straight or branched and can contain more than 1 double or triple bond. Examples are vinyl, allyl, propargyl, butenyl, butynyl, pentenyl and pentynyl. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Heterocycles, as a rule, correspond to the carbocycles or cycloalkyl radicals mentioned above with the exception that one or two methylene groups are replaced by an oxygen, sulphur or nitrogen atom, which can be substituted further. Preferred halogens are fluorine, chlorine and bromine. Preferred examples of heteroaryls $R^1$, $R^2$, $R^3$, $R^4$, $R^8$ and $R^{12}$ are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl and pyridazinyl, and, where appropriate, N-oxides and salts thereof. These heteroaryls can be substituted by one or more substituents, where preferred substituents are, for example, halogen, $C_1$-$C_4$ alkyl, $C_3$-$C_6$ cycloalkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, poly$C_1$-$C_4$ alkox$C_1$-$C_4$ yalkyl, $C_1$-$C_4$ alkylthio$C_1$-$C_4$ alkyl, nitro, cyano, $C_2$-$C_4$alkenyl, $C_2$-$C_4$ haloalkenyl, $C_2$-$C_4$ alkynyl, aryl, aryl substituted by $C_1$-$C_2$-alkyl, $C_1$-$C_2$-alkoxy, $C_1$-$C_2$ haloalkyl, $C_1$-$C_2$ haloalkoxy, cyano or nitro, or heteroaryl or heteroaryl substituted by $C_1$-$C_2$-alkyl, $C_1$-$C_2$-alkoxy, $C_1$-$C_2$ haloalkyl, $C_1$-$C_2$ haloalkoxy, cyano or nitro.

The group G denotes hydrogen, an alkali metal cation, alkaline earth metal cation, sulfonium cation (preferably —S($C_1$-$C_6$alkyl$_3$)$^+$) or ammonium cation (preferably —NH$_4^+$ or —N($C_1$-$C_6$alkyl)$_4^+$), or a latentiating group. These latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. The latentiating group G is preferably selected from the groups G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^c$)—$R^d$, —SO$_2$—$R^e$, —P($X^e$)($R^f$)—$R^g$ or CH$_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, amino, $C_1$-$C_3$alkylamino, $C_1$-$C_3$dialkylamino, $C_1$-$C_3$alkoxy or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S and optionally substituted by 1 or 2 $C_1$-$C_3$alkyl groups.

$R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, nitro, amino, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, amino, hydroxyl, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

Preferably, G denotes $C(X^a)$—$R^a$ or $C(X^b)$—$X^c$—$R^b$, and the meanings of $X^a$, $R^a$, $X^b$, $X^c$ and $R^b$ are as defined above. More important groups G comprise hydrogen, an alkali metal or alkaline earth metal, where hydrogen is particularly preferred.

In a preferred group of compounds of the formula I, $R^1$, $R^2$, $R^3$ and $R^4$, independently of each other, are hydrogen, $C_1$-$C_4$ alkyl, in particular hydrogen, methyl or ethyl, and most preferably methyl.

In another preferred group of compounds of the formula I, $R^1$ and $R^3$ are joined to form a 5-7 membered saturated or unsaturated ring or a 5-7 membered saturated or unsaturated ring substituted by $C_1$- or $C_2$alkyl, $C_1$- or $C_2$alkoxy or halogen and wherein $R^2$ and $R^4$, independently of each other, are hydrogen, methyl or ethyl.

Preferred meanings of Y are O, C=O and S.

Het is preferably an optionally substituted monocyclic 5- or 6-membered nitrogen or sulfur containing heteroaryl.

More preferably, Het is a group of the formula $R_1$ to $R_{12}$

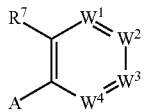
($R_1$)

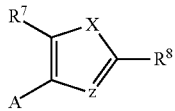
($R_2$)

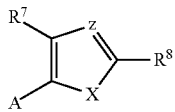
($R_3$)

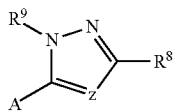
($R_4$)

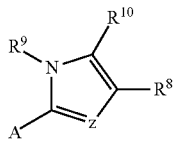
($R_5$)

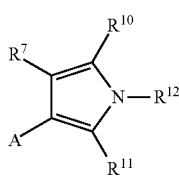
($R_6$)

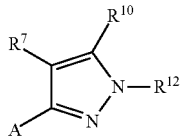
($R_7$)

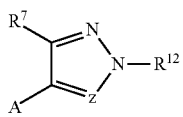
($R_8$)

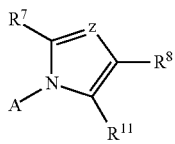
($R_9$)

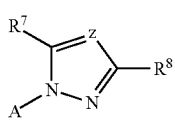
($R_{10}$)

-continued

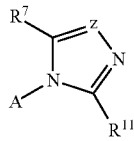
($R_{11}$)

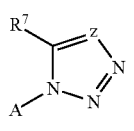
($R_{12}$)

wherein A designates the point of attachment to the ketoenol moiety, and $W^1$ is N or $CR^{10}$;
$W^2$ and $W^3$ are independently of each other N or $CR^8$;
$W^4$ is N or $CR^{11}$;
with the proviso that at least one of $W^1$, $W^2$, $W^3$ or $W^4$ is N;
X is O, S, Se, or $NR^{13}$;
Z is N or $CR^{14}$;
$R^7$ is halogen, $C_1$-$C_4$ alkyl, $C_3$-$C_6$ cycloalkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, nitro or cyano;
$R^8$ is hydrogen, halogen, cyano, nitro, $C_1$-$C_4$ alkyl, $C_2$-$C_4$ alkenyl, $C_1$-$C_4$ alkoxy, $C_2$-$C_4$ alkenyloxy, $C_1$-$C_4$ alkylthio, $C_1$-$C_4$ alkylsulphinyl, $C_1$-$C_4$ alkylsulphonyl, $C_1$-$C_4$ alkoxy $C_1$-$C_4$ alkyl, poly $C_1$-$C_4$ alkoxy$C_1$-$C_4$ alkyl, $C_1$-$C_4$ alkylthio $C_1$-$C_4$ alkyl, each of which is unsubstituted or substituted by halogen, $C_3$-$C_8$cycloalkyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl, pyridazinyl, quinolinyl, isoquinolinyl, cinnolinyl, quinazolinyl and quinoxalinyl, N-oxides and salts thereof, each of these substituents being unsubstituted or substituted by halogen, $C_1$-$C_4$ alkyl, halo$C_1$-$C_4$ alkyl, $C_1$-$C_4$ alkoxy, $C_2$-$C_4$ alkenyloxy, $C_1$-$C_4$ alkylthio, $C_1$-$C_4$ alkylsulphinyl, $C_1$-$C_4$ alkyl-sulphonyl, halo$C_1$-$C_4$ alkyl, halo$C_1$-$C_4$ alkoxy, cyano or nitro;
$R^9$ is hydrogen, $C_1$-$C_4$ alkyl, $C_2$-$C_3$alkenyl, $C_2$-$C_3$alkynyl, $C_1$-$C_4$ haloalkyl or $C_2$-$C_3$ haloalkenyl;
$R^{10}$ is hydrogen, methyl, halomethyl or halogen;
$R^{11}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano;
$R^{12}$ is hydrogen, methyl, ethyl, halomethyl, haloethyl, aryl, aryl substituted by $C_1$-$C_2$-alkyl, $C_1$-$C_2$-alkoxy, $C_1$-$C_2$ haloalkyl, $C_1$-$C_2$ haloalkoxy, cyano or nitro, heteroaryl or heteroaryl substituted by $C_1$-$C_2$-alkyl, $C_1$-$C_2$-alkoxy, $C_1$-$C_2$ haloalkyl, $C_1$-$C_2$ haloalkoxy, cyano or nitro;
$R^{13}$ is hydrogen, methyl or halomethyl; and
$R^{14}$ is hydrogen, methyl, ethyl, halomethyl, haloethyl, halogen, cyano or nitro.

In particular, Het is a group of the formula $R_2$, wherein X is sulfur, $R^8$ is thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl, pyridazinyl, quinolinyl, isoquinolinyl, cinnolinyl, quinazolinyl and quinoxalinyl, N-oxides and salts thereof, each of which is optionally substituted one to three times by halogen, $C_1$-$C_2$-alkyl, $C_1$-$C_2$-alkoxy, $C_1$-$C_2$ haloalkyl, $C_1$-$C_2$ haloalkoxy, cyano or nitro, especially halogen and Z is nitrogen or C—H.

Especially, Het is a group of the formula R₂, wherein X is sulfur, $R^7$ is methyl or ethyl, $R^8$ is phenyl, phenyl substituted one to three times by halogen, $C_1$-$C_2$-alkyl, $C_1$-$C_2$-alkoxy, $C_1$-$C_2$ haloalkyl, $C_1$-$C_2$ haloalkoxy, cyano or nitro, and Z is nitrogen or C—H.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octyl-amine, nonylamine, decylamine, pentadecylamine, hexadecylamine, heptadecylamine, octadecylamine, methylethylamine, methylisopropylamine, methylhexylamine, methyl-nonylamine, methylpentadecylamine, methyloctadecylamine, ethylbutylamine, ethylheptyl-amine, ethyloctylamine, hexylheptylamine, hexyloctylamine, dimethylamine, diethylamine, di-n-propylamine, diisopropylamine, di-n-butylamine, di-n-amylamine, diisoamylamine, dihexyl-amine, diheptylamine, dioctylamine, ethanolamine, n-propanolamine, isopropanolamine, N,N-diethanolamine, N-ethylpropanolamine, N-butylethanolamine, allylamine, n-but-2-enyl-amine, n-pent-2-enylamine, 2,3-dimethylbut-2-enylamine, dibut-2-enylamine, n-hex-2-enyl-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylene-diamines, benzidines, naphthylamines and o-, m- and p-chloroanilines; but especially triethyl-amine, isopropylamine and diisopropylamine.

Preferred quaternary ammonium bases suitable for salt formation correspond, for example, to the formula $[N(R_a R_b R_b R_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the formula I.

A compound of formula I wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula I wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl $(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base. Where substituents $R^1$ and $R^2$ are not equal to substituents $R^3$ and $R^4$, these reactions may produce, in addition to a compound of formula I, a second compound of formula IA. This invention covers both a compound of formula I and a compound of formula IA, together with mixtures of these compounds in any ratio.

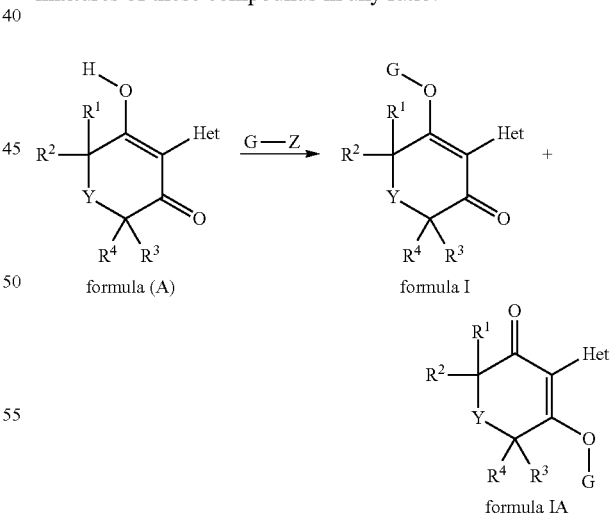

The O-alkylation of cyclic 1,3-diones is known; suitable methods are described, for example, in U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-

1582; S. Chandra Roy et al., Chem. Letters, (2006), 35 (1), 16-17; P. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N' carbodiimidazole, and a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

Compounds of formula (A), wherein Y is $S(O)_m$ and m is 1 or 2 may be prepared from compounds of formula (A) wherein Y is S by oxidation, according to the procedure of E. Fehnel and A. Paul, J. Am. Chem. Soc., (1955), 77, 4241.

Compounds of formula (A), wherein Y is O, S or C=O may be prepared via the cyclisation of compounds of formula (B), preferably in the presence of an acid or base, and optionally in the presence of a suitable solvent, by analogous methods to those described by T. Teresawa and T. Okada, J. Org. Chem., (1977), 42 (7), 1163-1167 and by T. Wheeler, U.S. Pat. No. 4,209,532. The compounds of the formula (B) have been particularly designed as intermediates in the synthesis of the compounds of the formula I. Compounds of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

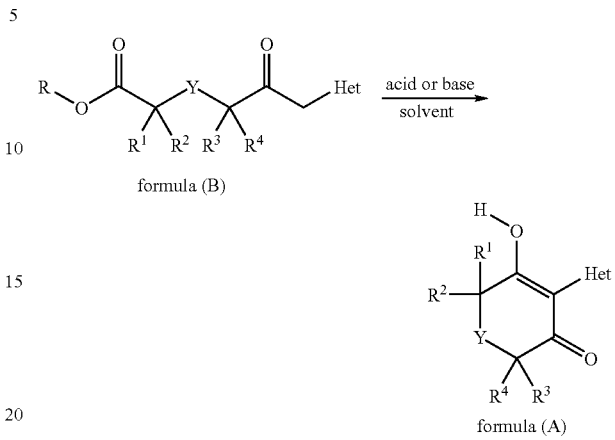

Compounds of formula (B) wherein R is alkyl (preferably methyl or ethyl) may be cyclised under acidic or, preferably basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

The compounds of the formula B are novel and have been designed particularly for the synthesis of the inventive compounds of the formula I. Compounds of formula (B), wherein R is H may be prepared by saponification of compounds of formula (C) wherein $R^1$ is alkyl (preferably methyl or ethyl) under standard conditions, followed by acidification of the reaction mixture to effect decarboxylation, by similar processes to those described, for example, by T. Wheeler, U.S. Pat. No. 4,209,532:

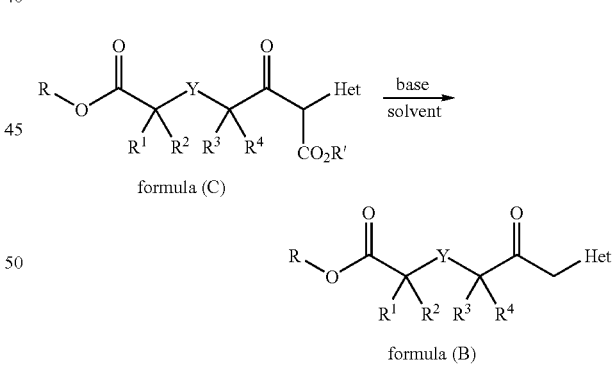

Compounds of formula (C), wherein R is H may be esterified to compounds of formula (C), wherein R is alkyl, under standard conditions.

Compounds of formula (C) wherein R is alkyl may be prepared by treating compounds of formula (D) with suitable carboxylic acid chlorides of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

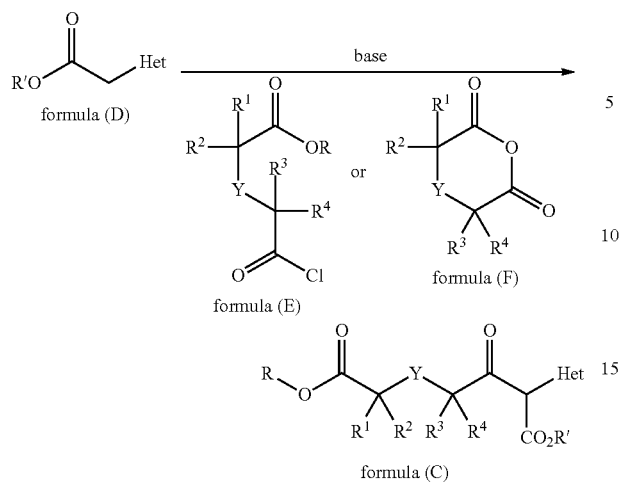

formula (D), formula (E), formula (F), formula (C)

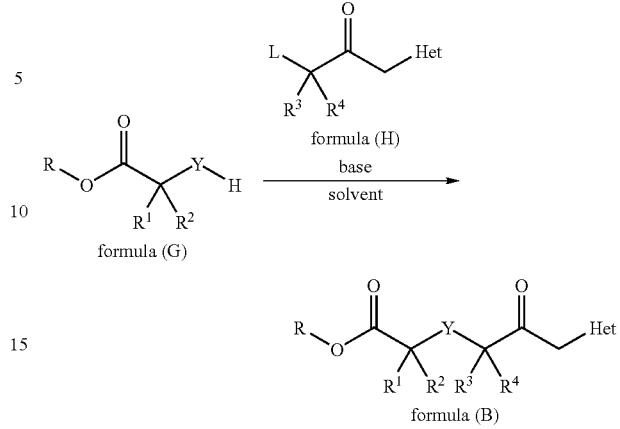

formula (G), formula (H), formula (B)

Alternatively, compounds of formula (C), wherein R is H, may be prepared by treating compounds of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F).

Compounds of formula (E) and formula (F) are known (see, for example T. Terasawa and T. Okada, J. Org. Chem., 1977, 42 (7), 1163) or may be made by similar methods from commercially available starting materials. Compounds of formula (D) are known, or may be made by known methods from known compounds (see, for example, E. Bellur and P. Langer, Synthesis (2006), 3, 480-488; E. Bellur and P. Langer, Eur. J. Org. Chem., (2005), 10, 2074-2090; G. Bartolo et al., J. Org. Chem., (1999), 64 (21), 7693-7699; R. Kranich et al., J. Med. Chem., (2007), 50 (6), 1101-1115; I. Freifeld et al., J. Org. Chem., (2006) 71 (13), 4965-4968; S. Hermann et al., WO2006/087120; R. Fischer et al. WO96/16061; H. Staab and G. Schwalbach, Justus Liebigs Annalen der Chemie, (1968), 715, 128-34; J-L Brayer et al., EP402246; P. Chemla et al., WO99/32464; A. Dornow and G. Petsch, Chem. Berichte, (1953), 86, 1404-1407; E. Y-H Chao et al., WO2001/000603; D. B. Lowe et al., WO2003/011842; R. Fischer et al., WO2001/096333; J. Ackermann et al., WO2005/049572; B. Li et al., Bioorg. Med. Chem. Lett., (2002), 12, 2141-2144, G. P. Rizzi, J. Org. Chem., (1968), 33 (4) 13333-13337; M. Okitsu and K. Yoshid, JP63230670; F. Bohlmann et al., Chem. Ber., (1955), 88, 1831-1838; R. Fischer et al., WO2003/035463; R. Fischer er al., WO2005/005428; D O'Mant, GB1226981).

Alternatively, a compound of formula (B), wherein Y is O or S, may be prepared from a known compound of formula (G), wherein Y is O or S, by alkylation with a compound of formula (H), wherein L is a leaving group such as a halogen or an alkyl-sulfonate or an aryl-sulfonate and preferably one or both of $R^3$ and $R^4$ is hydrogen. Preferably the reaction is conducted in the presence of a suitable base and optionally in the presence of a suitable solvent.

The base may be an inorganic base such as an alkali metal hydroxide, carbonate, or a metal hydride, or an organic base such as a tertiary amine or an alkali metal alkoxide. Examples of suitable inorganic bases include sodium carbonate, potassium carbonate, lithium hydroxide, sodium hydroxide, potassium hydroxide or sodium hydride, and suitable organic bases include amines such as trimethylamine or triethylamine, piperidine, pyridine and 4-diazobicyclo[2.2.2]octane. Where employed, solvents for this reaction are selected to be compatible with the reagents and include, for example, ethers such as diethyl ether, 1,2-dimethoxyethane and tetrahydrofuran, aliphatic ketones such as methyl isobutylketone and acetone, aliphatic alcohols such as methanol, ethanol and isopropanol, amides such as N,N-dimethylformamide, N,N-dimethylacetamide, and N-methylpyrrolidone, aromatic hydrocarbons such as toluene and xylene, acetonitrile and halogenated solvents such as dichloromethane and chloroform. Certain bases, such as pyridine and triethylamine, may be employed successfully as both base and solvent.

Compounds of formula (H) are known compounds or may be made my known methods from known compounds (see, for example, N. Kaila et al., J. Med. Chem. (2007), 50 (1), 40-64).

Alternatively, a compound of formula (B) wherein Y is O or S and preferably one or both of $R^1$ and $R^2$ is hydrogen may be prepared from a compound of formula (J) by reaction with a known compound of formula (K) under conditions similar to those used to prepare a compound of formula (B) from a compound of formula (G).

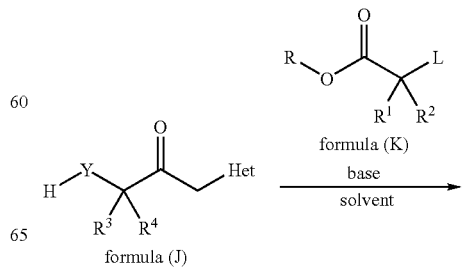

formula (J), formula (K)

-continued

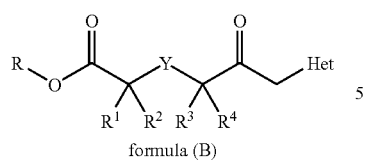
formula (B)

Compounds of formula (J) are known compounds, or may be made from known compounds by known methods. (see, for example, N. Kaila et al., J. Med. Chem. (2007), 50 (1), 40-64; E. Reimann, EP647640; V. Dalla and J. Catteau, Tetrahedron, (1999), 55, 6497-6510)).

In a further approach to compounds of formula (B), a compound of formula (B) wherein Y is O or S and $R^2$ is hydrogen may be prepared from a compound of formula (L) and a known diazoester of formula (M) by a photochemical or metal catalysed O—H and S—H insertion, by procedures described by, for example by D. Miller and C. Moody, Tetrahedron, (1995), 51, 10811-10843.

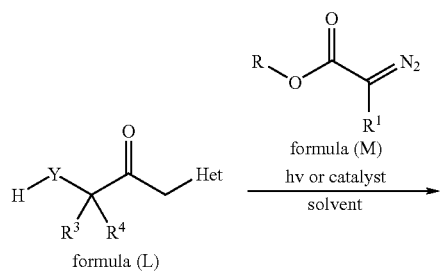

Preferably the metal catalyst is a transition metal catalyst, more preferably a rhodium (II) catalyst such as rhodium (II) acetate, or a copper catalyst such as copper (II) trifluoromethanesulfonate or copper (II) acetylacetonate, and the reaction is preferably carried out in a solvent such as dichloromethane or toluene.

Using similar methods, a compound of formula (B) wherein Y is O or S and $R^4$ is hydrogen may also be prepared by reacting a diazoketone of formula (N) with a known compound of formula (O), preferably in the presence of a suitable catalyst and in a suitable solvent under conditions outlined above.

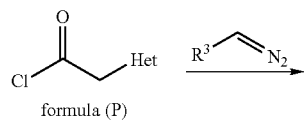

-continued

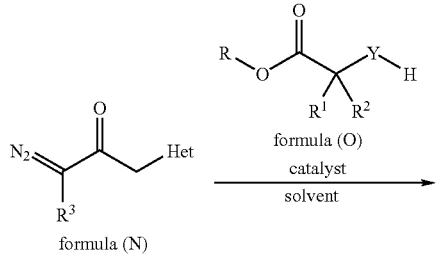

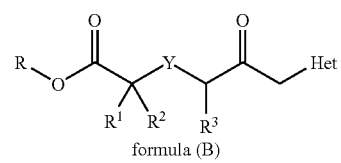
formula (B)

Compounds of formula (N) are known compounds or may be prepared by known methods (for example by reaction of a known acid chloride of formula (P) with a diazoalkane under conditions described in the literature (see, for example, A. Boularot et al., J. Med. Chem., (2007, 50 (1), 10-20; M. Salim and A. Capretta, Tetrahedron (2000); 56, 8063-8069; K Yong et al., J. Org. Chem., (1998); 63 (26), 9828-9833; A. Padwa et al., J. Org. Chem., (1989), 54 (2), 299-308)

In a further approach to compounds of formula (A), a compound of formula (O), which is a compound of formula (A) wherein Het is ($R_2$) when $R^7$ is $CH_2R''$ and $R''$ is hydrogen, alkyl or halogenoalkyl (preferably hydrogen, methyl or trifluoromethyl), may be prepared by rearrangement of a compound of formula (R), optionally in the presence of a suitable solvent and optionally under microwave irradiation.

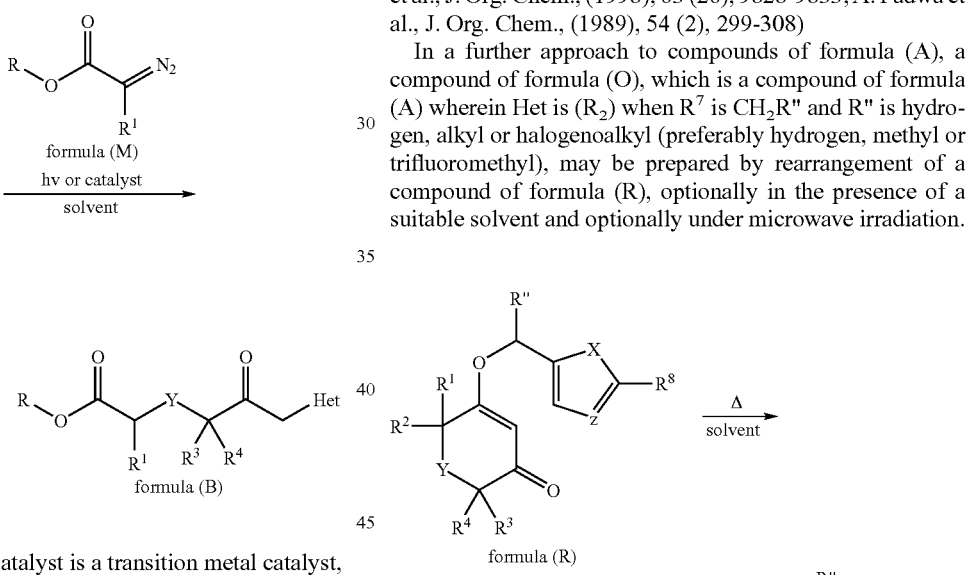

Preferably, the rearrangement is effected by heating a compound of formula (G) at temperatures of between 120-300° C., optionally in a suitable solvent such as 1,2-dimethoxyethane, diethylene glycol methyl ether, xylene, mesitylene or Dowtherm®, and optionally under microwave irradiation.

Similarly, a compound of formula (S), which is a compound of formula (A) wherein Het is ($R_3$) when $R^7$ is $CH_2R''$ and $R''$ is hydrogen, alkyl or halogenoalkyl (preferably hydrogen, methyl or trifluoromethyl), may be prepared from a compound of formula (T) using similar methods.

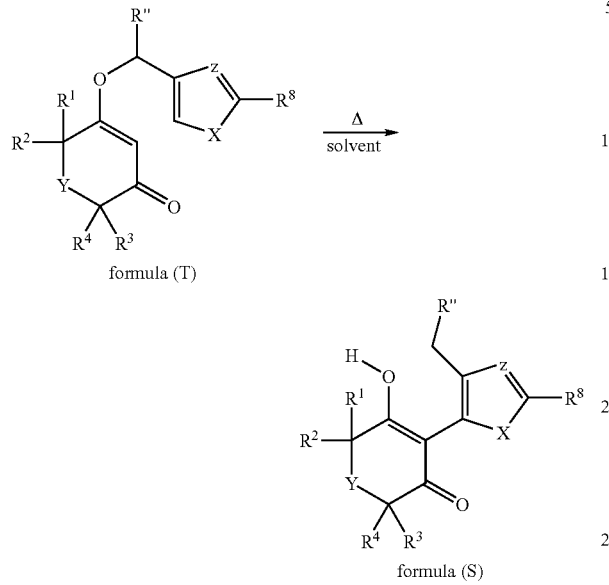

formula (T)

formula (S)

A compound of formula (R) may be prepared from a compound of formula (U) by alkylation with a compound of formula (V), wherein L is a suitable leaving group such as a halogen or an alkyl- or aryl-sulfonate, optionally in the presence of a suitable base and optionally in a suitable solvent as described above for the alkylation of compounds of formula (A)

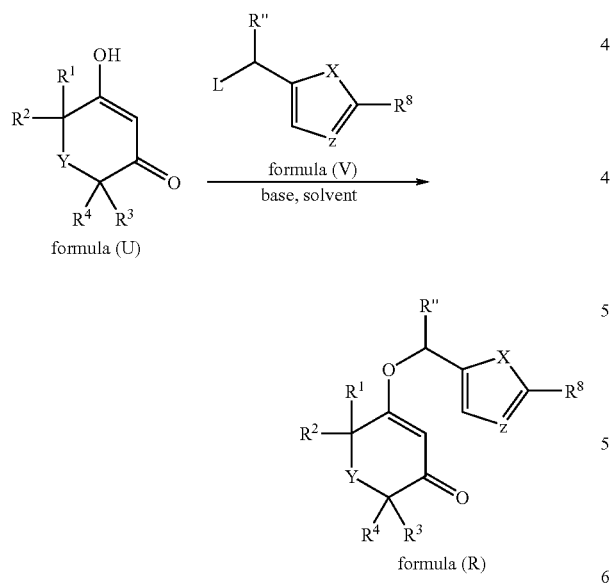

formula (U)

formula (R)

Similarly, a compound of formula (T) may be prepared from a compound of formula (U) by alkylation with a compound of formula (W), wherein L is a suitable leaving group such as a halogen or an alkyl- or aryl-sulfonate, under similar conditions.

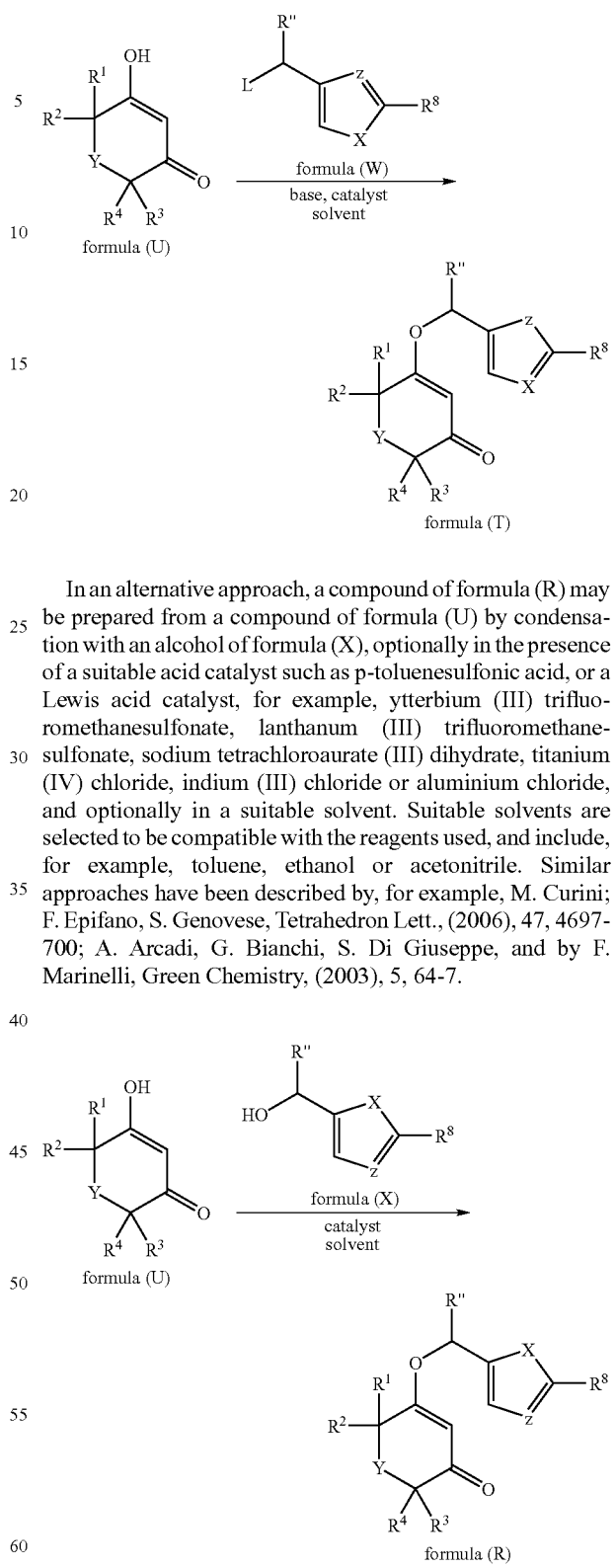

formula (U)

formula (T)

In an alternative approach, a compound of formula (R) may be prepared from a compound of formula (U) by condensation with an alcohol of formula (X), optionally in the presence of a suitable acid catalyst such as p-toluenesulfonic acid, or a Lewis acid catalyst, for example, ytterbium (III) trifluoromethanesulfonate, lanthanum (III) trifluoromethanesulfonate, sodium tetrachloroaurate (III) dihydrate, titanium (IV) chloride, indium (III) chloride or aluminium chloride, and optionally in a suitable solvent. Suitable solvents are selected to be compatible with the reagents used, and include, for example, toluene, ethanol or acetonitrile. Similar approaches have been described by, for example, M. Curini; F. Epifano, S. Genovese, Tetrahedron Lett., (2006), 47, 4697-700; A. Arcadi, G. Bianchi, S. Di Giuseppe, and by F. Marinelli, Green Chemistry, (2003), 5, 64-7.

formula (U)

formula (R)

Alternatively, the condensation may be effected in the presence of suitable coupling agents such as 2-chloro-1-methylpyridinium iodide, N,N'-dicyclohexylcarbodiimide, 1-(3-dimethylaminopropyl)-3-ethylcarbodiimide and N,N-carbodiimidazole and a suitable base such a triethylamine or pyridine in a suitable solvent such as tetrahydrofuran, acetonitrile or dichloromethane, or in the presence of a triarylphosphine (such as triphenylphosphine) and a dialkyl azidodicarboxylate (preferably diethyl azidodicarboxylate or diisopropyl azidodicarboxylate) and in a suitable solvent such as diethyl ether, tetrahydrofuran or 1,4-dioxane as described, for example, by O. Mitsunobu, Synthesis (1981), 1, 1-28.

Using similar processes, a compound of formula (T) may be prepared by reaction of a compound of formula (U) with a compound of formula (Y).

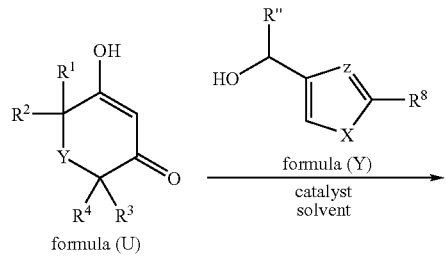

formula (U)

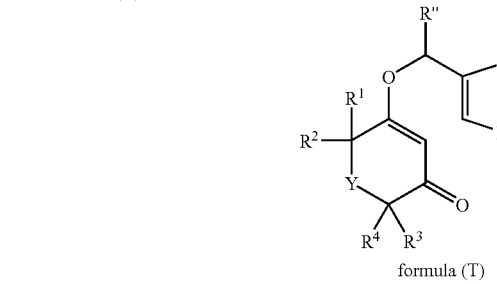

formula (T)

Additional compounds of formula (R) wherein $R^8$ is an aromatic or heteroaromatic moiety, or is an alkyl, alkenyl or alkynyl group, may be prepared by the reaction of a compound of formula (Z), wherein Q is an atom or group suitable for undergoing cross-coupling reactions (for example Q is chlorine, bromine or iodine, or a haloalkylsulfonate such as trifluoromethanesulfonate), and R" is as defined for a compound of formula (Q), with a suitable coupling partner under conditions described in the literature for Suzuki-Miyaura, Sonogashira, Stille and related cross-coupling reactions.

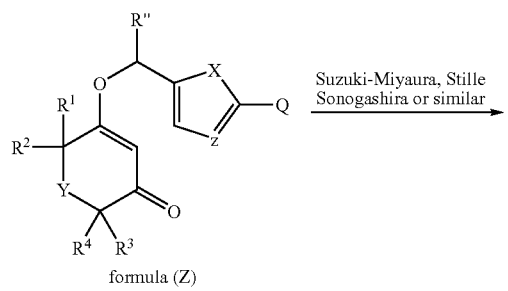

formula (Z)

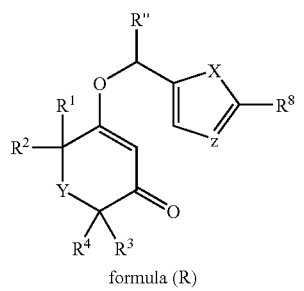

formula (R)

For example, a compound of formula (Z) may be treated with an aryl-, heteroaryl-, alkyl-, alkenyl- or alkynylboronic acid, $R^8$—$B(OH)_2$, boronate ester, $R^8$—$B(OR''')_2$, (preferably an ester wherein the fragment —$B(OR''')_2$ represents a cyclic boronate ester derived from a 1,2- or a 1,3-alkanediol, such as pinacol, 2,2-dimethyl-1,3-propanediol and 2-methyl-2,4-pentanediol), or a metal (especially potassium) aryl-, heteroaryl, alkyl-, alkenyl- and alkynyltrifluoroborate salt, $M^+[R^8—BF_3]^+$ in the presence of a suitable palladium catalyst, a suitable ligand and a suitable base in the presence of a suitable solvent, under Suzuki-Miyaura conditions (see, for example I. Kondolff, H. Doucet and M, Santelli, Tetrahedron, (2004), 60, 3813-3818; F. Bellina, A. Carpita and R. Rossi, Synthesis (2004), 15, 2419-2440; G. Molander and C-S Yun, Tetrahedron, (2002), 58, 1465-1470; G. Zou, Y. K. Reddy and J. Falck, Tetrahedron Lett., (2001), 42, 4213-7215; A. Suzuki, Journal of Organometallic Chemistry, (2002), 653, 83; H. Stefani, R. Cella and A. Vieira, Tetrahedron, (2007), 62, 3623-3658; G. Molander, C-S Yun, M. Ribagorda and B. Biolatto, J. Org. Chem., (2003), 68, 5534-5539; S. Darses, G. Michaud and J-P, Genêt, Eur. J. Org. Chem., (1999), 1877-1883; K. Billingsley and S. Buchwald, J. Am. Chem. Soc., (2007), 129, 3358-3366).

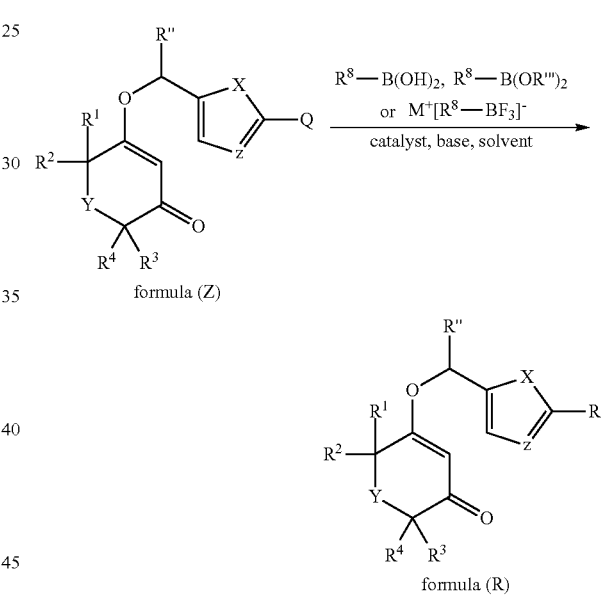

formula (R)

Similarly, a compound of formula (T) may be prepared from a compound of formula (AA), wherein Q is as defined previously, and R" is as defined for a compound of formula (Z), by analogous methods using appropriate starting materials.

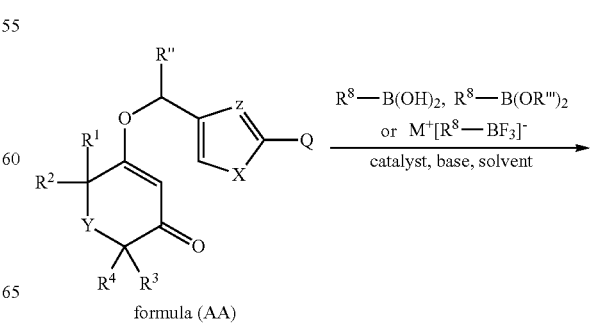

formula (AA)

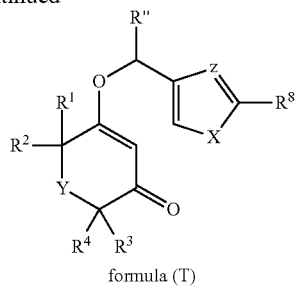

formula (T)

A compound of formula (Z) may be prepared from a compound of formula (U), by reaction with a compound of formula (BB) wherein L is a suitable leaving group such as a halogen or an alkyl- or aryl-sulfonate, by processes analogous to those described above for the preparation of a compound of formula (R) from a compound of formula (U). Alternatively, a compound of formula (Z) may be prepared by reaction of a compound of formula (L) with a compound of formula (CC) by processes analogous to those described above for the preparation of a compound of formula (R) from a compound of formula (L).

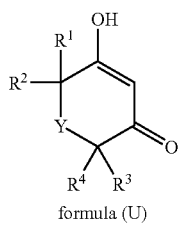

formula (BB)

base, solvent

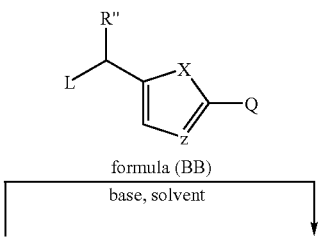

formula (U)                formula (Z)

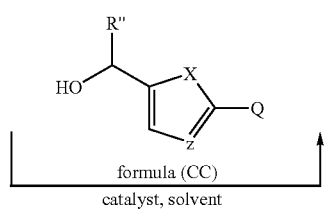

formula (CC)

catalyst, solvent

By analogous processes to those described above, a compound of formula (AA) may be prepared from a compound of formula (U) by alkylation with a compound of formula (DD), wherein L is a suitable leaving group such as a halogen or an alkyl- or aryl-sulfonate, or by alkylation with a compound of formula (EE).

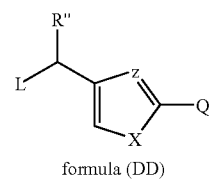

formula (DD)

base, solvent

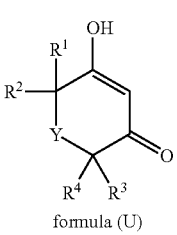  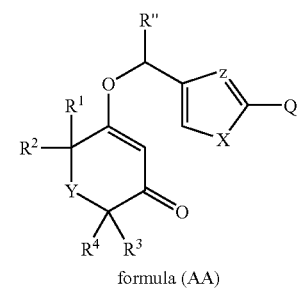

formula (U)                formula (AA)

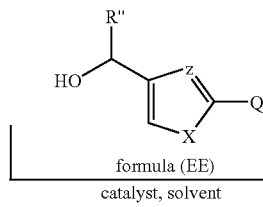

formula (EE)

catalyst, solvent

In an alternative approach, a compound of formula (U) may be treated with a halogenating agent such as phosphorus oxychloride, phosphorus pentachloride, phosphorus pentabromide, phosphorus oxybromide, oxalyl chloride or oxalyl bromide, optionally in a suitable solvent such as toluene, chloroform, dichloromethane with optionally the presence of dimethylformamide, and the resulting vinyl halide of formula (FF), wherein Hal is chlorine or bromine may be converted by reaction with an alcohol of formula (X), or of formula (Y), or of formula (CC) or of formula (EE) optionally in the presence of a suitable base such as sodium hydride, sodium tert-butoxide, potassium tert-butoxide and a suitable solvent such as tetrahydrofuran, 1,4-dioxane, diethylene glycol dimethyl ether to give a compound of formula (R), formula (T), formula (Z) and formula (AA) respectively:

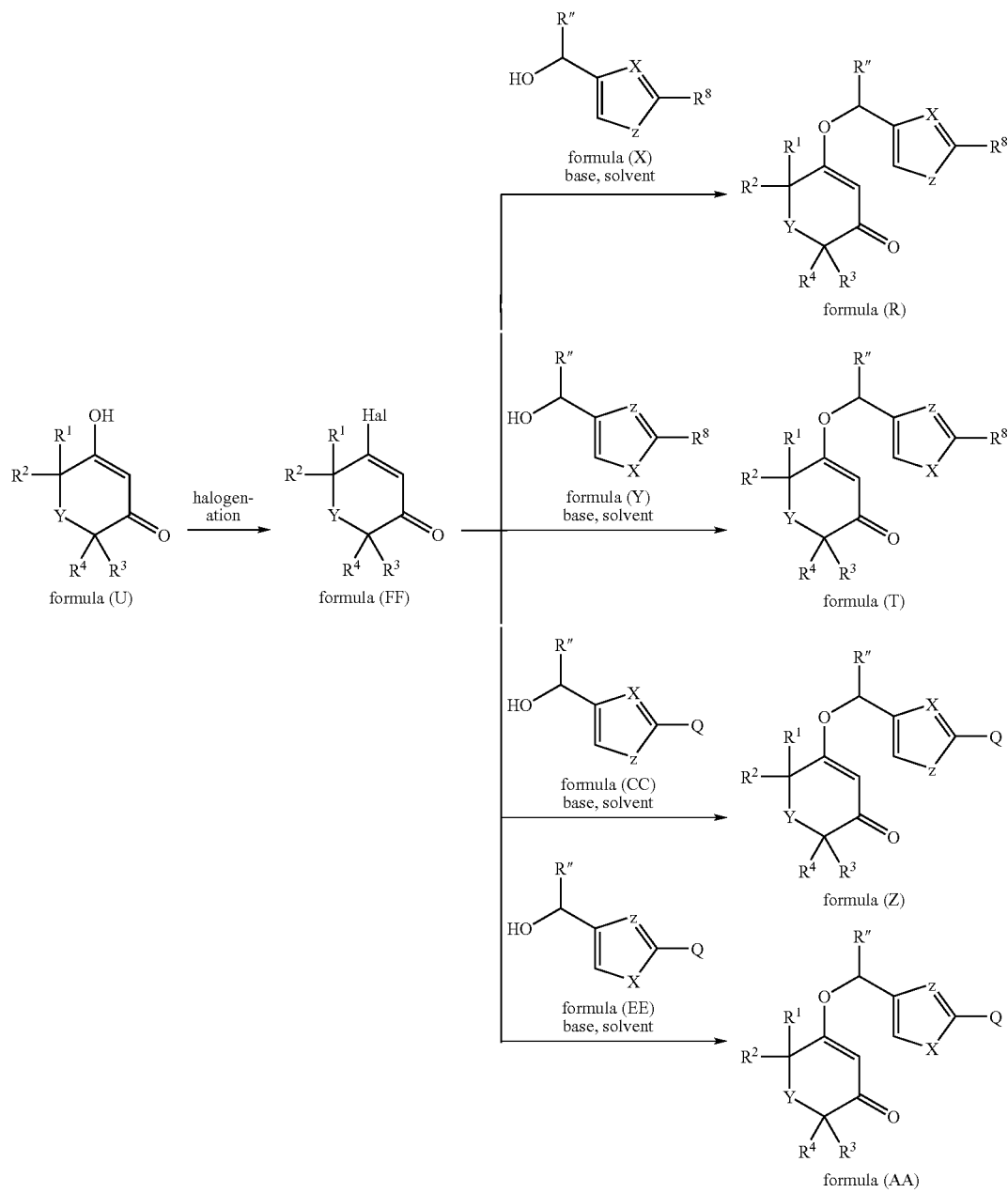

Compounds of formula (V), formula (W), formula (X), formula (Y), formula (BB), formula (CC), formula (DD) and formula (EE) are known or may be prepared by known methods from known compounds (see, for example T. Denton, X. Zhang, J. Cashman, J. Med. Chem., (2005), 48, 224-239; J. Reinhard, W. Hull, C.-W. von der Lieth, U. Eichhorn, H.-C. Kliem, J. Med. Chem., (2001), 44, 4050-4061; H. Kraus and H. Fiege, DE19547076; M. Boys, L. Schretzman, N. Chandrakumar, M. Tollefson, S. Mohler, V. Downs, T. Penning, M. Russell, J. Wendt, B. Chen, H. Stenmark, H. Wu, D. Spangler, M. Clare, B. Desai, I. Khanna, M. Nguyen, T. Duffin, V. Engleman, M. Finn, S. Freeman, M. Hanneke, J. Keene, J. Klover, G. A. Nickols, M. Nickols, C. Steininger, M. Westlin, W. Westlin, Y. Yu, Y. Wang, C. Dalton, S. A. Norring, Bioorg. Med. Chem. Lett., (2006), 16, 839-844; A. Silberg, A. Benko, G. Csavassy, Chem. Ber., (1964), 97, 1684-1687; K. Brown and R. Newbury, Tetrahedron Lett., (1969), 2797; A. Jansen and M. Szelke, J. Chem. Soc., (1961), 405; R. Diaz-Cortes, A. Silva and L. Maldonado, Tetrahedron Lett., (1997), 38(13), 2007-2210; M. Friedrich, A. Waechtler and A. De Meijure, Synlett., (2002), 4, 619-621; F. Kerdesky and L. Seif, Synth. Commun., (1995), 25 (17), 2639-2645; Z. Zhao, G. Scarlato and R. Armstrong., Tetrahedron Lett., (1991), 32 (13), 1609-1612; K-T. Kang and S. Jong, Synth. Commun. (1995), 25 (17), 2647-2653; M. Altamura and E. Perrotta, J. Org. Chem., (1993), 58 (1), 272-274).

Compounds of formula (U), wherein Y is O, are known compounds or may be prepared by routes analogous to those described in the literature (see, for example, M. Morgan and E. Heyningen, J. Am. Chem. Soc., (1957), 79, 422-4; I. K. Korobitsyna and K. Pivnitskii, Zhurnal Obshchei Khimii, (1960), 30, 4016-4023; T. Terasawa, and T. Okada, J. Org.

Chem., (1977), 42 (7), 1163; R. Anderson et al. US 1988/156269; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. E. Scott, J. Smith, K. Whiteaker, and W. Carroll, J. Med. Chem., (2006), 49(23), 6869-6887. Compounds of formula (U), wherein Y is S, are known compounds or may be prepared by routes analogous to those described in the literature (see, for example, E. Fehnel and A. Paul, J. Am. Chem. Soc., (1955), 77, 4241; E. Er and P. Margaretha, Helvetica Chimica Acta (1992), 75(7), 2265-69; H. Gayer et al., DE 3318648 A1). Compounds of formula (U), wherein Y is C=O, are known compounds or may be prepared by routes analogous to those described in the literature (see, for example, R. Gotz et al. WO2000/075095).

In a further approach, a compound of formula (A) wherein Y is O, S or C=O, may be prepared by reaction of a compound of formula (U) with a heteroaryl lead tricarboxylate under conditions described in the literature (for example see, J. Pinhey and B. Rowe, Aust. J. Chem., (1979), 32, 1561-6; J. Morgan and J. Pinhey, J. Chem. Soc. Perkin Trans. 1, (1990), 3, 715-20; J. Pinhey and E. Roche, J. Chem. Soc. Perkin Trans. 1, (1988), 2415-21). Preferably the heteroaryl lead tricarboxylate is a heteroaryl triacetate of formula (GG) and the reaction is conducted in the presence of a suitable ligand (for example N,N-dimethylaminopyridine, pyridine, imidazole, bipyridine, and 1,10-phenanthroline, preferably one to ten equivalents of N,N-dimethylaminopyridine with respect to compound (U)) and in a suitable solvent (for example chloroform, dichloromethane and toluene, preferably chloroform and optionally in the presence of a co-solvent such as toluene) at 25° C. to 100° C. (preferably 60-90° C.).

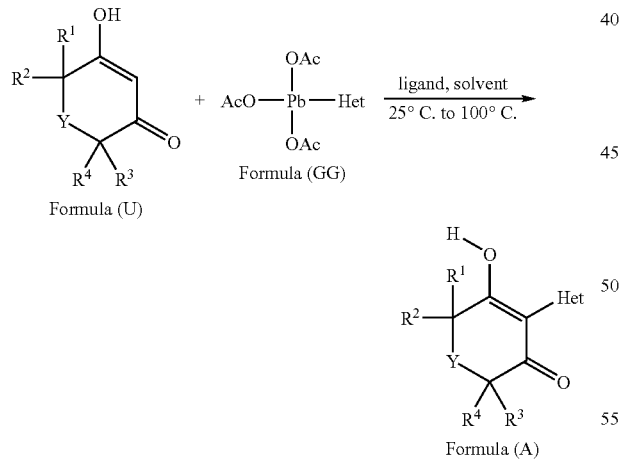

A compound of formula (GG) may be prepared from a compound of formula (HH) by treatment with lead tetraacetate in a suitable solvent (for example chloroform) at 25° C. to 100° C. (preferably 25-50° C.), optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-20).

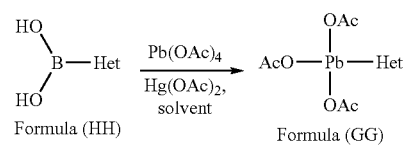

Preferred coupling partners include heteroarylboronic acids, $(HH_1)$ to $(HH_8)$, wherein $R^7$, $R^8$, $R^9$, $R^{10}$, $R^{11}$, $R^{12}$, X, $W^1$, $W^2$, $W^3$, $W^4$ and Z are as defined above.

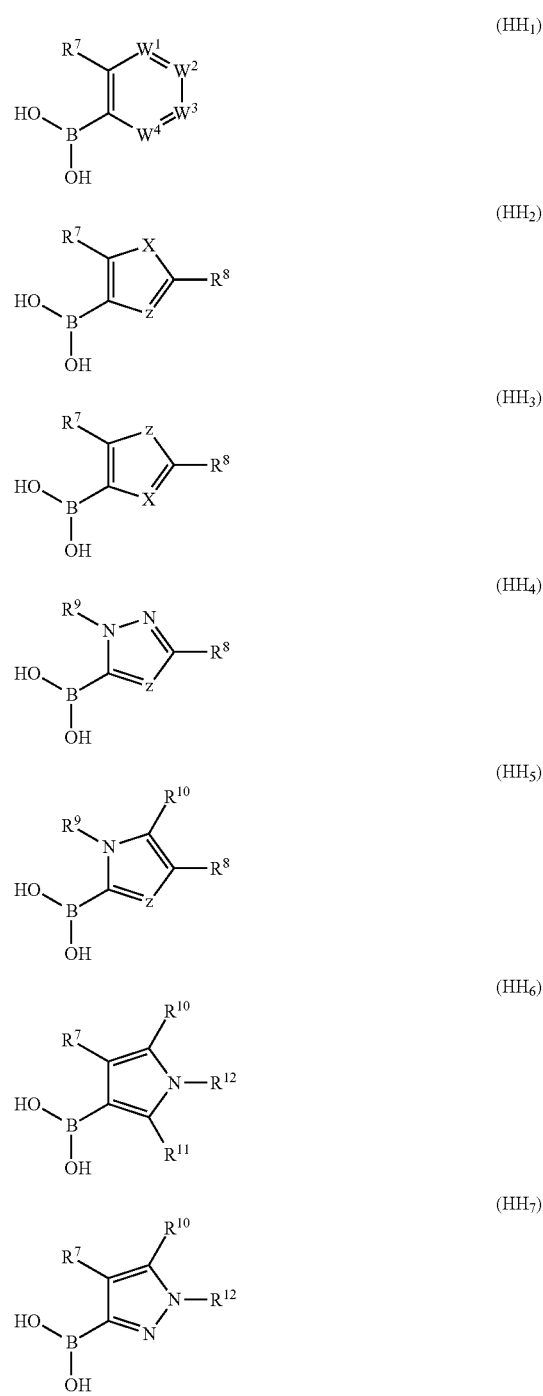

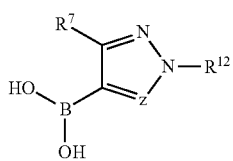
(HH8)

Heteroarylboronic acids of formula (HH) are known compounds, or may be prepared from known compounds by known methods (see for example A. Voisin et al., Tetrahedron (2005); 1417-1421; A. Thompson et al., Tetrahedron (2005), 61, 5131-5135; K. Billingsley and S. Buchwald, J. Am. Chem. Soc., (2007), 129, 3358-3366; N. Kudo, M. Pauro and G. Fu, Angew. Chem. Int. Ed., (2006), 45, 1282-1284; A. Ivachtchenko et al., J. Heterocyclic Chem., (2004), 41(6), 931-939; H. Matondo et al., Synth. Commun., (2003), 33 (5) 795-800; A. Bouillon et al., Tetrahedron, (2003), 59, 10043-10049; W. Li et al., J. Org. Chem., (2002), 67, 5394-5397; C. Enguehard et al., J. Org. Chem. (2000), 65, 6572-6575; H-N Nguyen, X. Huang and S. Buchwald, J. Am. Chem. Soc., (2003), 125, 11818-11819, and references therein).

In a further approach, a compound of formula (A) may be prepared from compounds of formula (JJ) by reaction with a heteroaryl boronic acid of formula (HH), in the presence of a suitable palladium catalyst and a base, and preferably in a suitable solvent.

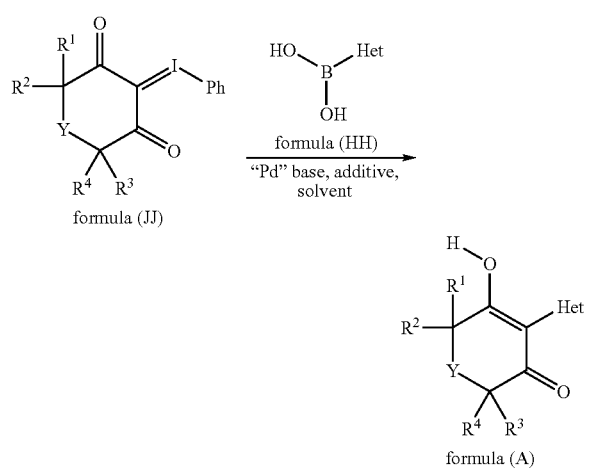

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenyl-phosphine ($PPh_3$), tricyclopentylphosphine or tricyclohexylphosphine and the selected solvent, with a compound of formula (JJ), a heteroaromatic boronic acid of formula (HH) and a base. Also suitable are bidendate ligands, for example 1,1'-bis(diphenyl-phosphino) ferrocene or 1,2-bis(diphenylphosphino)ethane. By heating the reaction medium, the palladium(II) complex or palladium (0) complex desired for the C—C coupling reaction is thus formed "in situ", and then initiates the C—C coupling reaction. The palladium catalysts are used in an amount of from 0.001 to 50 mol %, preferably in an amount of from 0.1 to 15 mol %, based on the compound of formula (JJ). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

A compound of formula (JJ) may be prepared from a compound of formula (U) by treatment with (diacetoxy)iodobenzene according to the procedures of K. Schank and C. Lick, Synthesis, (1983), 392, or of Z Yang et al., Org. Lett., (2002), 4 (19), 3333.

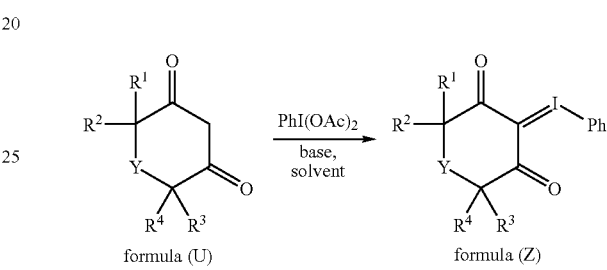

In a further approach a compound of formula (A) may be prepared via the rearrangement of a compound of formula (KK), in the presence of a reagent which promotes rearrangement, such as a metal alkoxide (preferably in an amount equal to or greater than 100% with respect to compound of formula (KK)) or cyanide anion, for example 0.001-25% potassium cyanide, 0.001-25% sodium cyanide, or 0.001-25% acetone cyanohydrin with respect to a compound of formula (KK). This reaction is also optionally performed in a suitable solvent (for example acetonitrile) at a suitable temperature (typically 25-100° C.) with a suitable base (such as triethylamine).

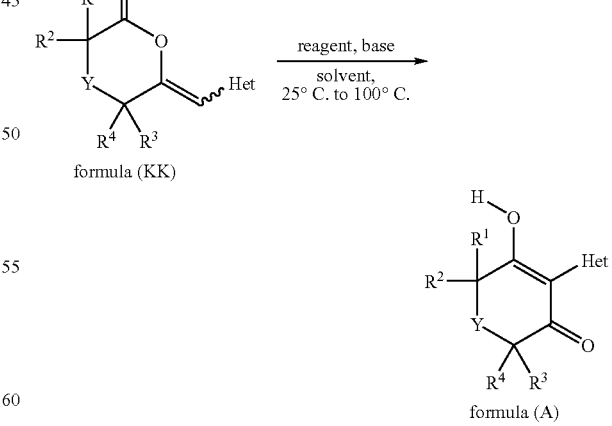

A compound of formula (KK) may be prepared from a compound of formula (LL) by treatment with a catalyst such as palladium(II) dichloride or silver carbonate (preferably 0.001-50% silver carbonate with respect to compound of formula (LL)), in the presence of a suitable solvent (for example acetonitrile) at a suitable temperature (typically 25° C. to 150° C., preferably 120° C. under microwave heating). Similar lactonisations are known in the literature (see for example P. Huang and W. Zhou, Tetrahedron Asymmetry (1991), 2(9), 875-878.)

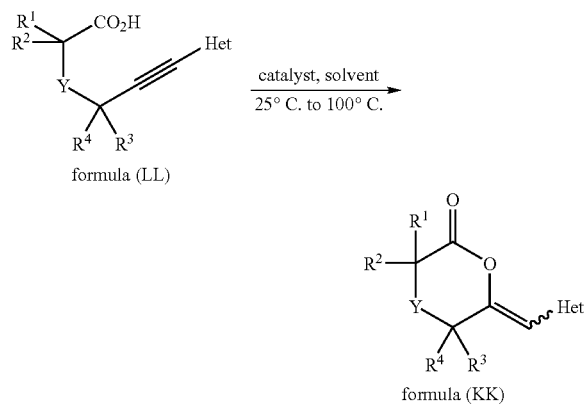

formula (LL)

formula (KK)

A compound of formula (LL) may be prepared by the saponification of a compound of formula (MM) where R'''' is alkyl (preferably methyl or ethyl) under known conditions, and a compound of formula (MM) may be prepared from a compound of formula (NN) by Sonogashira coupling with a suitable heteroaromatic halide, (such as a bromide or iodide), Het-hal, in the presence of a palladium catalyst (for example bis(triphenylphosphine) palladium(II) dichloride in an amount typically 0.001-25% of compound of formula (NN)), copper source (for example copper(I) iodide in an amount typically 0.001-50% of compound of formula (NN)), base (such as diethylamine or triethylamine), and optionally in a suitable solvent. Similar couplings are known in the literature (see for example see, Z. Gan and R. Roy, Canadian Journal of Chemistry (2002), 80(8), 908-916).

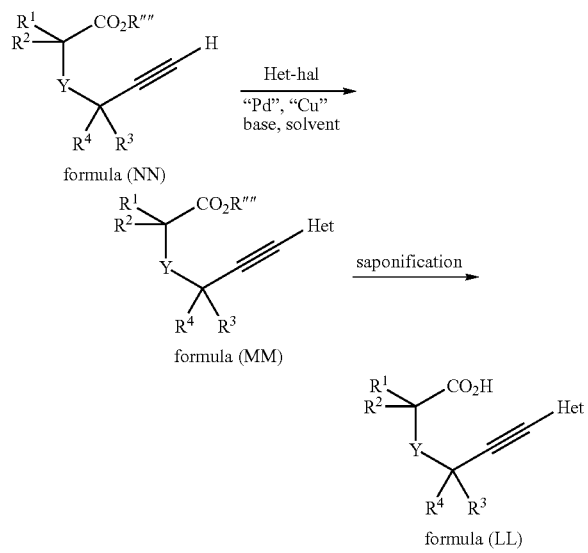

formula (NN)

formula (MM)

formula (LL)

Compounds of formula (NN) are known compounds or may be prepared by routes analogous to those described in the literature (see, for example, I. Drizin et al, WO2001/066544; M. Yamamoto, Journal of Chemical Research, Synopses (1991), (7), 165; P. Machin, U.S. Pat. No. 4,774,253; M. Morgan and E. Heyningen, J. Am. Chem. Soc., (1957), 79, 422-424).

In a further approach, a compound of formula (A) may be prepared from a compound of formula I or IA (wherein G is $C_{1-4}$ alkyl) by hydrolysis, preferably in the presence of an acid catalyst such as hydrochloric acid and optionally in the presence of a suitable solvent such as tetrahydrofuran. A compound of formula I (wherein G is preferably $C_{1-4}$ alkyl) may be prepared by reacting a compound of formula (OO) (wherein G is preferably $C_{1-4}$ alkyl, and Hal is a halogen, preferably bromine or iodine), with a heteroaryl boronic acid, Het-B(OH)$_2$, of formula (HH) in the presence of a suitable palladium catalyst (for example 0.001-50% palladium(II) acetate with respect to compound (OO) and a base (for example 1 to 10 equivalents potassium phosphate with respect to compound (OO) and preferably in the presence of a suitable ligand (for example 0.001-50% (2-dicyclohexylphosphino)-2',6'-dimethoxybiphenyl with respect to compound (OO), and in a suitable solvent (for example toluene), preferably between 25° C. and 200° C. Similar couplings are known in the literature (see for example, Y. Song, B. Kim and J.-N. Heo, Tetrahedron Letters (2005), 46(36), 5987-5990).

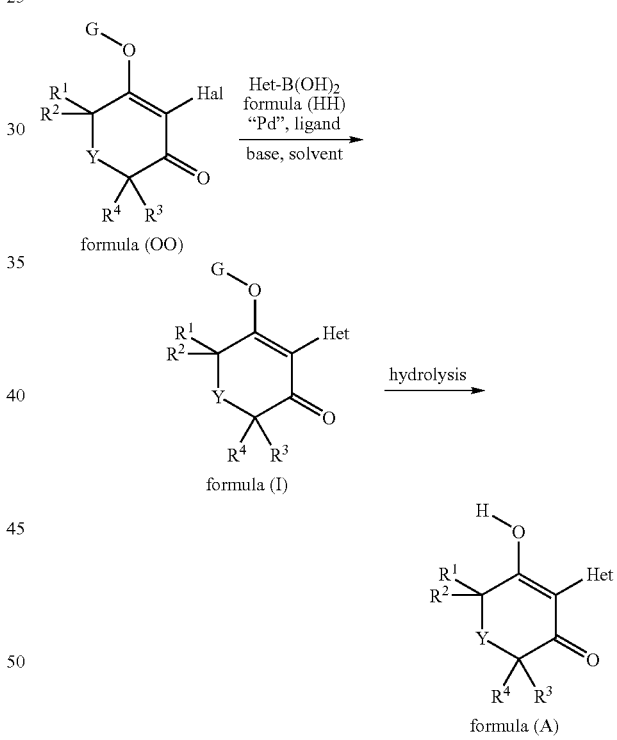

formula (OO)

formula (I)

formula (A)

A compound of formula (O) may be prepared by halogenating a compound of formula (U), followed by alkylation of the resulting halide of formula (PP) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (O) may be prepared by alkylating a compound of formula (U) with a $C_{1-4}$ alkyl halide or a tri-$C_{1-4}$-alkylorthoformate, and halogenating the resulting enone of formula (QQ) under known conditions (see for example Y. Song, B. Kim and J.-N. Heo, Tetrahedron Letters (2005), 46(36), 5987-5990).

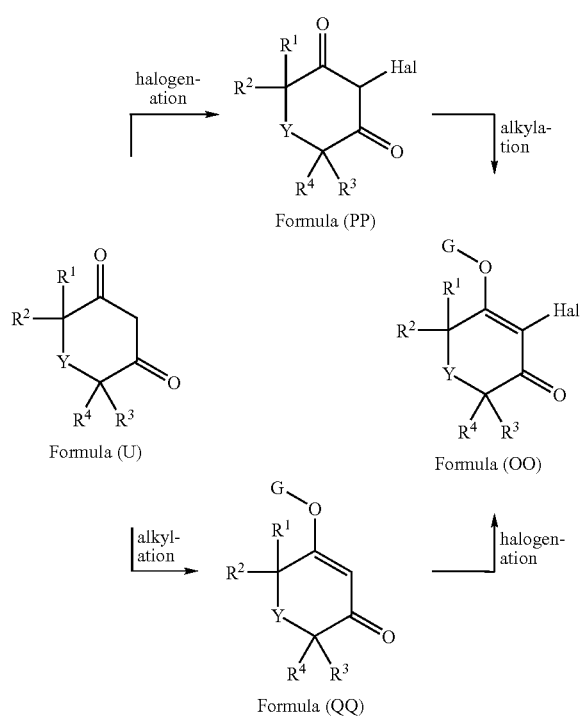

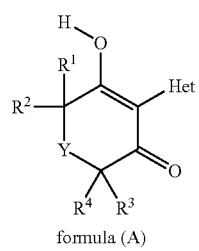

formula (A)

Those skilled in the art will appreciate that compounds of formula I may contain a heteroaromatic moiety bearing one or more substituents capable of being transformed into alternative substituents under known conditions, and that these compounds may themselves serve as intermediates in the preparation of additional compounds of formula I. For example, a heterocycle of formula (RR) wherein $Q_1$ is alkenyl or alkynyl, may be reduced to a compound of formula (Q) wherein $R^8$ is alkyl under known conditions.

In a further approach, a compound of formula (A) may be prepared by reacting a compound of formula (U) with a suitable heteroaryl halide (such as an iodide or bromide), Het-hal, in the presence of a suitable palladium catalyst (for example 0.001-50% palladium(II) acetate with respect to compound (U)) and a base (for example 1 to 10 equivalents potassium phosphate with respect to compound (U)) and preferably in the presence of a suitable ligand (for example 0.001-50% (2-dicyclohexylphosphino)-2',4',6'-triisopropylbiphenyl with respect to compound (U)), and in a suitable solvent (for example dioxane), preferably between 25° C. and 200° C. Similar couplings are known in the literature (see for example, J. Fox, X. Huang, A. Chieffi, and S. Buchwald, J. Am. Chem. Soc. (2000), 122, 1360-1370; B. Hong et al. WO 2005/000233). Alternatively, a compound of formula (A) may be prepared by reacting a compound of formula (U) with a suitable heteroaryl halide (such as an iodide or bromide), Het-hal, in the presence of a suitable copper catalyst (for example 0.001-50% copper(I) iodide with respect to compound (U)) and a base (for example 1 to 10 equivalents potassium carbonate with respect to compound (U)) and preferably in the presence of a suitable ligand (for example 0.001-50% L-proline with respect to compound (U)), and in a suitable solvent (for example dimethylsulfoxide), preferably between 25° C. and 200° C. Similar couplings are known in the literature for aryl halides (see for example, Y. Jiang, N. Wu, H. Wu, and M. He, Synlett, (2005), 18, 2731-2734).

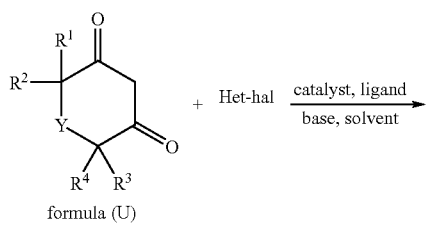

formula (U)

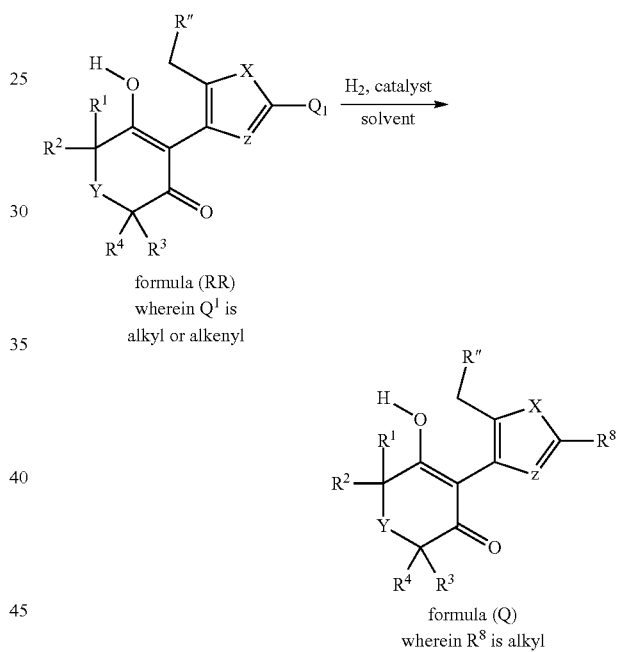

formula (RR)
wherein $Q_1$ is
alkyl or alkenyl formula (Q)
wherein $R^8$ is alkyl Furthermore, a compound of formula (RR) wherein $Q_1$ is an atom or group suitable for cross-coupling chemistry such as a halogen or a haloalkylsulfonate may undergo Suzuki-Miyaura, Stille, Sonogashira and related reactions under known conditions to give additional compounds of formula Q.

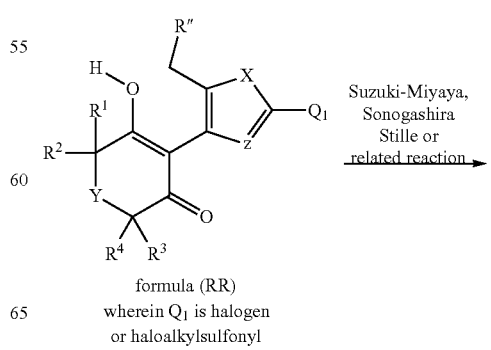

formula (RR)
wherein $Q_1$ is halogen
or haloalkylsulfonyl

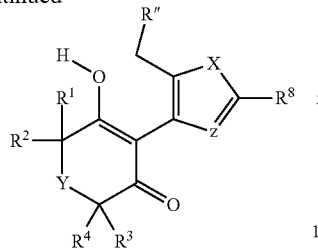

formula (Q)
wherein R⁸ is aryl, heteroaryl, alkenyl, alkynyl or similar

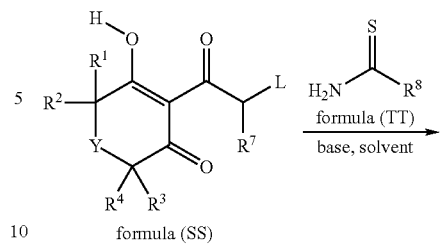

formula (SS)

Those skilled in the art will appreciate that transformations of this type are not restricted to compounds of formula (RR), but may in general be applied to any compound of formula I where Het is a heterocycle substituted by an atom or group $Q_1$ suitable for further derivatisation.

In a further approach to compounds of formula (A), wherein Het is a group of formula ($R_2$), X is S, and Y is N, a compound of formula (SS) wherein L is a suitable leaving group such as a halogen or an alkyl- or haloalkylsulfonate, may be treated with a compound of formula (TT), optionally in the presence of a suitable base (such as triethylamine or pyridine), and optionally in a suitable solvent (such as water, toluene, acetone, ethanol or isopropanol) according to known procedures, (see, for example, E. Knott, J. Chem. Soc., (1945), 455; H. Brederick, R. Gompper, Chem. Ber. (1960), 93, 723; B. Friedman, M. Sparks and R. Adams, J. Am. Chem. Soc., (1937), 59, 2262).

formula (A)
where Het is ($R_2$)
X is S and Z is N

Alternatively, a compound of formula (SS) may be treated with thiourea, by known procedures (see, for example, V. Pshenichniya, O. Gulyakevich and V. Kripach, Chemistry of Heterocyclic Compounds, (1990), 10, 1409-1412), and the resulting product of formula (UU) may be converted into additional compounds of formula (A) by conversion to a halide of formula (VV), wherein Hal is chlorine, bromine or iodine, under Sandmeyer conditions, and a compound of formula (VV) may be converted to compounds of formula (A) by cross-coupling under known conditions for the Suzuki-Miyaura, Sonogashira, Stille and related reactions, as described previously.

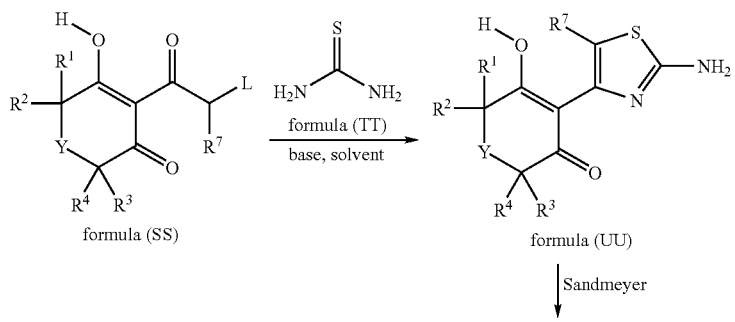

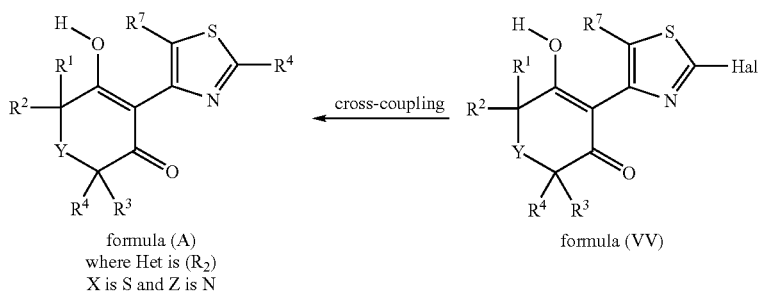

formula (A)
where Het is ($R_2$)
X is S and Z is N

A compound of formula (SS) may be prepared from a compound of formula (U) under known conditions (see, for example, V. Pshenichniya, O. Gulyakevich and V. Kripach, Chemistry of Heterocyclic Compounds, (1990), 10, 1409-1412; V. Pshenichniya, O. Gulyakevich and V. Kripach, Russian Journal of Organic Chemistry, (1989), 25 (9), 1882-1888).

The compounds of the formulae (B), (R) and (T) are novel and have been specifically designed for the synthesis of the compounds of the formula I.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha.

Preferred formulations have especially the following compositions:
(%=percent by weight):

Emulsifiable Concentrates:

| active ingredient: | 1 to 95%, preferably 60 to 90% |
| surface-active agent: | 1 to 30%, preferably 5 to 20% |
| liquid carrier: | 1 to 80%, preferably 1 to 35% |

Dusts:

| active ingredient: | 0.1 to 10%, preferably 0.1 to 5% |
| solid carrier: | 99.9 to 90%, preferably 99.9 to 99% |

Suspension Concentrates:

| active ingredient: | 5 to 75%, preferably 10 to 50% |
| water: | 94 to 24%, preferably 88 to 30% |
| surface-active agent: | 1 to 40%, preferably 2 to 30% |

Wettable Powders:

| active ingredient: | 0.5 to 90%, preferably 1 to 80% |
| surface-active agent: | 0.5 to 20%, preferably 1 to 15% |
| solid carrier: | 5 to 95%, preferably 15 to 90% |

Granules:

| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include especially cereals, cotton, soybeans, sugar beet, sugar cane, plantation crops, rape, maize and rice, and for non-selective weed control. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 592 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIH-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+triallate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]bicyclo[3.2.1]oct-3-en-2-one.

The compounds of formula I according to the invention can also be used in combination with safeners. Preferably, in these mixtures, the compound of the formula I is one of those compounds listed in Tables 1 to 592 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+N-(2-methoxybenzoyl)-4-[(methylaminocarbonyl)amino]-benzenesulfonamide, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000, or other readily available resources. R-29148 is described, for example by P. B. Goldsbrough et al., Plant Physiology, (2002), Vol. 130 pp. 1497-1505 and references, PPG-1292 is known from WO09211761 and N-(2-methoxybenzoyl)-4-[(methylaminocarbonyl)amino]benzenesulfonamide is known from EP365484.

Depending on the use, the herbicidal compositions according to the present invention may contain a compound of the formula I, a further herbicide as mixing partner and a safener, as mentioned above.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula I, optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

The mixtures can advantageously be used in the above-mentioned formulations (in which case "active ingredient" relates to the respective mixture of compound of formula I with the mixing partner).

The following examples illustrate the invention further but do not limit the invention.

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 and P1, are drawn as an arbitrary single enol tautomer, but it should be inferred that this description covers both the diketone form and any possible enols which could arise through tautomerism. Furthermore, some of the compounds shown below, and in Table T1 and P1, are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

PREPARATION EXAMPLES

Example 1

Preparation of 6-[5-(4-chloro-3-methylphenyl)-2-methylthiophen-3-yl]-2,2,4,4-tetramethyl-cyclohexane-1,3,5-trione (Compound T4 in Table T1)

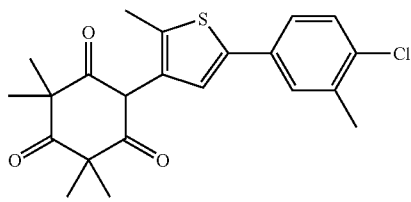 [SMILES: Cc1cc(-c2cc(C3C(=O)C(C)(C)C(=O)C(C)(C)C3=O)c(C)s2)ccc1Cl]

Step 1

Preparation of 5-(5-bromothiophen-2-ylmethoxy)-2,2,6,6-tetramethylcyclohex-4-ene-1,3-dione

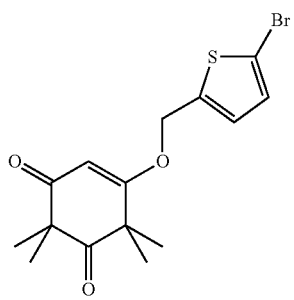 [SMILES: CC1(C)C(=O)C=C(OCc2ccc(Br)s2)C(C)(C)C1=O]

To a solution of 5-bromothiophen-2-ylmethanol (6.76 g, 35 mmol) in tetrahydrofuran (100 ml) at 0° C. is added, carefully, sodium hydride, 60% dispersion in mineral oil, (1.2 g, 30 mmol over a period of 10 minutes. The reaction is allowed to warm to room temperature and stirred for a further hour. 5-Chloro-2,2,6,6-tetramethylcyclohex-4-ene-1,3-dione (5.02 mg, 25 mmol) is then added in one portion and the reaction mixture is allowed to stir at room temperature for 17 hours. The reaction is concentrated in vacuo and purified by flash chromatography on silica gel to give the desired compound as a white solid (4.45 g)

Step 2

Preparation of 6-[5-(4-chloro-3-methylphenyl)-2-methylthiophen-3-yl]-2,2,4,4-tetramethyl-cyclohexane-1,3,5-trione

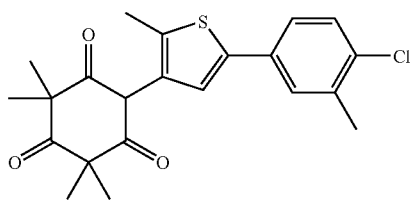 [SMILES: Cc1cc(-c2cc(C3C(=O)C(C)(C)C(=O)C(C)(C)C3=O)c(C)s2)ccc1Cl]

A mixture of 5-(5-bromothiophen-2-ylmethoxy)-2,2,6,6-tetramethyl-cyclohex-4-ene-1,3-dione (107 mg, 0.3 mmol), 4-chloro-m-tolyl boronic acid (60 mg, 0.35 mmol), palladium acetate (4 mg, 0.015 mmol), Ru-Phos (14 mg, 0.03 mmol) and caesium carbonate (130 mg, 0.4 mmol) in toluene (2 ml) is heated to 180° C. for 30 minutes under microwave irradiation and the resulting material is purified by flash chromatography on silica gel to give 6-[5-(4-chloro-3-methylphenyl)-2-methylthiophen-3-yl]-2,2,4,4-tetramethyl-cyclohexane-1,3,5-trione.

Example 2

Preparation of 6-[2-(2,5-dichlorophenyl)-5-methylthiazol-4-yl]-2,2,4,4-tetramethyl-cyclohexane-1,3,5-trione (Compound T10 in Table T1)

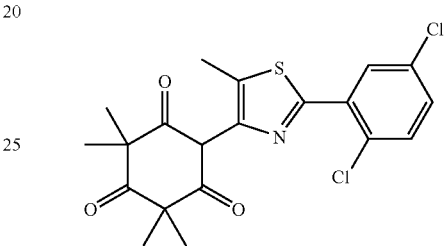

Step 1

Preparation of 5-(2-bromothiazol-5-ylmethoxy)-2,2,6,6-tetramethylcyclohex-4-ene-1,3-dione

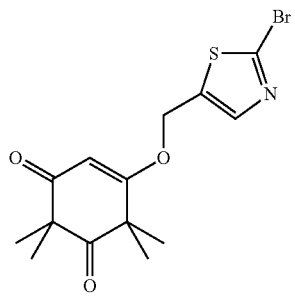 [SMILES: CC1(C)C(=O)C=C(OCc2cnc(Br)s2)C(C)(C)C1=O]

To a suspension of sodium hydride, 60% dispersion in mineral oil solution (1.6 g, 40 mmol) in tetrahydrofuran (50 ml) is added a solution of (2-bromothiazol-5-yl)methanol (6.75 g, 35 mmol) in tetrahydrofuran (50 ml) at 0° C. A solution of 5-chloro-2,2,6,6-tetramethylcyclohex-4-ene-1,3-dione (7.0 g, 35 mmol) in tetrahydrofuran (50 ml) is then added and the reaction mixture is heated to reflux for 18 hours. The reaction mixture is poured into water, acidified to pH4 with dilute aqueous hydrochloric acid and extracted with ethyl acetate (4×50 ml). The combined organic layers are dried over anhydrous magnesium sulfate, filtered and the filtrate is evaporated to a brown oil. The crude product is purified by flash chromatography on silica gel to give 5-(2-bromothiazol-5-ylmethoxy)-2,2,6,6-tetramethylcyclohex-4-ene-1,3-dione (6.75 g).

Step 2

Preparation of 6-[2-(2,5-dichlorophenyl)-5-methylthiazol-4-yl]-2,2,4,4-tetramethyl-cyclohexane-1,3,5-trione

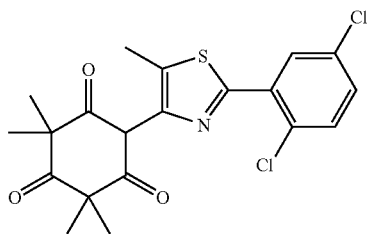 [SMILES: Cc1sc(-c2cc(Cl)ccc2Cl)nc1C1C(=O)C(C)(C)C(=O)C(C)(C)C1=O]

2,5-dichlorophenylboronic acid (266 mg, 1.39 mmol), 5-(2-bromothiazol-5-ylmethoxy)-2,2,6,6-tetramethylcyclohex-4-ene-1,3-dione (250 mg, 0.7 mmol), toluene (3 ml), caesium carbonate (310 mg, 0.95 mmol) and [1,3-bis(2,6-diisopropyl)imidazol-2-ylidene](3-chloropyridyl)palladium II dichloride (60 mg, 0.12 mmol) are mixed together in a microwave vial and heated to 150° C. for 30 min under microwave irradiation. The reaction mixture is cooled, filtered, evaporated and purified by flash chromatography on silica gel to give an orange oil. The oil is dissolved in diglyme (3 ml) and 1-butyl-3-methyl imidazolium bis(trifluoromethylsulfonyl)imide (0.1 ml) and heated under microwave irradiation at 210° C. for 30 min. The reaction mixture is cooled to room temperature, the solvent is evaporated under reduced pressure and the residue is purified by flash chromatography on silica gel to give 6-[2-(2,5-dichlorophenyl)-5-methylthiazol-4-yl]-2,2,4,4-tetramethylcyclohexane-1,3,5-trione.

Example 3

Preparation of 4-[2-(4-chlorophenyl)-5-ethylthiazol-4-yl]-2,2,6,6-tetramethylpyran-3,5-dione (Compound T11 in Table T1)

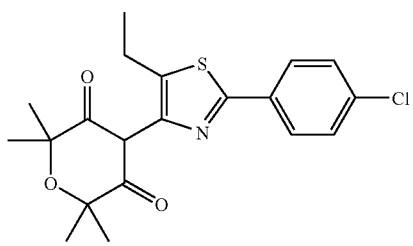 [SMILES: CCc1sc(-c2ccc(Cl)cc2)nc1C1C(=O)C(C)(C)OC(C)(C)C1=O]

Step 1

Preparation of 5-chloro-2,2,6,6-tetramethyl-6H-pyran-3-one

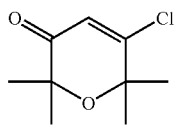

To a suspension of 2,2,6,6-tetramethylpyran-3,5-dione (741 mg, 4.35 mmol) in chloroform (10 ml) is added phosphorus pentachloride (454 mg, 2.18 mmol), and the reaction is heated to reflux for 5 hours. Silica gel is added to the cooled crude reaction mixture, the solvent is evaporated under reduced pressure and the residue is purified by flash chromatography on silica gel to give 5-chloro-2,2,6,6-tetramethyl-6H-pyran-3-one (349 mg).

Step 2

Preparation of 1-[2-(4-chlorophenyl)thiazol-5-yl]ethanol

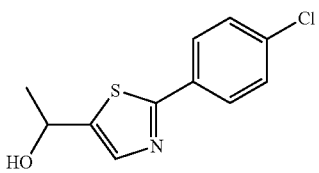

To a stirred solution of 1-[2-(4-chlorophenyl)thiazol-5-yl]ethanone (2.38 g, 10 mmol) in methanol (20 ml) at 0° C. is added sodium borohydride (379 mg, 10.5 mmol) in one portion. The resultant solution is allowed to warm to room temperature, and is then stirred at room temperature for 3 hours. The reaction is quenched with saturated aqueous ammonium chloride solution (200 ml) and extracted with chloroform (200 ml). The organic layer is dried over anhydrous magnesium sulfate and concentrated in vacuuo to give desired product as a brown solid (2.32 g)

Step 3

Preparation of 5-{1-[2-(4-chlorophenyl)thiazol-5-yl]ethoxy}-2,2,6,6-tetramethyl-6H-pyran-3-one

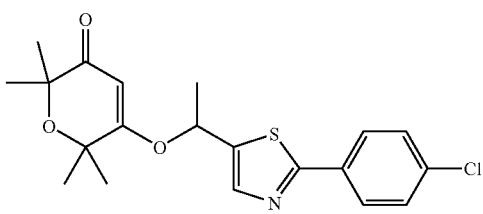 [SMILES: CC(OC1=CC(=O)C(C)(C)OC1(C)C)c1cnc(-c2ccc(Cl)cc2)s1]

To a solution of 1-[2-(4-chlorophenyl)thiazol-5-yl]ethanol (335 mg, 1.4 mmol) in anhydrous tetrahydrofuran (5 ml) under nitrogen is added sodium hydride, 60% dispersion in mineral oil, (48 mg, 1.2 mmol) and the resulting yellow suspension is allowed to stir at room temperature for 1 hour. A solution of 5-chloro-2,2,6,6-tetramethyl-6H-pyran-3-one (189 mg, 1 mmol) in anhydrous tetrahydrofuran (2 ml) is then added and reaction is allowed to stir at room temperature for 17 hours. The crude reaction mixture is purified by flash chromatography on silica gel to give 5-{1-[2-(4-chlorophenyl)thiazol-5-yl]ethoxy}-2,2,6,6-tetramethyl-6H-pyran-3-one (288 mg).

Step 4

Preparation of 4-[2-(4-chlorophenyl)-5-ethylthiazol-4-yl]-2,2,6,6-tetramethylpyran-3,5-dione

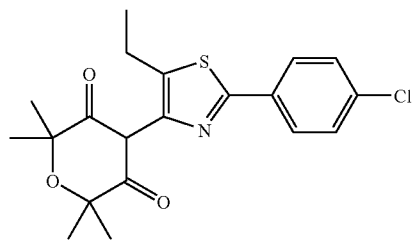 [SMILES: CCc1sc(-c2ccc(Cl)cc2)nc1C1C(=O)C(C)(C)OC(C)(C)C1=O]

To a solution of 5-{1-[2-(4-chlorophenyl)thiazol-5-yl]ethoxy}-2,2,6,6-tetramethyl-6H-pyran-3-one (270 mg, 0.69 mmol) in 1,2-dimethoxyethane (2 ml) is added 1-butyl-methyl imidazolium bis(trifluoromethylsulphonyl)imide (0.1 ml) and the solution heated to 210° C. for 30 minutes under microwave irradiation. The crude reaction mixture is purified by flash chromatography on silica gel to give 4-[2-(4-chlorophenyl)-5-ethylthiazol-4-yl]-2,2,6,6-tetramethylpyran-3,5-dione.

Example 4

Preparation of 5-[2-(4-chlorophenyl)-5-methylselenazol-4-yl]-2,2,6,6-tetramethylpyran-3,5-dione (Compound T16 in Table T1)

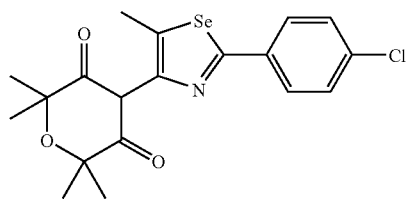 [SMILES: Cc1[se]c(-c2ccc(Cl)cc2)nc1C1C(=O)C(C)(C)OC(C)(C)C1=O]

Step 1

Preparation of 2-(4-chlorophenyl)selenazole-5-carbaldehyde

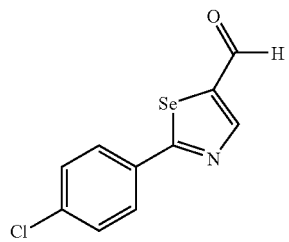 [SMILES: O=Cc1cnc(-c2ccc(Cl)cc2)[se]1]

To a suspension of 4-chloroselenobenzamide (219 mg, 1 mmol) and 2-chloromalonaldehyde (160 mg, 1.5 mmol) in 1,2-dimethoxyethane (1.5 ml) is added magnesium carbonate (42 mg, 0.5 mmol) and the resulting mixture is stirred at 60° C. under an atmosphere of nitrogen for 3 hours. The crude reaction mixture is then filtered through a plug of silica and washed with ethyl acetate, and filtrate is concentrated to give a brown solid. The crude product is purified by flash chromatography on silica gel to give 2-(4-chloro-phenyl)selenazole-5-carbaldehyde (162 mg).

Step 2

Preparation of [2-(4-chlorophenyl)selenazol-5-yl]methanol

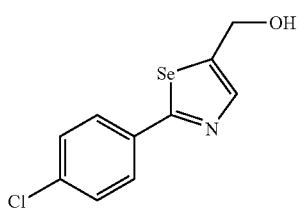 [SMILES: OCc1cnc(-c2ccc(Cl)cc2)[se]1]

To a suspension of 2-(4-chlorophenyl)selenazole-5-carbaldehyde (130 mg, 0.48 mmol) in methanol (5 ml) is added sodium borohydride (19 mg, 0.5 mmol) at 0° C. The reaction mixture is stirred at 0° C. for 0.5 h. The reaction mixture is quenched with aqueous saturated ammonium chloride solution (10 ml), and extracted with dichloromethane (3×25 ml). The combined organic extracts are dried over anhydrous magnesium sulfate, filtered and the filtrate is evaporated to dryness to give [2-(4-chlorophenyl)selenazol-5-yl]methanol (127 mg).

Step 3

Preparation of 5-[2-(4-chlorophenyl)selenazol-5-ylmethoxy]-2,2,6,6-tetramethyl-6H-pyran-3-one

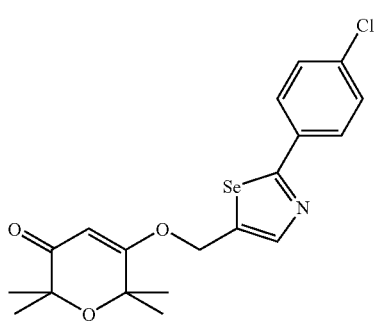 [SMILES: CC1(C)OC(C)(C)C(OCc2cnc(-c3ccc(Cl)cc3)[se]2)=CC1=O]

To a solution of [2-(4-chlorophenyl)selenazol-5-yl]methanol (300 mg, 1.1 mmol) in dry tetrahydrofuran (5 ml) under an atmosphere of nitrogen is added, in one portion, the sodium hydride (44 mg, 1.1 mmol). The reaction mixture is stirred for 5 minutes at room temperature and 5-chloro-2,2,6,6-tetramethyl-6H-pyran-3-one (208 mg, 1.1 mmol) is added in one portion. The reaction mixture is stirred at room temperature overnight. Silica gel is added to the crude reaction mixture, and the solvent is evaporated under reduced pressure. The residue is purified by flash chromatography on silica gel to give 5-[2-(4-chlorophenyl)selenazol-5-ylmethoxy]-2,2,6,6-tetramethyl-6H-pyran-3-one (261 mg).

Step 4

Preparation of 5-[2-(4-chlorophenyl)-5-methylselenazol-4-yl]-2,2,6,6-tetramethylpyran-3,5-dione

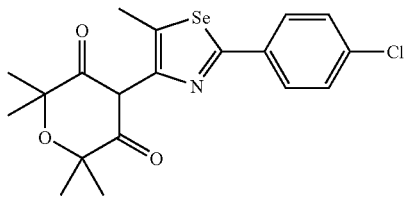 [SMILES: Cc1[se]c(-c2ccc(Cl)cc2)nc1C1C(=O)C(C)(C)OC(C)(C)C1=O]

5-[2-(4-chlorophenyl)selenazol-5-ylmethoxy]-2,2,6,6-tetramethyl-6H-pyran-3-one (239 mg, 0.56 mmol) is placed in a microwave vial and dissolved in diethylene glycol dimethyl ether (8 ml). 1-Butyl-3-methylimidazolium bis(trifluoromethylsulfonyl)imide (0.1 ml) is added and the reaction mixture is heated at 210° C. for 30 minutes under microwave irradiation. Silica gel is added to the crude reaction mixture, the solvent is evaporated under reduced pressure and the residue is purified by flash chromatography on silica gel to give 5-[2-(4-chlorophenyl)-5-methylselenazol-4-yl]-2,2,6,6-tetramethylpyran-3,5-dione.

Example 5

Preparation of 3-[2-(4-chloro-phenyl)-5-ethyl-thiazol-4-yl]-1-methyl-8-oxa-bicyclo[3.2.1]-octane-2,4-dione (Compound T50 in Table T1)

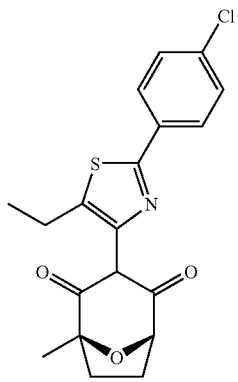 [SMILES: CCc1sc(-c2ccc(Cl)cc2)nc1C1C(=O)[C@@H]2CC[C@@](C)(O2)C1=O]

Step 1

Preparation of (1R*,5S*-2,3,4,4-tetrachloro-1-methyl-8-oxabicyclo[3.2.1]octa-2,6-diene

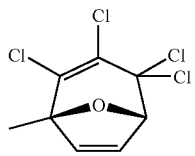

Pentachlorocyclopropane (100 g, 0.467 mol) is added to a suspension of potassium hydroxide (31.4 g, 0.56 mol) in 1,4-dioxane (3600 ml) and the mixture is stirred at room temperature for 30 minutes and then heated to 65° C. for a further 30 minutes. 2-Methylfuran (38.36 g, 0.467 mol) is added to the reaction mixture, the temperature is raised to 85-90° C. and the mixture is stirred for 16 hours. The reaction mixture is cooled to room temperature, filtered through a plug of diatomaceous earth and the filtrate evaporated in vacuo to give (1R*,5S*)-2,3,4,4-tetrachloro-1-methyl-8-oxabicyclo[3.2.1]octa-2,6-diene (83 g), used without further purification in the next step.

Step 2

Preparation of (1R*,5S*)-3,4-dichloro-5-methyl-8-oxabicyclo[3.2.1]octa-3,6-dien-2-one

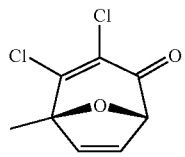

Silver nitrate (166 g, 0.982 mol) is added to a stirred mixture of (1R*,5S*)-2,3,4,4-tetrachloro-1-methyl-8-oxabicyclo[3.2.1]octa-2,6-diene (83 g, 0.491 mol), acetone (1500 ml) and water (1500 ml) and the mixture is heated at 65° C. for 16 hours. The reaction mixture is cooled to room temperature, and a saturated solution of aqueous sodium bicarbonate is added to adjust the pH to 7-8. The mixture is filtered through a plug of diatomaceous earth, and the filtrate is concentrated in vacuo to remove most of the acetone. The aqueous mixture is extracted with ethyl acetate (3×500 ml) and the organic extracts are combined, dried over anhydrous sodium sulfate, filtered and the filtrate is evaporated. The residue is purified by flash column chromatography on silica gel to give (1R*, 5S*)-3,4-dichloro-5-methyl-8-oxabicyclo[3.2.1]octa-3,6-dien-2-one (29.5 g) as a yellow oil.

Step 3

Preparation of 3-chloro-1-methyl-4-oxo-spiro(1,3-dioxolane-2,2'-[8]oxa-bicyclo[3.2.1]oct-6-ene)

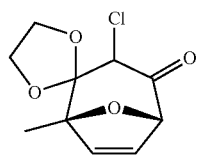

Sodium (4.41 g, 0.204 mol) is added cautiously to ethylene glycol (99.75 g) and the mixture is stirred at 35-40° C. under an atmosphere of nitrogen until the sodium is completely dissolved. A solution of (1R*,5S*)-3,4-dichloro-5-methyl-8-oxabicyclo[3.2.1]octa-3,6-dien-2-one (28 g, 0.136 mol) in tetrahydrofuran (200 ml) is added dropwise over 30 minutes, and once the addition is complete, the mixture is stirred for 90 minutes at room temperature. The reaction mixture is neutralised by addition of 10% aqueous sodium dihydrogen phosphate, and extracted with ethyl acetate (3×100 ml). The organic extracts are combined, dried over anhydrous sodium sulfate, filtered and the filtrate is evaporated. The residue is purified by flash column chromatography on silica gel to give 3-chloro-1-methyl-4-oxo-spiro(1,3-dioxolane-2,2'-[8]oxabicyclo[3.2.1]oct-6-ene) (24.5 g) as a gum.

Step 4

Preparation of (1R*,5S*)-1-methyl-4-oxo-spiro(1,3-dioxolane-2,2'-[8]-oxa-bicyclo[3.2.1]oct-6-ene)

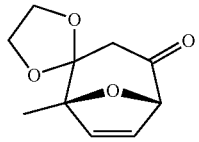

Zinc powder (13.88 g, 0.212 mol) is added to a solution of 3-chloro-1-methyl-4-oxo-spiro(1,3-dioxolane-2,2'-[8]oxabicyclo[3.2.1]oct-6-ene) (24.5 g, 0.016 mol) in acetic acid (122.5 ml) and the reaction mixture stirred at room temperature for 24 hours. The mixture is diluted with water (612.5 ml) and extracted with ethyl acetate (3×150 ml). The organic extracts are combined, dried over anhydrous sodium sulfate, filtered and the filtrate is evaporated to give (1R*,5S*)-1-methyl-4-oxo-spiro(1,3-dioxolane-2,2'-[8]oxabicyclo[3.2.1] oct-6-ene) (20 g) as a yellow oil, used without further purification in the next step.

Step 5

Preparation of (1R*,5S*)-1-methyl-8-oxabicyclo [3.2.1]oct-6-ene-2,4-dione

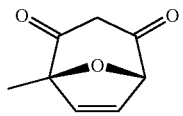

Hydrochloric acid (50 ml) is added, in three portions, to a mixture of (1R*,5S*)-1-methyl-4-oxo-spiro(1,3-dioxolane-2,2'-[8]oxabicyclo[3.2.1]oct-6-ene) (20 g, 0.102 mol) in acetone (500 ml) and water (250 ml) and the reaction mixture is stirred at 65-70° C. for 48 hrs. The mixture is cooled to room temperature, most of the acetone is removed by evaporation under reduced pressure and the resulting aqueous solution is extracted with ethyl acetate (3×100 ml). The organic extracts are combined, dried over anhydrous sodium sulfate, filtered and the filtrate is evaporated. The residue is purified by flash column chromatography on silica gel to give (1R*, 5S*)-1-methyl-8-oxabicyclo[3.2.1]oct-6-ene-2,4-dione (10.0 g) as a yellow oil.

Step 6

Preparation of (1R*,5S*)-1-methyl-8-oxabicyclo [3.2.1]octane-2,4-dione

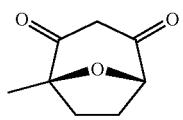

To a solution of (1R*,5S*)-1-methyl-8-oxabicyclo[3.2.1] oct-6-ene-2,4-dione (12.0 g, 0.079 mol) in ethyl acetate (100 ml) is added 10% palladium on carbon (2.4 g), followed by stirring under a 1 bar hydrogen atmosphere for 24 hours. The reaction mixture is then filtered through diatomaceous earth and concentrated to give a crude product which is purified by flash chromatography (hexane/ethyl acetate) to afford (1R*, 5S*)-1-methyl-8-oxabicyclo[3.2.1]octane-2,4-dione (6.90 g) as pale yellow solid.

Step 7

Preparation of 4-chloro-1-methyl-8-oxa-bicyclo [3.2.1]oct-3-en-2-one

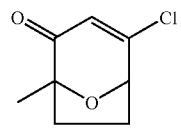

To a solution of 1-methyl-8-oxa-bicyclo[3.2.1]octane-2,4-dione (175 mg, 1.14 mmol) in chloroform (2 ml) is added, under $N_2$, in one portion, the phosphorous pentachloride (135 mg, 0.65 mmol). The reaction mixture is stirred for reflux for 5 hours. Silica gel is added to the cooled crude reaction mixture, the solvent is evaporated under reduced pressure and the residue is purified by flash chromatography on silica gel to give 4-chloro-1-methyl-8-oxa-bicyclo[3.2.1]oct-3-en-2-one (93 mg).

Step 8

Preparation of 4-{1-[2-(4-chlorophenyl)thiazol-5-yl] ethoxy}-1-methyl-8-oxabicyclo[3.2.1]oct-3-en-2-one

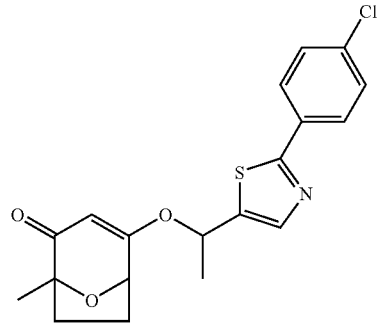 [SMILES: CC(OC1=CC(=O)C2(C)CCC1O2)c1cnc(-c2ccc(Cl)cc2)s1]

To a solution of 1-[2-(4-Chlorophenyl)thiazol-5-yl]ethanol (129 mg, 0.54 mmol) and 4-chloro-1-methyl-8-oxabicyclo[3.2.1]oct-3-en-2-one (93 mg, 0.54 mmol) in dry THF (5 ml) is added in one portion the sodium hydride, 60% dispersion in mineral oil, (21 mg, 0.54 mmol). The reaction mixture is stirred at room temperature overnight. Silica gel is added to the crude reaction mixture, and the solvent is evaporated under reduced pressure. The residue is purified by flash chromatography on silica gel to give 4-{1-[2-(4-Chlorophenyl) thiazol-5-yl]-ethoxy}-1-methyl-8-oxabicyclo[3.2.1]oct-3-en-2-one (160 mg).

Step 9

Preparation of 3-[2-(4-chlorophenyl)-5-ethylthiazol-4-yl]-1-methyl-8-oxabicyclo[3.2.1]octane-2,4-dione

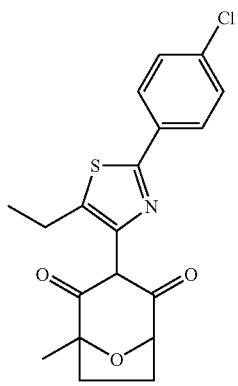 [SMILES: CCc1sc(-c2ccc(Cl)cc2)nc1C1C(=O)C2CCC(C)(O2)C1=O]

4-{1-[2-(4-chlorophenyl)thiazol-5-yl]ethoxy}-1-methyl-8-oxabicyclo[3.2.1]oct-3-en-2-one (160 mg, 0.42 mmol) is placed in a microwave vial and dissolved in diethylene glycol dimethyl ether (5 ml). 1-Butyl-3-methylimidazolium bis(trifluoromethylsulfonyl)imide (0.1 ml) is added and the reaction mixture is heated at 230° C. for 30 minutes under microwave irradiation. Silica gel is added to the crude reaction mixture, the solvent is evaporated under reduced pressure and the residue is purified by flash chromatography on silica gel to give 3-[2-(4-chlorophenyl)-5-ethylthiazol-4-yl]-1-methyl-8-oxabicyclo[3.2.1]octane-2,4-dione.

Example 6

Preparation of 4-[2-(4-chlorophenyl)-5-methylthiazol-4-yl]-2,2,6,6-tetramethylthiopyran-3,5-dione (Compound T81 in Table T1)

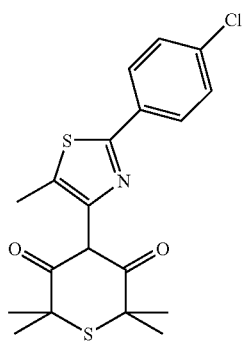

Step 1

Preparation of [2-(4-chlorophenyl)thiazol-5-yl]methanol

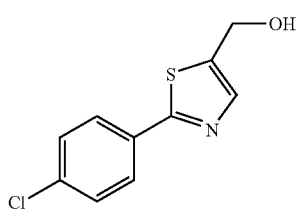 [SMILES: OCc1cnc(-c2ccc(Cl)cc2)s1]

To a suspension of 2-(4-chlorophenyl)thiazole-5-carbaldehyde (3.26 g, 14.6 mmol) in methanol (50 ml) is added the sodium borohydride (568 mg, 15 mmol) portionwise at room temperature. The reaction mixture is stirred at room temperature for 2 h. The reaction mixture is quenched with 50 ml of an aqueous saturated solution of ammonium chloride, extracted with dichloromethane (2×100 ml). The combined organic extracts are dried with magnesium sulphate, filtered and evaporated to dryness to give [2-(4-chlorophenyl)thiazol-5-yl]methanol (3.24 g).

Step 2

Preparation of 5-chloromethyl-2-(4-chlorophenyl)thiazole

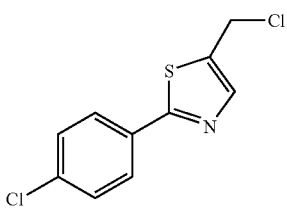 [SMILES: ClCc1cnc(-c2ccc(Cl)cc2)s1]

To a suspension of [2-(4-chlorophenyl)thiazol-5-yl]methanol (3.24 g, 14.3 mmol) in dichloromethane (40 ml) is added dropwise the thionyl chloride (1.3 ml, 18 mmol) at room temperature under nitrogen. The reaction mixture is stirred at room temperature for 4 hours. Silica gel is added to the crude reaction mixture, the solvent is evaporated under reduced pressure and the residue is purified by flash chromatography on silica gel to give 5-chloromethyl-2-(4-chlorophenyl)thiazole (3.24 g)

Step 3

Preparation of 5-[2-(4-chlorophenyl)thiazol-4-ylmethoxy]-2,2,6,6-tetramethyl-6H-thiopyran-3-one

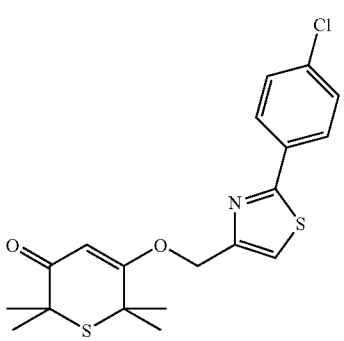 [SMILES: CC1(C)SC(C)(C)C(OCc2csc(-c3ccc(Cl)cc3)n2)=CC1=O]

To a suspension of 2,2,6,6-tetramethylthiopyran-3,5-dione (745 mg, 4 mmol) in acetone (30 ml) is added the potassium carbonate (2.07 g, 15 mmol) in one portion. The reaction mixture is stirred at room temperature for 5 minutes and the 2-chloro-5-chloromethylthiazole (977 mg, 4 mmol) is added in one portion. The reaction mixture is therefore heated to reflux overnight. The cooled reaction mixture is diluted with 50 ml of 2N aq. NaOH, 50 ml of water and extracted with EtOAc (3×75 ml). The combined organic layers are dried over magnesium sulphate, filtered and evaporated under reduced pressure. The crude product is purified by flash chromatography to give 5-[2-(4-chlorophenyl)thiazol-4-ylmethoxy]-2,2,6,6-tetramethyl-6H-thiopyran-3-one (461 mg).

Step 4

Preparation of 4-[2-(4-chlorophenyl)-5-methylthiazol-4-yl]-2,2,6,6-tetramethylthiopyran-3,5-dione

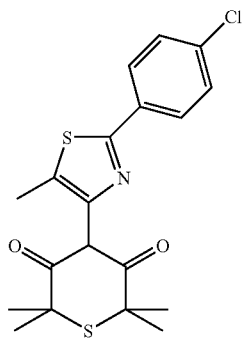 [SMILES: Cc1sc(-c2ccc(Cl)cc2)nc1C1C(=O)C(C)(C)SC(C)(C)C1=O]

5-[2-(4-Chlorophenyl)thiazol-4-ylmethoxy]-2,2,6,6-tetramethyl-6H-thiopyran-3-one (450 mg, 1.14 mmol) is placed in a microwave vial and dissolved in diethylene glycol dimethyl ether (15 ml). 1-Butyl-3-methylimidazolium bis(trifluoromethylsulfonyl)imide (0.1 ml) is added and the reaction mixture is heated at 230° C. for 30 minutes under microwave irradiation. Silica gel is added to the crude reaction mixture, the solvent is evaporated under reduced pressure and the residue is purified by flash chromatography on silica gel to give 4-[2-(4-chlorophenyl)-5-methylthiazol-4-yl]-2,2,6,6-tetramethylthiopyran-3,5-dione.

Example 7

Preparation of 4-[2-(4-chlorophenyl)-5-methylpyrimidin-4-yl]-2,2,6,6-tetramethylpyran-3,5-dione (Compound T71 in Table T1)

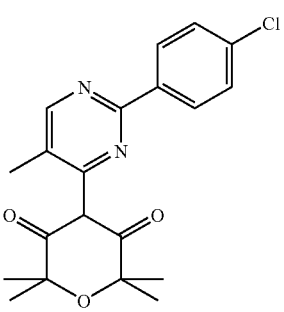

A microwave vial is charged with 4-chloro-2-(4-chlorophenyl)-5-methylpyrimidine (239 mg, 1 mmol), 2,2,6,6-tetramethyl-pyran-3,5-dione (170 mg, 1 mmol), palladium acetate (12 mg, 0.05 mmol), X-Phos (48 mg, 0.1 mmol) and potassium phosphate (424 mg, 2 mmol). 1,2-dimethoxyethane (3 ml) is added and the reaction heated to 150° C., with stirring, for 30 minutes. Silica gel is added to the crude reaction mixture, the solvent is evaporated under reduced pressure and the residue is purified by flash chromatography on silica gel to give 4-[2-(4-chlorophenyl)-5-methylpyrimidin-4-yl]-2,2,6,6-tetramethylpyran-3,5-dione.

Additional compounds in Table T1 below are prepared by similar methods using appropriate starting materials.

Where more than one tautomer or rotational conformer is observed in the proton NMR spectrum, the data shown below are for the mixture of isomers and conformers.

TABLE T1

| Compound Number | Structure | $^1$H nmr (CDCl$_3$ unless stated) or other physical data |
|---|---|---|
| T1 | 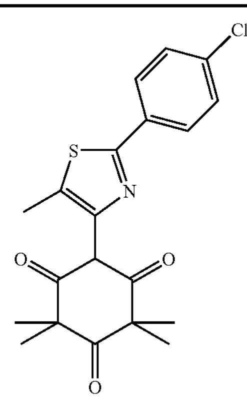 | δ ppm 1.50 (s, 12H) 2.33 (s, 3H) 7.43 (m, 2H) 7.77 (mult, 2H) |
| T2 | 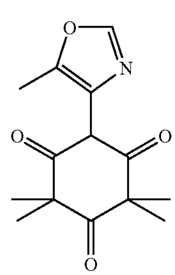 | δ ppm 1.39 (s, 6H) 1.52 (s, 6H) 2.49 (s, 3H) 8.08 (s (br), 1H) 8.30 (s, 1H) |

TABLE T1-continued

| Compound Number | Structure | $^1$H nmr (CDCl$_3$ unless stated) or other physical data |
|---|---|---|
| T3 | 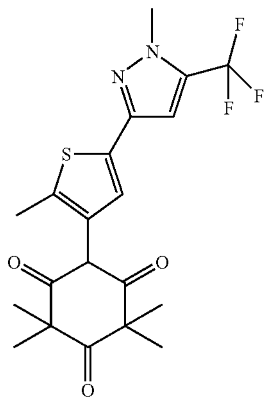 [SMILES: Cc1sc(-c2cc(C(F)(F)F)n(C)n2)cc1C1C(=O)C(C)(C)C(=O)C(C)(C)C1=O] | δ ppm 1.43 (s, 6H) 1.54 (s, 6H) 2.29 (s, 3H) 3.99 (s, 3H) 6.11 (s, 1H) 6.75 (s, 1H) 7.03 (s, 1H) |
| T4 | 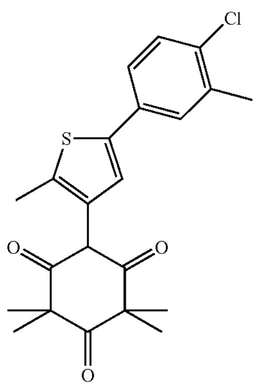 | δ ppm 1.44 (s, 6H) 1.55 (s, 6H) 2.29 (s, 3H) 2.39 (s, 3H) 7.00 (s, 1H) 7.31 (m, 2H) 7.41 (m, 1H) |
| T5 | 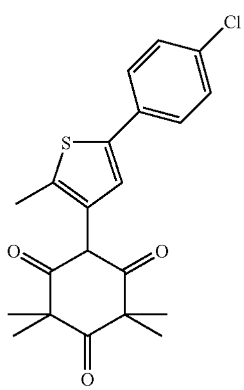 [SMILES: Cc1sc(-c2ccc(Cl)cc2)cc1C1C(=O)C(C)(C)C(=O)C(C)(C)C1=O] | δ ppm 1.44 (s, 6H) 1.55 (s, 6H) 2.30 (s, 3H) 6.11 (s, 1H) 7.01 (s, 1H) 7.33 (m, 2H) 7.47 (m, 2H) |
| T6 | 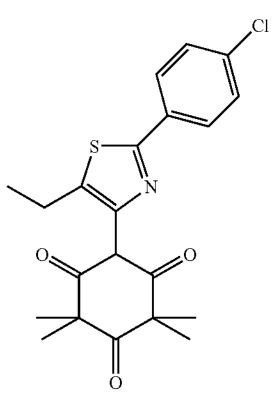 [SMILES: CCc1sc(-c2ccc(Cl)cc2)nc1C1C(=O)C(C)(C)C(=O)C(C)(C)C1=O] | δ ppm 1.33 (t, 3H) 1.50 (s, 12H) 2.71 (q, 2H) 7.44 (m, 2H) 7.80 (m, 2H) |

TABLE T1-continued

| Compound Number | Structure | ¹H nmr (CDCl₃ unless stated) or other physical data |
|---|---|---|
| T7 | 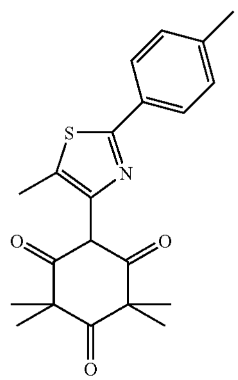 | δ ppm 1.50 (s, 12H), 2.32 (s, 3H), 2.41 (s, 3H), 7.26 (d, 2H), 7.73 (d, 2H) |
| T8 | 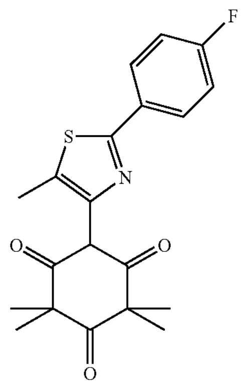 [SMILES: Cc1sc(-c2ccc(F)cc2)nc1C1C(=O)C(C)(C)C(=O)C(C)(C)C1=O] | δ ppm 1.50 (s, 12H), 2.32 (s, 3H), 7.15 (m, 2H), 7.83 (m, 2H) |
| T9 | 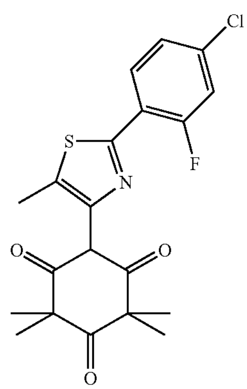 [SMILES: Cc1sc(-c2ccc(Cl)cc2F)nc1C1C(=O)C(C)(C)C(=O)C(C)(C)C1=O] | δ ppm 1.50 (s, 12H) 2.35 (s, 3H) 7.28-7.26 (m, 2H) 7.99 (m, 1H) 13.40 (s (br), 1H) |
| T10 | 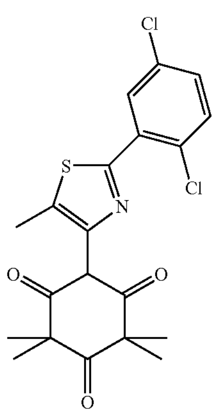 [SMILES: Cc1sc(-c2cc(Cl)ccc2Cl)nc1C1C(=O)C(C)(C)C(=O)C(C)(C)C1=O] | δ ppm 1.51 (s, 12H) 2.36 (s, 3H) 7.34 (dd, 1H) 7.46 (d, 1H) 7.95 (d, 1H) 13.11 (s (br), 1H) |

TABLE T1-continued

| Compound Number | Structure | ¹H nmr (CDCl₃ unless stated) or other physical data |
|---|---|---|
| T11 | 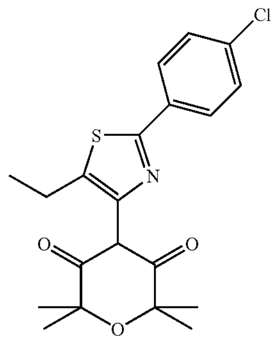 [SMILES: CCc1sc(-c2ccc(Cl)cc2)nc1C1C(=O)C(C)(C)OC(C)(C)C1=O] | δ ppm 1.33 (t, 3H) 1.56 (s, 12H) 2.82 (q, 2H) 7.42 (m, 2H) 7.78 (m, 2H) |
| T12 | 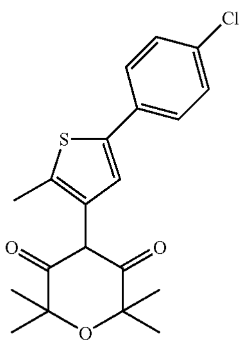 [SMILES: Cc1sc(-c2ccc(Cl)cc2)cc1C1C(=O)C(C)(C)OC(C)(C)C1=O] | δ ppm 1.53 (s, 6H) 1.65 (s, 6H) 2.34 (s, 3H) 5.96 (s, 1H) 7.06 (s, 1H) 7.37 (m, 2H) 7.52 (m, 2H) |
| T13 | 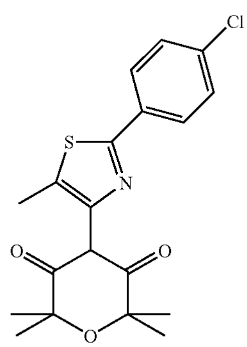 [SMILES: Cc1sc(-c2ccc(Cl)cc2)nc1C1C(=O)C(C)(C)OC(C)(C)C1=O] | δ ppm 1.56 (s, 12H) 2.41 (s, 3H) 7.42 (m, 2H) 7.76 (m, 2H) |
| T14 | 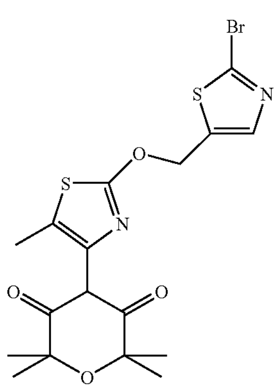 [SMILES: Cc1sc(OCc2cnc(Br)s2)nc1C1C(=O)C(C)(C)OC(C)(C)C1=O] | δ ppm 1.37 (s, 3H) 1.42 (s, 6H) 1.51 (s, 3H) 1.92 (s, 3H) 3.66 (dd, 1H) 4.49 (dd, 1H) 7.39 (s, 1H) |

TABLE T1-continued

| Compound Number | Structure | ¹H nmr (CDCl₃ unless stated) or other physical data |
|---|---|---|
| T15 | 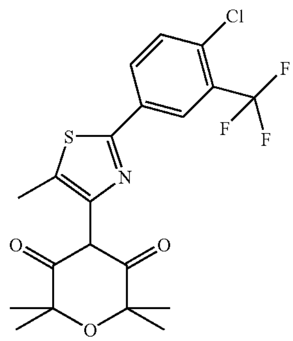 [SMILES: Cc1sc(-c2ccc(Cl)c(C(F)(F)F)c2)nc1C1C(=O)C(C)(C)OC(C)(C)C1=O] | δ ppm 1.55 (s (br), 12H) 2.42 (s, 3H) 7.60 (dd, 1H) 7.93 (dd, 1H) 8.11 (d, 1H) |
| T16 | 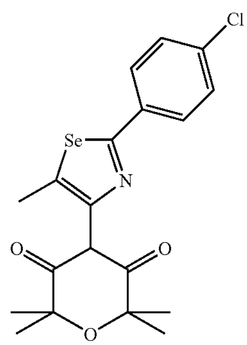 [SMILES: Cc1[se]c(-c2ccc(Cl)cc2)nc1C1C(=O)C(C)(C)OC(C)(C)C1=O] | δ ppm 1.56 (s, 12H) 2.45 (s, 3H) 7.21 (m, 2H) 7.41 (m, 2H) |
| T17 | 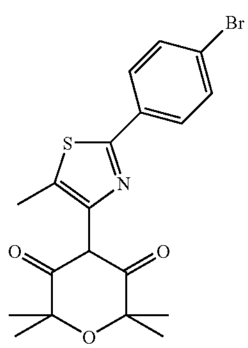 [SMILES: Cc1sc(-c2ccc(Br)cc2)nc1C1C(=O)C(C)(C)OC(C)(C)C1=O] | δ ppm 1.56 (s, 12H) 2.40 (s, 3H) 7.58 (m, 2H) 7.70 (m, 2H) |
| T18 | 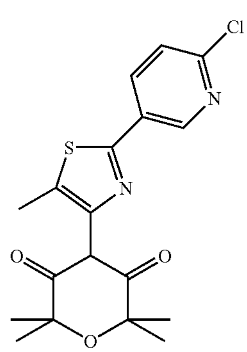 | δ ppm 1.56 (s (br), 12H) 2.42 (s, 3H) 7.43 (d, 1H) 8.08 (dd, 1H) 8.83 (d 1H) |

TABLE T1-continued
| Compound Number | Structure | $^1$H nmr (CDCl$_3$ unless stated) or other physical data |
|---|---|---|
| T19 | 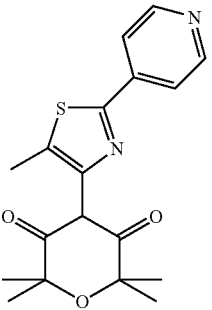 [SMILES: Cc1sc(-c2ccncc2)nc1C1C(=O)C(C)(C)OC(C)(C)C1=O] | δ ppm 1.57 (s, 12H) 2.45 (s, 3H) 7.69 (m, 2H) 8.72 (m, 2H) |
| T20 | 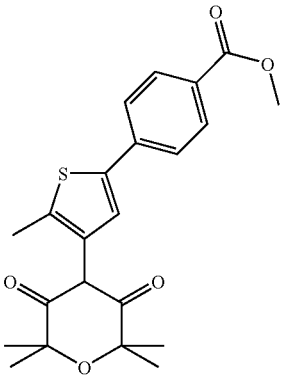 | δ ppm 1.49 (s (br), 6H) 1.61 (s (br), 6H) 2.31 (s, 3H) 3.92 (s, 3H) 7.15 (s, 1H) 7.61 (m, 2H) 8.02 (m, 2H) |
| T21 | 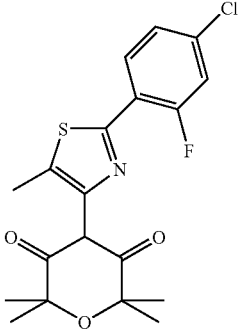 [SMILES: Cc1sc(-c2ccc(Cl)cc2F)nc1C1C(=O)C(C)(C)OC(C)(C)C1=O] | δ ppm 1.56 (s, 12H) 2.43 (s, 3H) 7.26 (m, 2H) 7.96 (m, 1H) |
| T22 | 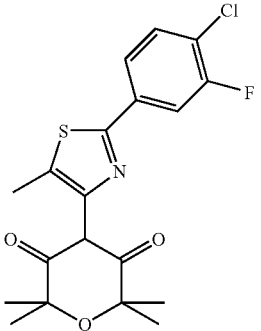 [SMILES: Cc1sc(-c2ccc(Cl)c(F)c2)nc1C1C(=O)C(C)(C)OC(C)(C)C1=O] | δ ppm 1.53-1.61 (m, 12H) 2.41 (s, 3H) 7.47 (m, 1H) 7.55 (m, 1H) 7.62 (m, 1H) |

TABLE T1-continued

| Compound Number | Structure | ¹H nmr (CDCl₃ unless stated) or other physical data |
|---|---|---|
| T23 | 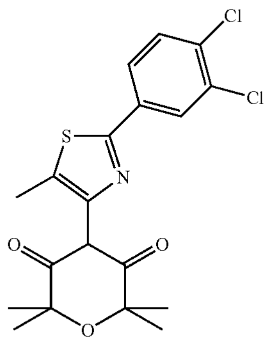 [SMILES: Cc1sc(-c2ccc(Cl)c(Cl)c2)nc1C1C(=O)C(C)(C)OC(C)(C)C1=O] | δ ppm 1.56 (s, 12H) 2.41 (s, 3H) 7.52 (d, 1H) 7.65 (dd, 1H) 7.91 (d, 1H) |
| T24 | 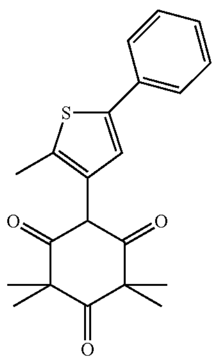 [SMILES: Cc1sc(-c2ccccc2)cc1C1C(=O)C(C)(C)C(=O)C(C)(C)C1=O] | δ ppm 1.49 (s, 6H) 1.60 (s, 6H) 2.34 (s, 3H) 6.31 (s, br, 1H) 7.06 (m, 1H) 7.31 (s, 1H) 7.41 (m, 2H) 7.59 (m, 2H) |
| T25 | 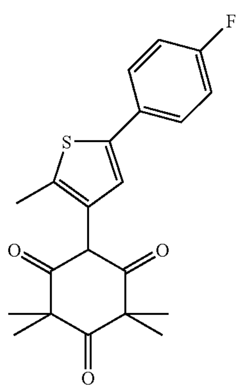 [SMILES: Cc1sc(-c2ccc(F)cc2)cc1C1C(=O)C(C)(C)C(=O)C(C)(C)C1=O] | δ ppm 1.44 (s, 6H) 1.57 (s, 6H) 2.29 (s, 3H) 6.21 (s, br, 1H) 6.95 (s, 1H) 7.07 (m, 2H) 7.51 (m, 2H) |
| T26 | 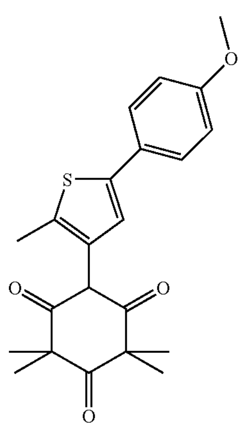 [SMILES: COc1ccc(-c2cc(C3C(=O)C(C)(C)C(=O)C(C)(C)C3=O)c(C)s2)cc1] | δ ppm 1.44 (s, 6H) 1.55 (s, 6H) 2.28 (s, 3H) 3.83 (s, 3H) 6.27 (s, br, 1H) 6.89 (d, 2H) 6.90 (s, 1H) 7.48 (d, 2H) |

TABLE T1-continued

| Compound Number | Structure | ¹H nmr (CDCl₃ unless stated) or other physical data |
|---|---|---|
| T27 | 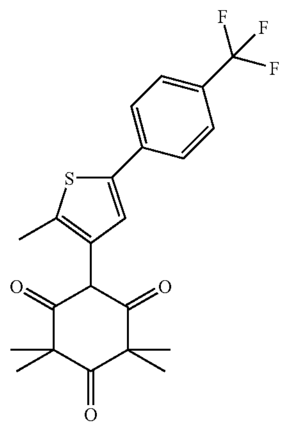 [SMILES: Cc1sc(-c2ccc(C(F)(F)F)cc2)cc1C1C(=O)C(C)(C)C(=O)C(C)(C)C1=O] | δ ppm 1.51 (s (br), 12H) 2.32 (s, 3H) 7.12 (s, 1H) 7.63 (m, 4H) |
| T28 | 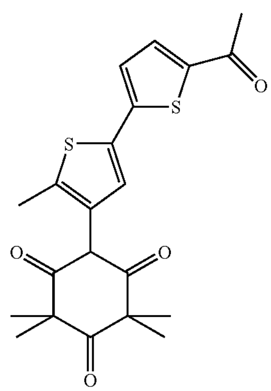 [SMILES: CC(=O)c1ccc(-c2cc(C3C(=O)C(C)(C)C(=O)C(C)(C)C3=O)c(C)s2)s1] | δ ppm 1.44 (s, 6H) 1.56 (s, 6H) 2.30 (s, 3H) 2.54 (s, 3H) 7.04 (s, 1H) 7.12 (d, 1H) 7.57 (d, 1H) |
| T29 | 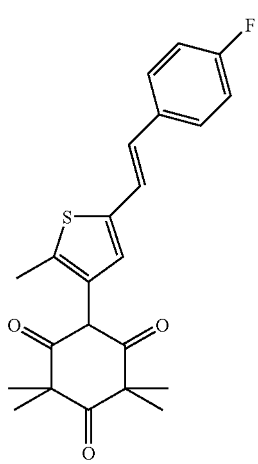 [SMILES: Cc1sc(/C=C/c2ccc(F)cc2)cc1C1C(=O)C(C)(C)C(=O)C(C)(C)C1=O] | δ ppm 1.43 (s, 6H) 1.54 (s, 6H) 2.27 (s, 3H) 6.19 (s, 1H) 6.79 (m, 2H) 6.93 (m, 3H) 7.35-7.45 (m, 2H) |

TABLE T1-continued
| Compound Number | Structure | $^1$H nmr (CDCl$_3$ unless stated) or other physical data |
|---|---|---|
| T30 | 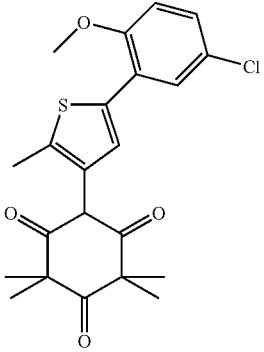 [SMILES: COc1ccc(Cl)cc1-c1cc(C2C(=O)C(C)(C)C(=O)C(C)(C)C2=O)c(C)s1] | δ ppm 1.50 (s, 12H) 2.29 (s, 3H) 3.91 (s, 3H) 6.89 (m, 2H) 7.18 (m, 1H) 7.57 (d, 1H) |
| T31 | 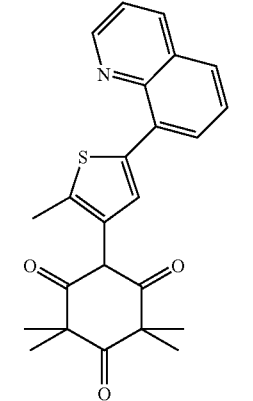 [SMILES: Cc1sc(-c2cccc3cccnc23)cc1C1C(=O)C(C)(C)C(=O)C(C)(C)C1=O] | δ ppm 1.46 (s, 6H) 1.54 (s, 6H) 2.33 (s, 3H) 6.99 (s, 1H) 7.95 (m, 2H) 8.15 (m, 2H) 8.91 (m, 1H) 9.50 (m, 1H) |
| T32 | 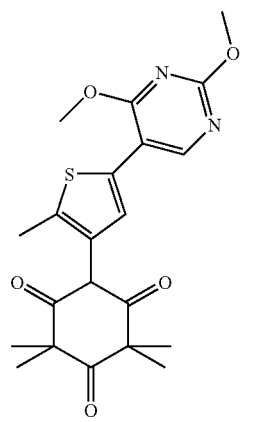 [SMILES: COc1ncc(-c2cc(C3C(=O)C(C)(C)C(=O)C(C)(C)C3=O)c(C)s2)c(OC)n1] | δ ppm 1.50 (s, 12H) 2.30 (s, 3H) 4.07 (s, 3H) 4.14 (s, 3H) 7.14 (s, 1H) 8.53 (s, 1H) |
| T33 | 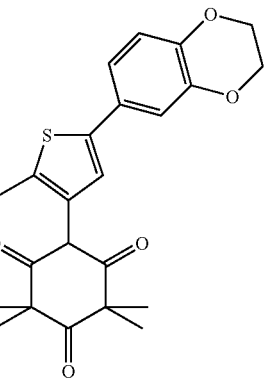 | δ ppm 1.44 (s, 6H) 1.54 (s, 6H) 2.27 (s, 3H) 4.28 (m, 4H) 6.22 (s, 1H) 6.86 (m, 2H) 7.03 (m, 2H) |

TABLE T1-continued
| Compound Number | Structure | ¹H nmr (CDCl₃ unless stated) or other physical data |
|---|---|---|
| T34 | 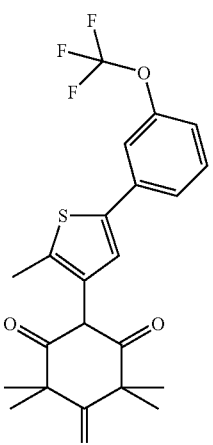 | δ ppm 1.42 (s, 6H) 1.50 (s, 6H) 2.31 (s, 3H) 6.88 (m, 1H) 7.05 (s, 1H) 7.13 (m, 1H) 7.38 (m, 1H) 7.46 (m, 1H) |
| T35 | 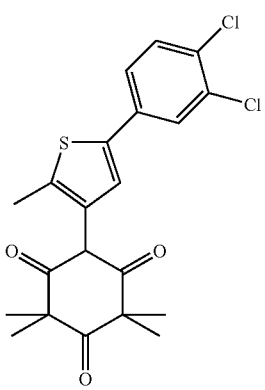 [SMILES: Cc1sc(-c2ccc(Cl)c(Cl)c2)cc1C1C(=O)C(C)(C)C(=O)C(C)(C)C1=O] | δ ppm 1.44 (s, 6H) 1.56 (s, 6H) 2.30 (s, 3H) 6.16 (s, br, 1H) 7.03 (s, 1H) 7.36 (dd, 1H) 7.43 (d, 1H) 7.63 (d, 1H) |
| T36 | 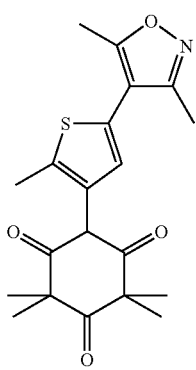 | δ ppm 1.44 (s, 6H) 1.56 (s, 6H) 2.31 (s, 3H) 2.36 (s, 3H) 2.51 (s, 3H) 6.18 (s (br), 1H) 6.73 (s, 1H) |

TABLE T1-continued

| Compound Number | Structure | ¹H nmr (CDCl₃ unless stated) or other physical data |
|---|---|---|
| T37 | 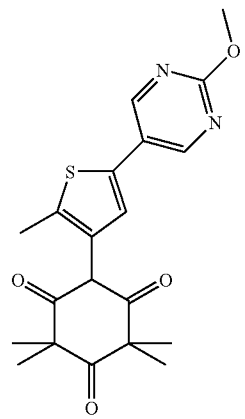 [SMILES: COc1ncc(-c2cc(C3C(=O)C(C)(C)C(=O)C(C)(C)C3=O)c(C)s2)cn1] | δ ppm 1.45 (s, 6H) 1.59 (s, 6H) 2.29 (s, 3H) 4.04 (s, 3H) 7.00 (s, 1H) 8.45 (s, 2H) |
| T38 | 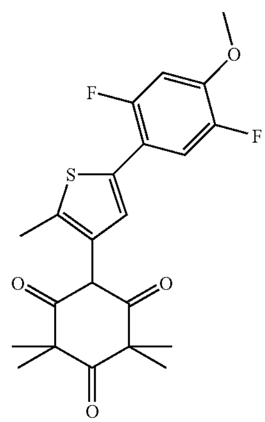 [SMILES: COc1cc(F)c(-c2cc(C3C(=O)C(C)(C)C(=O)C(C)(C)C3=O)c(C)s2)cc1F] | δ ppm 1.44 (s, 6H) 1.55 (s, 6H) 2.29 (s, 3H) 3.90 (s, 3H) 6.20 (s, br, 1H) 6.76 (dd, 1H) 7.06 (s, 1H) 7.28 (dd, 1H) |
| T39 | 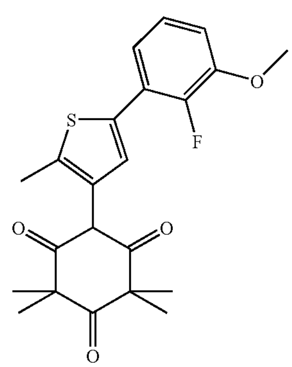 | δ ppm 1.44 (s, 6H) 1.55 (s, 6H) 2.31 (s, 3H) 3.92 (s, 3H) 6.23 (s (br), 1H) 6.88 (m, 1H) 7.06 (m, 1H) 7.15 (m, 1H) 7.17 (s, 1H) |
| T40 | 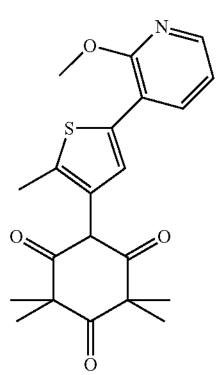 [SMILES: COc1ncccc1-c1cc(C2C(=O)C(C)(C)C(=O)C(C)(C)C2=O)c(C)s1] | δ ppm 1.45 (s, 6H) 1.55 (s, 6H) 2.30 (s, 3H) 4.07 (s, 3H) 6.94 (dd, 1H) 7.25 (s, 1H) 7.85 (dd, 1H) 8.09 (dd, 1H) |

TABLE T1-continued

| Compound Number | Structure | $^1$H nmr (CDCl$_3$ unless stated) or other physical data |
|---|---|---|
| T41 | 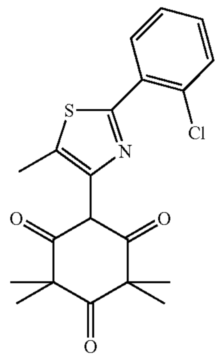 [SMILES: Cc1sc(-c2ccccc2Cl)nc1C1C(=O)C(C)(C)C(=O)C(C)(C)C1=O] | δ ppm 1.50 (s, 12H) 2.38 (s, 3H) 5.2 (s, 1H) 7.4 (m, 2H) 7.5 (m, 1H); 7.95 (m, 1H) |
| T42 | 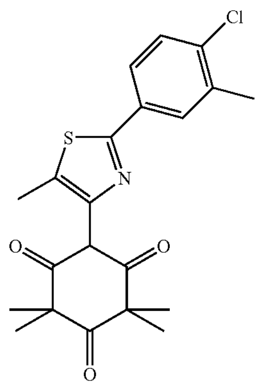 | δ ppm 1.50 (s, 12H) 2.34 (s, 3H) 2.54 (s, 3H) 7.4 (d, 1H) 7.6 (d, 1H) 7.7 (s, 1H) |
| T43 | 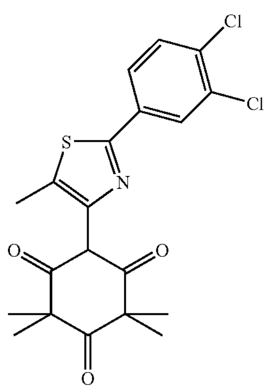 [SMILES: Cc1sc(-c2ccc(Cl)c(Cl)c2)nc1C1C(=O)C(C)(C)C(=O)C(C)(C)C1=O] | δ ppm 1.50 (s, 12H) 2.35 (s, 3H) 7.5 (d, 1H) 7.65 (d, 1H) 7.9 (s, 1H) |
| T44 | 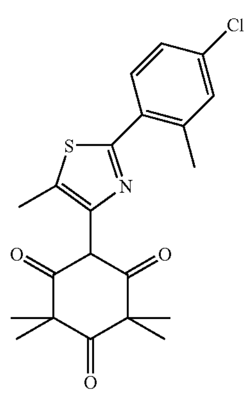 [SMILES: Cc1cc(Cl)ccc1-c1nc(C2C(=O)C(C)(C)C(=O)C(C)(C)C2=O)c(C)s1] | δ ppm 1.50 (s, 12H) 2.35 (s, 3H) 2.55 (s, 3H) 7.26 (d, 1H) 7.3 (s, 1H) 7.6 (d, 1H) |

TABLE T1-continued

| Compound Number | Structure | ¹H nmr (CDCl₃ unless stated) or other physical data |
| --- | --- | --- |
| T45 | 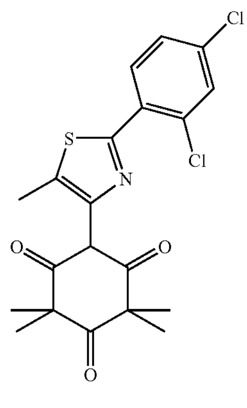 | δ ppm 1.50 (s, 12H) 2.35 (s, 3H) 7.35 (dd, 1H) 7.52 (d, 1H) 7.9 (d, 1H) |
| T46 | 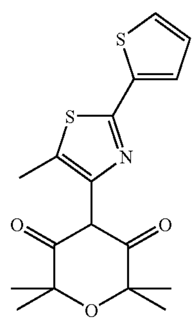 [SMILES: Cc1sc(-c2cccs2)nc1C1C(=O)C(C)(C)OC(C)(C)C1=O] | δ ppm 1.55 (s, 12H) 2.37 (s, 3H) 7.09 (dd, 1H) 7.40 (d, 1H) 7.46 (d, 1H) |
| T47 | 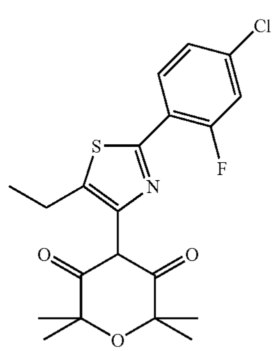 [SMILES: CCc1sc(-c2ccc(Cl)cc2F)nc1C1C(=O)C(C)(C)OC(C)(C)C1=O] | δ ppm 1.39 (t, 3H) 1.61 (5, 12H) 2.90 (q, 2H) 7.29 (m, 2H) 8.01 (m, 1H) |
| T48 | 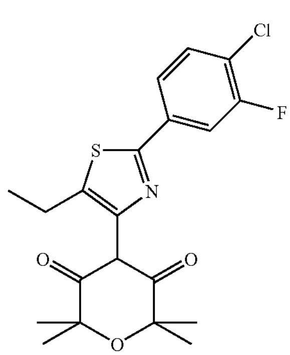 [SMILES: CCc1sc(-c2ccc(Cl)c(F)c2)nc1C1C(=O)C(C)(C)OC(C)(C)C1=O] | δ ppm 1.33 (t, 3H) 1.56 (s, 12H) 2.82 (q, 2H) 7.47 (m, 1H) 7.56 (m, 1H) 7.64 (dd, 1H) |

TABLE T1-continued

| Compound Number | Structure | $^1$H nmr (CDCl$_3$ unless stated) or other physical data |
|---|---|---|
| T49 | 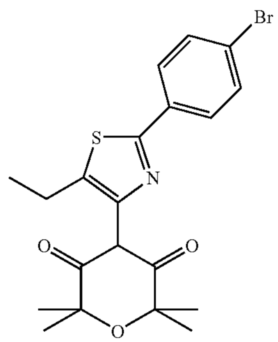 [SMILES: CCc1sc(-c2ccc(Br)cc2)nc1C1C(=O)C(C)(C)OC(C)(C)C1=O] | δ ppm 1.33 (t, 3H) 1.56 (s, 12H) 2.82 (q, 2H) 7.58 (m, 2H) 7.71 (m, 2H) |
| T50 | 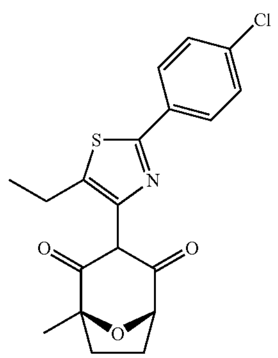 [SMILES: CCc1sc(-c2ccc(Cl)cc2)nc1C1C(=O)[C@@H]2CC[C@@](C)(O2)C1=O] | δ ppm 1.33 (t, 3H) 1.66 (s, 3H) 1.87-2.07 (m, 3H) 2.44 (m, 1H) 2.95 (q, 2H) 4.77 (s, 1H) 7.42 (d, 2H) 7.75 (d, 2H) |
| T51 | 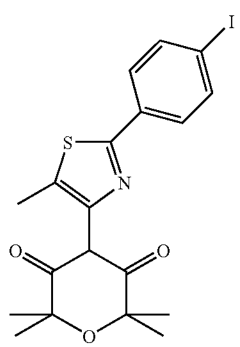 [SMILES: Cc1sc(-c2ccc(I)cc2)nc1C1C(=O)C(C)(C)OC(C)(C)C1=O] | δ ppm 1.56 (s, 12H) 2.40 (s, 3H) 7.55 (d, 2H) 7.78 (d, 2H) |
| T52 | 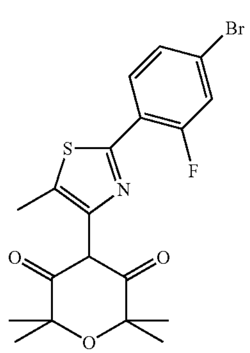 [SMILES: Cc1sc(-c2ccc(Br)cc2F)nc1C1C(=O)C(C)(C)OC(C)(C)C1=O] | δ ppm 1.56 (s, 12H) 2.42 (s, 3H) 7.40 (m, 1H) 7.43 (m, 1H) 7.89 (m, 1H) |

TABLE T1-continued

| Compound Number | Structure | ¹H nmr (CDCl₃ unless stated) or other physical data |
|---|---|---|
| T53 | 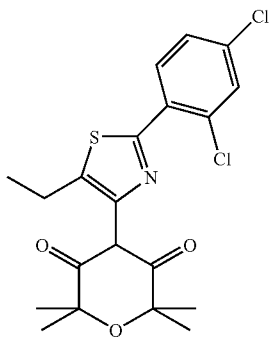 [SMILES: CCc1sc(-c2ccc(Cl)cc2Cl)nc1C1C(=O)C(C)(C)OC(C)(C)C1=O] | δ ppm 1.28 (t, 3H) 1.49 (s, 12H) 2.79 (q, 2H) 7.29 (dd, 1H) 7.48 (d, 1H) 7.82 (d, 1H) |
| T54 | 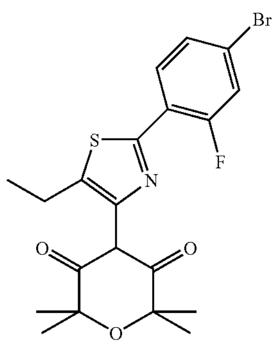 | δ ppm 1.34 (t, 3H) 1.56 (s, 12H) 2.85 (q, 2H) 7.40 (m, 1H) 7.42 (m, 1H) 7.89 (m, 1H) |
| T55 | 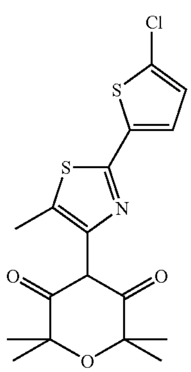 [SMILES: Cc1sc(-c2ccc(Cl)s2)nc1C1C(=O)C(C)(C)OC(C)(C)C1=O] | δ ppm 1.59 (s, 12H) 2.41 (s, 3H) 6.95 (d, 1H) 7.27 (d, 1H) |
| T56 | 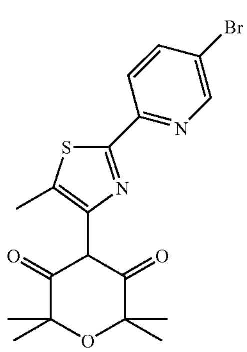 [SMILES: Cc1sc(-c2ccc(Br)cn2)nc1C1C(=O)C(C)(C)OC(C)(C)C1=O] | δ ppm 1.56 (s, 12H) 2.42 (s, 3H) 7.88 (d, 1H) 7.92 (dd, 1H) 8.66 (d, 1H) |

TABLE T1-continued

| Compound Number | Structure | ¹H nmr (CDCl₃ unless stated) or other physical data |
|---|---|---|
| T57 | 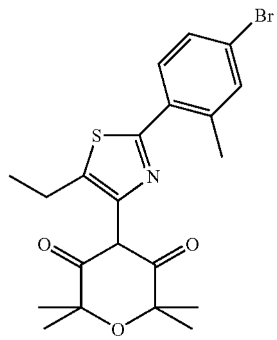 [SMILES: CCc1sc(-c2ccc(Br)cc2C)nc1C1C(=O)C(C)(C)OC(C)(C)C1=O] | δ ppm 1.34 (t, 3H) 1.55 (s, 12H) 2.56 (s, 3H) 2.84 (q, 2H) 7.42 (dd, 1H) 7.48 (d, 1H) 7.52 (d, 1H) |
| T58 | 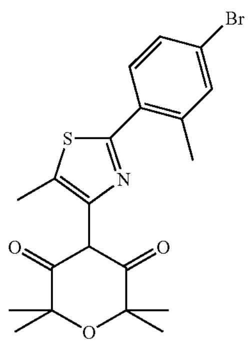 [SMILES: Cc1cc(Br)ccc1-c1nc(C2C(=O)C(C)(C)OC(C)(C)C2=O)c(C)s1] | δ ppm 1.55 (s, 12H) 2.42 (s, 3H) 2.55 (s, 3H) 7.41 (dd, 1H) 7.48 (d, 1H) 7.51 (d, 1H) |
| T59 | 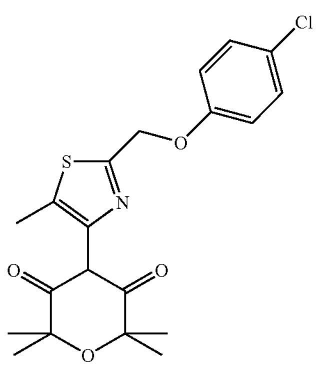 [SMILES: Cc1sc(COc2ccc(Cl)cc2)nc1C1C(=O)C(C)(C)OC(C)(C)C1=O] | δ ppm 1.54 (s, 12H) 2.35 (s, 3H) 5.26 (s, 2H) 6.90 (m, 2H) 7.27 (m, 2H) |
| T60 | 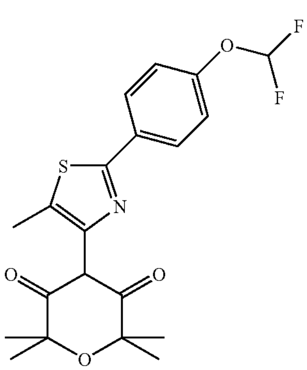 [SMILES: Cc1sc(-c2ccc(OC(F)F)cc2)nc1C1C(=O)C(C)(C)OC(C)(C)C1=O] | δ ppm 1.56 (s, 12H) 2.41 (s, 3H) 6.57 (t, 1H) 7.20 (m, 2H) 7.83 (m, 2H) |

TABLE T1-continued

| Compound Number | Structure | 1H nmr (CDCl3 unless stated) or other physical data |
| --- | --- | --- |
| T61 | 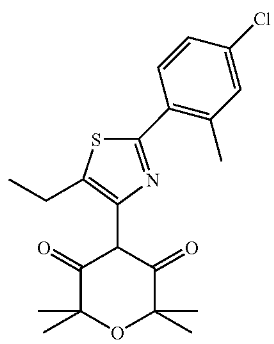 [SMILES: CCc1sc(-c2ccc(Cl)cc2C)nc1C1C(=O)C(C)(C)OC(C)(C)C1=O] | δ ppm 1.34 (t, 3H) 1.55 (s, 12H) 2.56 (s, 3H) 2.84 (q, 2H) 7.32 (s, 1H) 7.59 (d, 1H) 7.68 (d, 1H) |
| T62 | 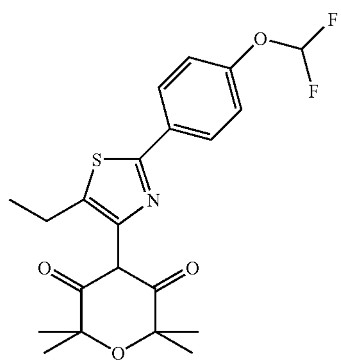 [SMILES: CCc1sc(-c2ccc(OC(F)F)cc2)nc1C1C(=O)C(C)(C)OC(C)(C)C1=O] | δ ppm 1.33 (t, 3H) 1.56 (s, 12H) 2.82 (q, 2H) 6.57 (t, 1H) 7.20 (m, 2H) 7.85 (m, 2H) |
| T63 | 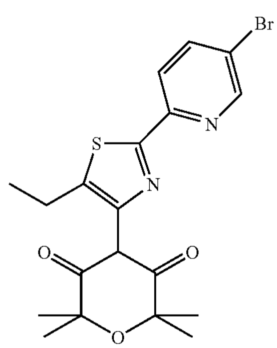 [SMILES: CCc1sc(-c2ccc(Br)cn2)nc1C1C(=O)C(C)(C)OC(C)(C)C1=O] | δ ppm 1.35 (t, 3H) 1.56 (s, 12H) 2.82 (q, 2H) 7.80 (d, 1H) 7.93 (dd, 1H) 8.66 (d, 1H) |
| T64 | 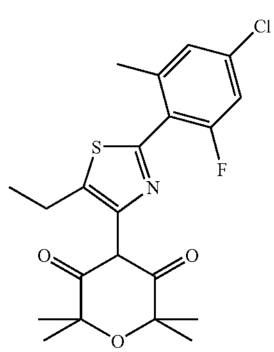 [SMILES: CCc1sc(-c2c(C)cc(Cl)cc2F)nc1C1C(=O)C(C)(C)OC(C)(C)C1=O] | δ ppm 1.34 (t, 3H) 1.54 (s, 12H) 2.41 (s, 3H) 2.86 (q, 2H) 7.08 (m, 1H) 7.13 (m, 1H) |

TABLE T1-continued

| Compound Number | Structure | ¹H nmr (CDCl₃ unless stated) or other physical data |
|---|---|---|
| T65 | 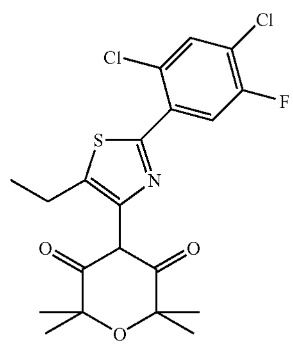 [SMILES: CCc1sc(-c2cc(F)c(Cl)cc2Cl)nc1C1C(=O)C(C)(C)OC(C)(C)C1=O] | δ ppm 1.35 (t, 3H) 1.56 (s, 12H) 2.86 (q, 2H) 7.59 (d, 1H) 7.80 (d, 1H) |
| T66 | 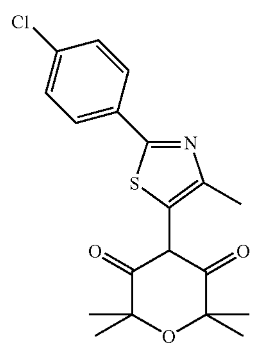 [SMILES: Cc1nc(-c2ccc(Cl)cc2)sc1C1C(=O)C(C)(C)OC(C)(C)C1=O] | δ ppm 1.43 (s, 12H) 2.1 (s, 3H) 7.5 (d, 2H) 7.9 (d, 2H) |
| T67 | 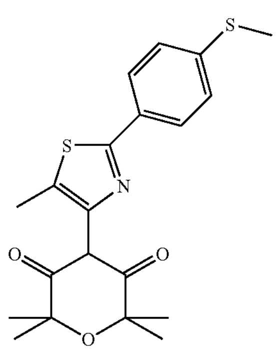 | δ ppm 1.56 (s, 12H) 2.40 (s, 3H) 2.53 (s, 3H) 7.28 (m, 2H) 7.74 (m, 2H) |
| T68 | 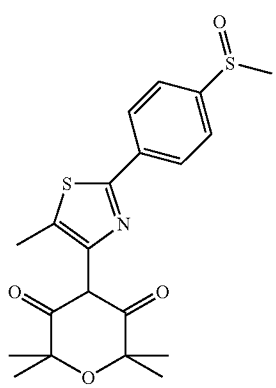 | δ ppm 1.57 (s, 12H) 2.43 (s, 3H) 2.78 (s, 3H) 7.73 (m, 2H) 7.99 (m, 2H) |

TABLE T1-continued

| Compound Number | Structure | $^1$H nmr (CDCl$_3$ unless stated) or other physical data |
|---|---|---|
| T69 | 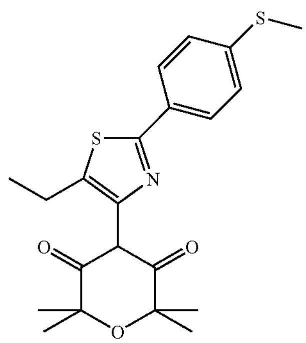 [SMILES: CCc1sc(-c2ccc(SC)cc2)nc1C1C(=O)C(C)(C)OC(C)(C)C1=O] | δ ppm 1.32 (t, 3H) 1.56 (s, 12H) 2.53 (s, 3H) 2.82 (q, 2H) 7.28 (m, 2H) 7.75 (m, 2H) |
| T70 | 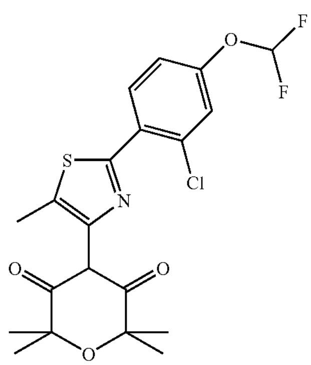 [SMILES: Cc1sc(-c2ccc(OC(F)F)cc2Cl)nc1C1C(=O)C(C)(C)OC(C)(C)C1=O] | δ ppm 1.56 (s, 12H) 2.43 (s, 3H) 6.58 (t, 1H) 7.16 (dd, 1H) 7.31 (d, 1H) 7.95 (d, 1H) |
| T71 | 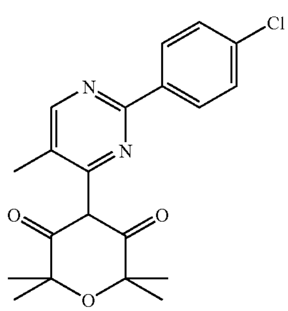 [SMILES: Cc1cnc(-c2ccc(Cl)cc2)nc1C1C(=O)C(C)(C)OC(C)(C)C1=O] | δ ppm 1.55 (s, 12H) 2.19 (s, 3H) 7.55 (m, 2H) 8.21 (m, 2H) 8.60 (s, 1H) |
| T72 | 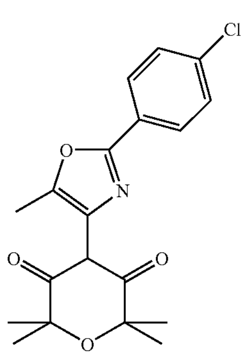 | δ ppm 1.48 (s, 6H) 1.63 (s, 6H) 2.57 (s, 3H) 7.48 (d, 2H) 7.90 (d, 2H) 8.77 (s (br), 1H) |

TABLE T1-continued

| Compound Number | Structure | $^1$H nmr (CDCl$_3$ unless stated) or other physical data |
| --- | --- | --- |
| T73 | 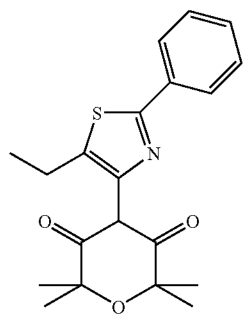 [SMILES: CCc1sc(-c2ccccc2)nc1C1C(=O)C(C)(C)OC(C)(C)C1=O] | δ ppm 1.3 (t, 3H) 1.55 (s, 12H) 2.8 (q, 2H) 7.45 (m, 3H) 7.85 (m, 2H) |
| T74 | 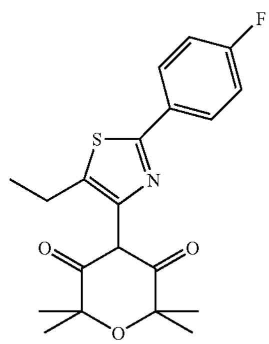 [SMILES: CCc1sc(-c2ccc(F)cc2)nc1C1C(=O)C(C)(C)OC(C)(C)C1=O] | δ ppm 1.37 (t, 3H) 1.6 (s, 12H) 2.85 (q, 2H) 7.2 (m, 2H) 7.85 (m, 2H) |
| T75 | 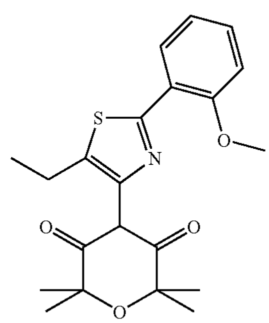 [SMILES: CCc1sc(-c2ccccc2OC)nc1C1C(=O)C(C)(C)OC(C)(C)C1=O] | δ ppm 1.35 (t, 3H) 1.6 (s, 12H) 2.8 (q, 2H) 4.05 (s, 3H) 7.1 (m, 2H) 7.5 (m, 1H) 8.0 (d, 1H) |
| T76 | 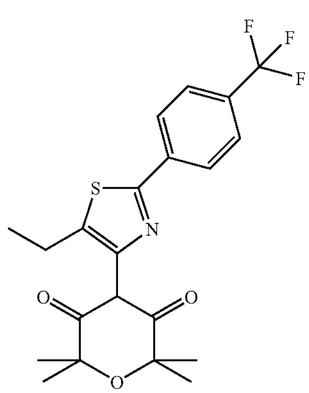 [SMILES: CCc1sc(-c2ccc(C(F)(F)F)cc2)nc1C1C(=O)C(C)(C)OC(C)(C)C1=O] | δ ppm 1.35 (t, 3H) 1.6 (s, 12H) 2.85 (q, 2H) 7.7 (d, 2H) 7.95 (d, 2H) |

TABLE T1-continued

| Compound Number | Structure | ¹H nmr (CDCl₃ unless stated) or other physical data |
| --- | --- | --- |
| T77 | 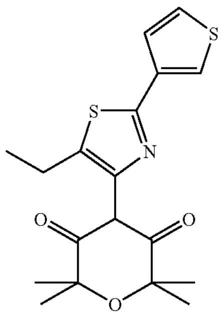 [SMILES: CCc1sc(-c2ccsc2)nc1C1C(=O)C(C)(C)OC(C)(C)C1=O] | δ ppm 1.3 (t, 3H) 1.55 (s, 12H) 2.8 (q, 2H) 7.40 (m, 1H) 7.45 (d, 1H) 7.8 (s, 1H) 9.0 (s br, 1H) |
| T78 | 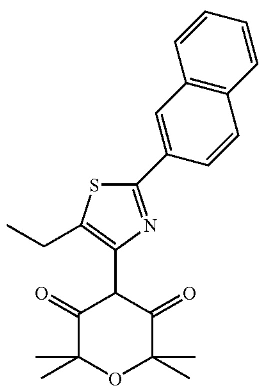 [SMILES: CCc1sc(-c2ccc3ccccc3c2)nc1C1C(=O)C(C)(C)OC(C)(C)C1=O] | δ ppm 1.3 (t, 3H) 1.55 (s, 12H) 2.8 (q, 2H) 7.5 (m, 2H) 7.90 (m, 4H) 8.3 (s, 1H) 9.1 (s br, 1H) |
| T79 | 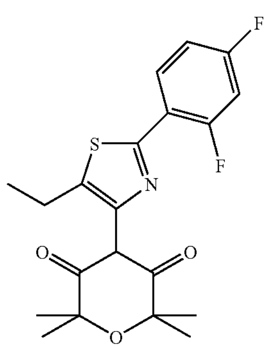 [SMILES: CCc1sc(-c2ccc(F)cc2F)nc1C1C(=O)C(C)(C)OC(C)(C)C1=O] | δ ppm 1.35 (t, 3H) 1.6 (s, 12H) 2.85 (q, 2H) 7.0 (m, 2H) 8.0 (m, 1H) |
| T80 | 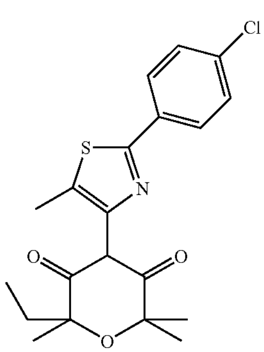 [SMILES: CCC1(C)OC(C)(C)C(=O)C(c2nc(-c3ccc(Cl)cc3)sc2C)C1=O] | δ ppm 0.95 (t, 3H) 1.52 (s, 3H) 1.53 (s, 3H) 1.58 (s, 3H) 1.74 (m, 1H) 1.97 (m, 1H) 2.41 (s, 3H) 7.41 (d, 2H) 7.73 (d, 2H) |

TABLE T1-continued

| Compound Number | Structure | ¹H nmr (CDCl₃ unless stated) or other physical data |
|---|---|---|
| T81 | 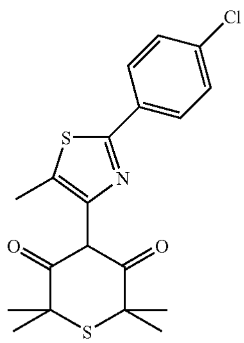 | δ ppm 1.65 (s, 12 H) 2.26 (s, 3H) 7.42 (d, 2H) 7.76 (d, 2H) |

Example 8

Preparation of 2,2-dimethylpropionic acid 4-[2-(4-chlorophenyl)-5-ethylthiazol-4-yl]-2,2,6,6-tetramethyl-5-oxo-5,6-dihydro-2H-pyran-3-yl ester (Compound P2 in Table P1)

To a solution of 4-[2-(4-chlorophenyl)-5-ethylthiazol-4-yl]-2,2,6,6-tetramethylpyran-3,5-dione (49 mg, 0.125 mmol) in dichloromethane (2 ml) is added triethylamine (87 μl, 0.625 mmol), followed by pivaloyl chloride (78 μl, 0.625 mmol), and the reaction mixture is stirred at room temperature for 17 hours. The reaction mixture is purified by flash chromatography on silica gel to give 2,2-dimethylpropionic acid 4-[2-(4-chlorophenyl)-5-ethylthiazol-4-yl]-2,2,6,6-tetramethyl-5-oxo-5,6-dihydro-2H-pyran-3-yl ester.

Additional compounds in Table P1 below are prepared by similar methods using appropriate starting materials.

TABLE P1

| Compound Number | Structure | ¹H nmr (CDCl₃ unless stated) or other physical data |
|---|---|---|
| P1 | 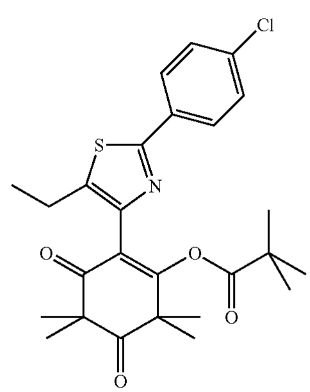 [SMILES: CCc1sc(-c2ccc(Cl)cc2)nc1C1=C(OC(=O)C(C)(C)C)C(C)(C)C(=O)C(C)(C)C1=O] | δ ppm 1.00 (s, 9H) 1.29 (t, 3H) 1.48 (s, 6) 1.51 (s, 6H) 2.63 (q, 2H) 7.37 (m, 2H) 7.80 (m, 2H) |

TABLE P1-continued
| Compound Number | Structure | ¹H nmr (CDCl₃ unless stated) or other physical data |
|---|---|---|
| P2 | 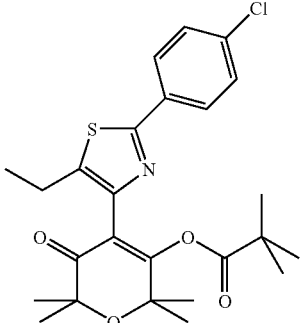 | δ ppm 0.98 (s, 9H) 1.29 (t, 3H) 1.52 (s, 6H) 1.55 (s, 6H) 2.61 (q, 2H) 7.36 (m 2H) 7.81 (d, 2H) |
| P3 | 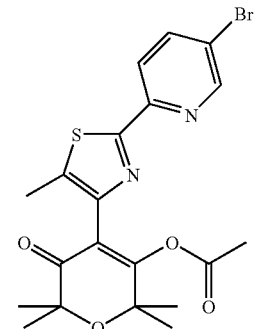 | δ ppm 1.53 (s, 6H) 1.57 (s, 6H) 1.91 (s 3H) 2.28 (s, 3H) 7.86 (dd, 1H) 8.04 (d, 1H) 8.62 (d, 1H) |
| P4 | 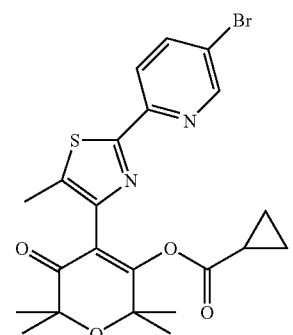 | δ ppm 0.73 (m, 4H) 1.49 (m, 1H) 1.52 (s, 6H) 1.57 (s, 6H) 2.27 (s, 3H) 7.86 (dd, 1H) 8.05 (d, 1H) 8.61 (d, 1H) |
| P5 | 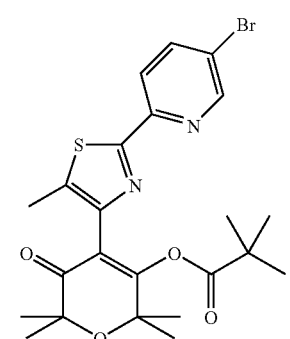 | δ ppm 0.99 (s, 9H) 1.53 (s, 6H) 1.55 (s, 6H) 2.28 (s, 3H) 7.85 (dd, 1H) 8.01 (d, 1H) 8.60 (d, 1H) |

TABLE P1-continued

| Compound Number | Structure | ¹H nmr (CDCl₃ unless stated) or other physical data |
|---|---|---|
| P6 | 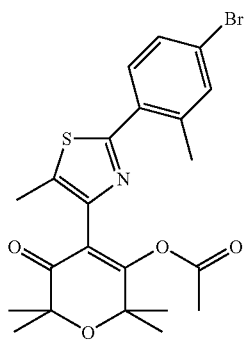 [SMILES: CC(=O)OC1=C(c2nc(-c3ccc(Br)cc3C)sc2C)C(=O)C(C)(C)OC1(C)C] | δ ppm 1.53 (s, 6H) 1.56 (s, 6H) 1.93 (s, 3H) 2.28 (s, 3H) 2.53 (s, 3H) 7.36 (dd, 1H) 7.43 (d, 1H) 7.54 (d, 1H) |
| P7 | 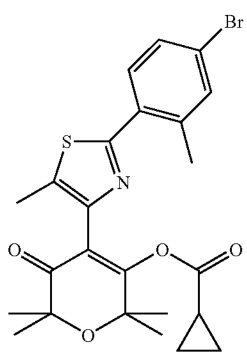 [SMILES: Cc1cc(Br)ccc1-c1nc(C2=C(OC(=O)C3CC3)C(C)(C)OC(C)(C)C2=O)c(C)s1] | δ ppm 0.76 (m, 4H) 1.52-1.57 (m, 13H) 2.27 (s, 3H) 2.54 (s, 3H) 7.36 (dd, 1H) 7.42 (d, 1H) 7.54 (d, 1H) |
| P8 | 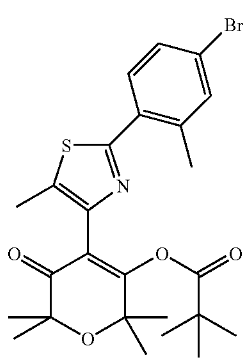 [SMILES: Cc1cc(Br)ccc1-c1nc(C2=C(OC(=O)C(C)(C)C)C(C)(C)OC(C)(C)C2=O)c(C)s1] | δ ppm 1.02 (s, 9H) 1.53 (s, 6H) 1.55 (s, 6H) 2.28 (s, 3H) 2.53 (s, 3H) 7.35 (dd, 1H) 7.41 (d, 1H) 7.56 (d, 1H) |
| P9 | 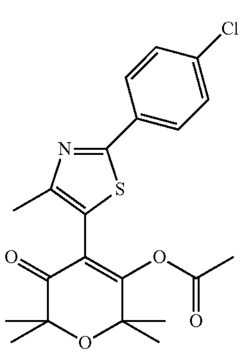 [SMILES: CC(=O)OC1=C(c2sc(-c3ccc(Cl)cc3)nc2C)C(=O)C(C)(C)OC1(C)C] | δ ppm 1.52 (s, 6H) 1.55 (s 6H) 2.01 (s, 3H) 2.32 (s, 3H) 7.40 (d 2H) 7.85 (d 2H) |

TABLE P1-continued

| Compound Number | Structure | ¹H nmr (CDCl₃ unless stated) or other physical data |
|---|---|---|
| P10 | 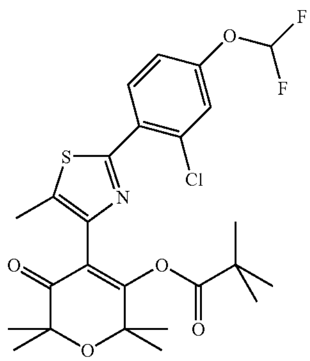 [SMILES: Cc1sc(-c2ccc(OC(F)F)cc2Cl)nc1C1=C(OC(=O)C(C)(C)C)C(C)(C)OC(C)(C)C1=O] | δ ppm 0.99 (s, 9H) 1.53 (s, 6H) 1.55 (s, 6H) 2.29 (s, 3H) 6.55 (t, 1H) 7.09 (dd, 1H) 7.24 (d, 1H) 8.22 (d, 1H) |
| P11 | 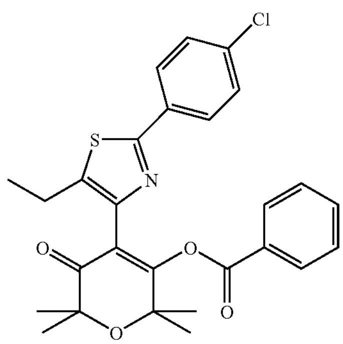 [SMILES: CCc1sc(-c2ccc(Cl)cc2)nc1C1=C(OC(=O)c2ccccc2)C(C)(C)OC(C)(C)C1=O] | δ ppm 1.29 (t, 3H) 1.57 (s, 6H) 1.66 (s, 6H) 2.64 (q, 2H) 7.24 (m, 2H) 7.31 (m, 2H) 7.48 (m, 1H) 7.54 (m, 2H) 7.87 (m, 2H) |
| P12 | 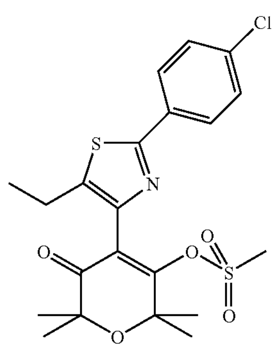 [SMILES: CCc1sc(-c2ccc(Cl)cc2)nc1C1=C(OS(C)(=O)=O)C(C)(C)OC(C)(C)C1=O] | δ ppm 1.32 (t, 3H) 1.51 (s, 6H) 1.67 (s, 6H) 2.49 (s, 3H) 2.64 (q, 2H) 7.39 (m, 2H) 7.84 (d, 2H) |
| P13 | 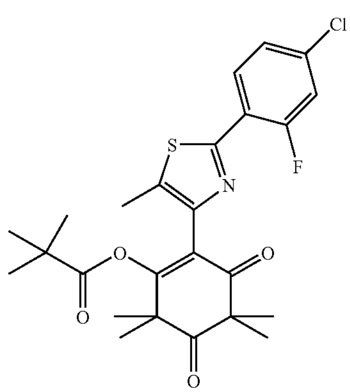 [SMILES: Cc1sc(-c2ccc(Cl)cc2F)nc1C1=C(OC(=O)C(C)(C)C)C(C)(C)C(=O)C(C)(C)C1=O] | δ ppm 1.0 (s, 9H) 1.5 (d, 12H) 2.3 (s, 3H) 7.19 (d, 2H) 8.17 (t, 1H) |

TABLE P1-continued

| Compound Number | Structure | $^1$H nmr (CDCl$_3$ unless stated) or other physical data |
|---|---|---|
| P14 | 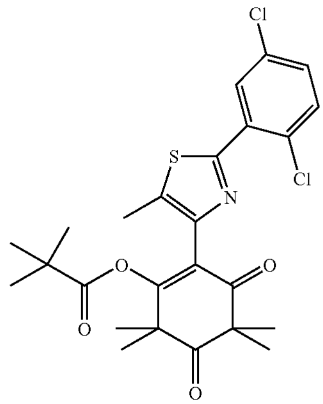 [SMILES: Cc1sc(-c2cc(Cl)ccc2Cl)nc1C1=C(OC(=O)C(C)(C)C)C(C)(C)C(=O)C(C)(C)C1=O] | δ ppm 1.0 (s, 9H) 1.59 (d, 12H) 2.30 (s, 3H) 7.2 (d, 1H) 7.4 (d, 1H) 8.2 (s, 1H) |
| P15 | 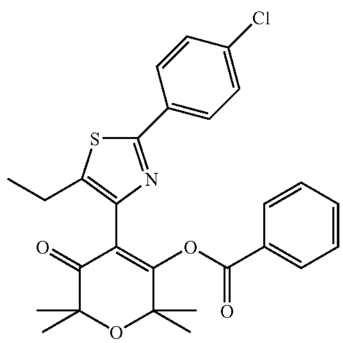 [SMILES: CCc1sc(-c2ccc(Cl)cc2)nc1C1=C(OC(=O)c2ccccc2)C(C)(C)OC(C)(C)C1=O] | δ ppm 1.29 (t, 3H) 1.57 (s, 6H) 1.66 (s, 6H) 2.64 (q, 2H) 7.24 (m, 2H) 7.31 (m, 2H) 7.48 (m, 1H) 7.54 (m, 2H) 7.87 (m, 2H) |
| P16 | 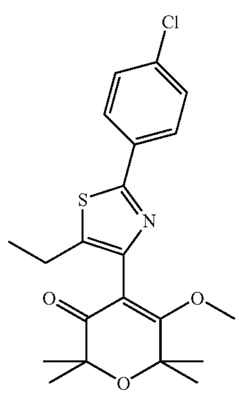 [SMILES: CCc1sc(-c2ccc(Cl)cc2)nc1C1=C(OC)C(C)(C)OC(C)(C)C1=O] | δ ppm 1.32 (t, 3H) 1.51 (s, 6H) 1.67 (s, 6H) 2.49 (s, 3H) 2.64 (q, 2H) 7.39 (m, 2H) 7.84 (m, 2H) |
| P17 | 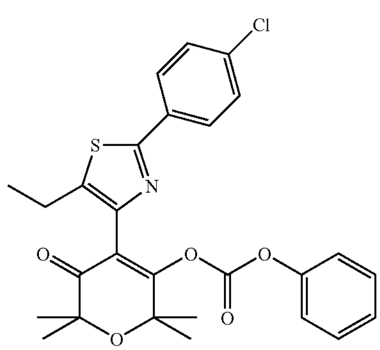 [SMILES: CCc1sc(-c2ccc(Cl)cc2)nc1C1=C(OC(=O)Oc2ccccc2)C(C)(C)OC(C)(C)C1=O] | δ ppm 1.29 (t, 3H) 1.53 (s, 6H) 1.66 (s, 6H) 2.64 (q, 2H) 6.80 (m, 2H) 7.20 (m, 3H) 7.35 (m, 2H) 7.82 (d, 2H) |

TABLE P1-continued

| Compound Number | Structure | $^1$H nmr (CDCl$_3$ unless stated) or other physical data |
|---|---|---|
| P18 | 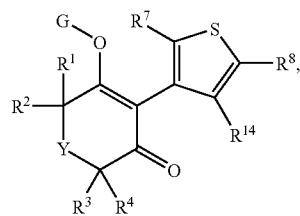 | δ ppm 1.10 (t, 3H) 1.50 (s, 6H) 1.73 (s, 6H) 2.39 (s (br), 2H) 2.64 (q, 2H) 7.21 (m, 2H) 7.34 (d, 2H) 7.46 (m, 3H) 7.67 (m, 2H) |

Table 1:

This table covers 126 compounds of the structural type T-1:

wherein Y is O, $R^1$, $R^2$, $R^3$ and $R^4$ are hydrogen, G is hydrogen and $R^7$, $R^8$ and $R^{14}$ are as defined below:

| Compound Number | $R^7$ | $R^8$ | $R^{14}$ |
|---|---|---|---|
| 1.001 | CH$_3$ | H | H |
| 1.002 | CH$_3$ | H | CH$_3$ |
| 1.003 | CH$_3$ | CH$_3$ | H |
| 1.004 | CH$_3$ | CH$_3$ | CH$_3$ |
| 1.005 | CH$_3$ | CH$_3$CH$_2$ | CH$_3$ |
| 1.006 | CH$_3$CH$_2$ | H | H |
| 1.007 | CH$_3$CH$_2$ | H | CH$_3$ |
| 1.008 | CH$_3$CH$_2$ | CH$_3$ | H |
| 1.009 | CH$_3$CH$_2$ | CH$_3$ | CH$_3$ |
| 1.010 | CH$_3$CH$_2$ | H | CH$_3$CH$_2$ |
| 1.011 | CH$_3$CH$_2$ | CH$_3$ | CH$_3$CH$_2$ |
| 1.012 | CH$_3$CH$_2$ | CH$_3$CH$_2$ | H |
| 1.013 | CH$_3$CH$_2$ | CH$_3$CH$_2$ | CH$_3$ |
| 1.014 | CH$_3$CH$_2$ | CH$_3$CH$_2$ | CH$_3$CH$_2$ |
| 1.015 | CH$_3$ | phenyl | H |
| 1.016 | CH$_3$ | 2-fluorophenyl | H |
| 1.017 | CH$_3$ | 3-fluorophenyl | H |
| 1.018 | CH$_3$ | 4-fluorophenyl | H |
| 1.019 | CH$_3$ | 2-chlorophenyl | H |
| 1.020 | CH$_3$ | 3-chlorophenyl | H |
| 1.021 | CH$_3$ | 4-chlorophenyl | H |
| 1.022 | CH$_3$ | 2-bromophenyl | H |
| 1.023 | CH$_3$ | 3-bromophenyl | H |
| 1.024 | CH$_3$ | 4-bromophenyl | H |
| 1.025 | CH$_3$ | 2-methylphenyl | H |
| 1.026 | CH$_3$ | 3-methylphenyl | H |
| 1.027 | CH$_3$ | 4-methylphenyl | H |
| 1.028 | CH$_3$ | 2-cyanophenyl | H |
| 1.029 | CH$_3$ | 3-cyanophenyl | H |
| 1.030 | CH$_3$ | 4-cyanophenyl | H |
| 1.031 | CH$_3$ | 2-methoxyphenyl | H |
| 1.032 | CH$_3$ | 3-methoxyphenyl | H |
| 1.033 | CH$_3$ | 4-methoxyphenyl | H |
| 1.034 | CH$_3$ | 2-trifluoromethylphenyl | H |
| 1.035 | CH$_3$ | 3-trifluoromethylphenyl | H |
| 1.036 | CH$_3$ | 4-trifluoromethylphenyl | H |
| 1.037 | CH$_3$ | 4-trifluoromethoxyphenyl | H |
| 1.038 | CH$_3$ | 4-difluoromethoxyphenyl | H |
| 1.039 | CH$_3$ | 4-methylthiophenyl | H |
| 1.040 | CH$_3$ | 4-methylsulfinylphenyl | H |
| 1.041 | CH$_3$ | 4-methylsulfonylphenyl | H |
| 1.042 | CH$_3$ | 4-trifluoromethylthiophenyl | H |
| 1.043 | CH$_3$ | 4-trifluoromethylsulfinylphenyl | H |
| 1.044 | CH$_3$ | 4-trifluoromethylsulfonylphenyl | H |
| 1.045 | CH$_3$ | 2,3-difluorophenyl | H |
| 1.046 | CH$_3$ | 2,4-difluorophenyl | H |
| 1.047 | CH$_3$ | 2,5-difluorophenyl | H |
| 1.048 | CH$_3$ | 2,6-difluorophenyl | H |
| 1.049 | CH$_3$ | 3,4-difluorophenyl | H |
| 1.050 | CH$_3$ | 3,5-difluorophenyl | H |
| 1.051 | CH$_3$ | 2,3-dichlorophenyl | H |
| 1.052 | CH$_3$ | 2,4-dichlorophenyl | H |
| 1.053 | CH$_3$ | 2,5-dichlorophenyl | H |
| 1.054 | CH$_3$ | 2,6-dichlorophenyl | H |
| 1.055 | CH$_3$ | 3,4-dichlorophenyl | H |
| 1.056 | CH$_3$ | 3,5-dichlorophenyl | H |
| 1.057 | CH$_3$ | 4-chloro-2-fluorophenyl | H |
| 1.058 | CH$_3$ | 4-chloro-3-fluorophenyl | H |
| 1.059 | CH$_3$ | 4-chloro-2-methylphenyl | H |
| 1.060 | CH$_3$ | 4-chloro-3-methylphenyl | H |
| 1.061 | CH$_3$ | 2-fluoro-4-trifluoromethylphenyl | H |
| 1.062 | CH$_3$ | 3-fluoro-4-trifluoromethylphenyl | H |
| 1.063 | CH$_3$ | 2-chloropyridin-5-yl | H |
| 1.064 | CH$_3$ | 3-chloropyridinyl-5-yl | H |
| 1.065 | CH$_3$ | 2-methylpyridin-5-yl | H |
| 1.066 | CH$_3$ | 3-methylpyridinyl-5-yl | H |
| 1.067 | CH$_3$ | 2-trifluoromethylpyridin-5-yl | H |
| 1.068 | CH$_3$ | 3-trifluoromethylpyridin-5-yl | H |
| 1.069 | CH$_3$ | 2,6-dichloropyridin-3-yl | H |
| 1.070 | CH$_3$ | 4-chloropyrazol-1-yl | H |
| 1.071 | CH$_3$CH$_2$ | phenyl | H |
| 1.072 | CH$_3$CH$_2$ | 2-fluorophenyl | H |
| 1.073 | CH$_3$CH$_2$ | 3-fluorophenyl | H |
| 1.074 | CH$_3$CH$_2$ | 4-fluorophenyl | H |
| 1.075 | CH$_3$CH$_2$ | 2-chlorophenyl | H |
| 1.076 | CH$_3$CH$_2$ | 3-chlorophenyl | H |
| 1.077 | CH$_3$CH$_2$ | 4-chlorophenyl | H |
| 1.078 | CH$_3$CH$_2$ | 2-bromophenyl | H |
| 1.079 | CH$_3$CH$_2$ | 3-bromophenyl | H |
| 1.080 | CH$_3$CH$_2$ | 4-bromophenyl | H |
| 1.081 | CH$_3$CH$_2$ | 2-methylphenyl | H |
| 1.082 | CH$_3$CH$_2$ | 3-methylphenyl | H |
| 1.083 | CH$_3$CH$_2$ | 4-methylphenyl | H |
| 1.084 | CH$_3$CH$_2$ | 2-cyanophenyl | H |

-continued

| Compound Number | $R^7$ | $R^8$ | $R^{14}$ |
|---|---|---|---|
| 1.085 | $CH_3CH_2$ | 3-cyanophenyl | H |
| 1.086 | $CH_3CH_2$ | 4-cyanophenyl | H |
| 1.087 | $CH_3CH_2$ | 2-methoxyphenyl | H |
| 1.088 | $CH_3CH_2$ | 3-methoxyphenyl | H |
| 1.089 | $CH_3CH_2$ | 4-methoxyphenyl | H |
| 1.090 | $CH_3CH_2$ | 2-trifluoromethylphenyl | H |
| 1.091 | $CH_3CH_2$ | 3-trifluoromethylphenyl | H |
| 1.092 | $CH_3CH_2$ | 4-trifluoromethylphenyl | H |
| 1.093 | $CH_3CH_2$ | 4-trifluoromethoxyphenyl | H |
| 1.094 | $CH_3CH_2$ | 4-difluoromethoxyphenyl | H |
| 1.095 | $CH_3CH_2$ | 4-methylthiophenyl | H |
| 1.096 | $CH_3CH_2$ | 4-methylsulfinylphenyl | H |
| 1.097 | $CH_3CH_2$ | 4-methylsulfonylphenyl | H |
| 1.098 | $CH_3CH_2$ | 4-trifluoromethylthiophenyl | H |
| 1.099 | $CH_3CH_2$ | 4-trifluoromethylsulfinylphenyl | H |
| 1.100 | $CH_3CH_2$ | 4-trifluoromethylsulfonylphenyl | H |
| 1.101 | $CH_3CH_2$ | 2,3-difluorophenyl | H |
| 1.102 | $CH_3CH_2$ | 2,4-difluorophenyl | H |
| 1.103 | $CH_3CH_2$ | 2,5-difluorophenyl | H |
| 1.104 | $CH_3CH_2$ | 2,6-difluorophenyl | H |
| 1.105 | $CH_3CH_2$ | 3,4-difluorophenyl | H |
| 1.106 | $CH_3CH_2$ | 3,5-difluorophenyl | H |
| 1.107 | $CH_3CH_2$ | 2,3-dichlorophenyl | H |
| 1.108 | $CH_3CH_2$ | 2,4-dichlorophenyl | H |
| 1.109 | $CH_3CH_2$ | 2,5-dichlorophenyl | H |
| 1.110 | $CH_3CH_2$ | 2,6-dichlorophenyl | H |
| 1.111 | $CH_3CH_2$ | 3,4-dichlorophenyl | H |
| 1.112 | $CH_3CH_2$ | 3,5-dichlorophenyl | H |
| 1.113 | $CH_3CH_2$ | 4-chloro-2-fluorophenyl | H |
| 1.114 | $CH_3CH_2$ | 4-chloro-3-fluorophenyl | H |
| 1.115 | $CH_3CH_2$ | 4-chloro-2-methylphenyl | H |
| 1.116 | $CH_3CH_2$ | 4-chloro-3-methylphenyl | H |
| 1.117 | $CH_3CH_2$ | 2-fluoro-4-trifluoromethylphenyl | H |
| 1.118 | $CH_3CH_2$ | 3-fluoro-4-trifluoromethylphenyl | H |
| 1.119 | $CH_3CH_2$ | 2-chloropyridin-5-yl | H |
| 1.120 | $CH_3CH_2$ | 3-chloropyridinyl-5-yl | H |
| 1.121 | $CH_3CH_2$ | 2-methylpyridin-5-yl | H |
| 1.122 | $CH_3CH_2$ | 3-methylpyridinyl-5-yl | H |
| 1.123 | $CH_3CH_2$ | 2-trifluoromethylpyridin-5-yl | H |
| 1.124 | $CH_3CH_2$ | 3-trifluoromethylpyridin-5-yl | H |
| 1.125 | $CH_3CH_2$ | 2,6-dichloropyridin-3-yl | H |
| 1.126 | $CH_3CH_2$ | 4-chloropyrazol-1-yl | H |

Table 2:

This table covers 126 compounds of the structural type T-1, wherein Y is O, $R^1$ is methyl $R^2$, $R^3$ and $R^4$ are hydrogen, G is hydrogen and $R^7$, $R^8$ and $R^{14}$ are as defined in Table 1.

Table 3:

This table covers 126 compounds of the structural type T-1, wherein Y is O, $R^1$ and $R^2$ are methyl, $R^3$ and $R^4$ are hydrogen, G is hydrogen and $R^7$, $R^8$ and $R^{14}$ are as defined in Table 1.

Table 4:

This table covers 126 compounds of the structural type T-1, wherein Y is O, $R^1$ and $R^3$ are methyl, $R^2$ and $R^4$ are hydrogen, G is hydrogen and $R^7$, $R^8$ and $R^{14}$ are as defined in Table 1.

Table 5:

This table covers 126 compounds of the structural type T-1, wherein Y is O, $R^1$, $R^2$, and $R^3$ are methyl, $R^4$ is hydrogen, G is hydrogen and $R^7$, $R^8$ and $R^{14}$ are as defined in Table 1.

Table 6:

This table covers 126 compounds of the structural type T-1, wherein Y is O, $R^1$, $R^2$, $R^3$ and $R^4$ are methyl, G is hydrogen and $R^7$, $R^8$ and $R^{14}$ are as defined in Table 1.

Table 7:

This table covers 126 compounds of the structural type T-1, wherein Y is O, $R^1$ is ethyl, $R^2$, $R^3$ and $R^4$ are hydrogen, G is hydrogen and $R^7$, $R^8$ and $R^{14}$ are as defined in Table 1.

Table 8:

This table covers 126 compounds of the structural type T-1, wherein Y is O, $R^1$ is ethyl, $R^2$ is methyl, $R^3$ and $R^4$ are hydrogen, G is hydrogen and $R^7$, $R^8$ and $R^{14}$ are as defined in Table 1.

Table 9:

This table covers 126 compounds of the structural type T-1, wherein Y is O, $R^1$ is ethyl, $R^2$ and $R^3$ are hydrogen, $R^4$ is methyl, G is hydrogen and $R^7$, $R^8$ and $R^{14}$ are as defined in Table 1.

Table 10:

This table covers 126 compounds of the structural type T-1, wherein Y is O, $R^1$ is ethyl, $R^2$ and $R^3$ are methyl, $R^4$ is hydrogen, G is hydrogen and $R^7$, $R^8$ and $R^{14}$ are as defined in Table 1.

Table 11:

This table covers 126 compounds of the structural type T-1, wherein Y is O, $R^1$ is ethyl, $R^2$ is hydrogen, $R^3$ and $R^4$ are methyl, G is hydrogen and $R^7$, $R^8$ and $R^{14}$ are as defined in Table 1.

Table 12:

This table covers 126 compounds of the structural type T-1, wherein Y is O, $R^1$ is ethyl, $R^2$, $R^3$ and $R^4$ are methyl, G is hydrogen and $R^7$, $R^8$ and $R^{14}$ are as defined in Table 1.

Table 13:

This table covers 126 compounds of the structural type T-1, wherein Y is O, $R^1$ and $R^2$ are ethyl, $R^3$ and $R^4$ are methyl, G is hydrogen and $R^7$, $R^8$ and $R^{14}$ are as defined in Table 1.

Table 14:

This table covers 126 compounds of the structural type T-1, wherein Y is O, $R^1$ and $R^3$ are ethyl, $R^2$ and $R^4$ are methyl, G is hydrogen and $R^7$, $R^8$ and $R^{14}$ are as defined in Table 1.

Table 15:

This table covers 126 compounds of the structural type T-1, wherein Y is O, $R^1$ and $R^2$ are ethyl, $R^3$ and $R^4$ are hydrogen, G is hydrogen and $R^7$, $R^8$ and $R^{14}$ are as defined in Table 1.

Table 16:

This table covers 126 compounds of the structural type T-1, wherein Y is O, $R^1$ and $R^3$ are ethyl, $R^2$ and $R^4$ are hydrogen, G is hydrogen and $R^7$, $R^8$ and $R^{14}$ are as defined in Table 1.

Table 17:

This table covers 126 compounds of the structural type T-1, wherein Y is O, $R^1$ and $R^3$ are ethyl, $R^2$ is methyl, $R^4$ is hydrogen, G is hydrogen and $R^7$, $R^8$ and $R^{14}$ are as defined in Table 1.

Table 18:

This table covers 126 compounds of the structural type T-1, wherein Y is O, $R^1$ and $R^3$ are ethyl, $R^2$ and $R^4$ are methyl, G is hydrogen and $R^7$, $R^8$ and $R^{14}$ are as defined in Table 1.

Table 19:

This table covers 126 compounds of the structural type T-1, wherein Y is O, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 20:

This table covers 126 compounds of the structural type T-1, wherein Y is O, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 21:

This table covers 126 compounds of the structural type T-1, wherein Y is O, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 22:
This table covers 126 compounds of the structural type T-1, wherein Y is O, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 23:
This table covers 126 compounds of the structural type T-1, wherein Y is O, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 24:
This table covers 126 compounds of the structural type T-1, wherein Y is O, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 25:
This table covers 126 compounds of the structural type T-1, wherein Y is O, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 26:
This table covers 126 compounds of the structural type T-1, wherein Y is O, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 27:
This table covers 126 compounds of the structural type T-1, wherein Y is O, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 28:
This table covers 126 compounds of the structural type T-1, wherein Y is O, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 29:
This table covers 126 compounds of the structural type T-1, wherein Y is O, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 30:
This table covers 126 compounds of the structural type T-1, wherein Y is O, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 31:
This table covers 126 compounds of the structural type T-1, wherein Y is S, $R^1$, $R^2$, $R^3$ and $R^4$ are hydrogen, G is hydrogen and $R^7$, $R^8$ and $R^{14}$ are as defined in Table 1.

Table 32:
This table covers 126 compounds of the structural type T-1, wherein Y is S, $R^1$ is methyl, $R^2$, $R^3$ and $R^4$ are hydrogen, G is hydrogen and $R^7$, $R^8$ and $R^{14}$ are as defined in Table 1.

Table 33:
This table covers 126 compounds of the structural type T-1, wherein Y is S, $R^1$ and $R^2$ are methyl, $R^3$ and $R^4$ are hydrogen, G is hydrogen and $R^7$, $R^8$ and $R^{14}$ are as defined in Table 1.

Table 34:
This table covers 126 compounds of the structural type T-1, wherein Y is S, $R^1$ and $R^3$ are methyl, $R^2$ and $R^4$ are hydrogen, G is hydrogen and $R^7$, $R^8$ and $R^{14}$ are as defined in Table 1.

Table 35:
This table covers 126 compounds of the structural type T-1, wherein Y is S, $R^1$, $R^2$, and $R^3$ are methyl, $R^4$ is hydrogen, G is hydrogen and $R^7$, $R^8$ and $R^{14}$ are as defined in Table 1.

Table 36:
This table covers 126 compounds of the structural type T-1, wherein Y is S, $R^1$, $R^2$, $R^3$ and $R^4$ are methyl, G is hydrogen and $R^7$, $R^8$ and $R^{14}$ are as defined in Table 1.

Table 37:
This table covers 126 compounds of the structural type T-1, wherein Y is S, $R^1$ is ethyl, $R^2$, $R^3$ and $R^4$ are hydrogen, G is hydrogen and $R^7$, $R^8$ and $R^{14}$ are as defined in Table 1.

Table 38:
This table covers 126 compounds of the structural type T-1, wherein Y is S, $R^1$ is ethyl, $R^2$ is methyl, $R^3$ and $R^4$ are hydrogen, G is hydrogen and $R^7$, $R^8$ and $R^{14}$ are as defined in Table 1.

Table 39:
This table covers 126 compounds of the structural type T-1, wherein Y is S, $R^1$ is ethyl, $R^2$ and $R^3$ are hydrogen, $R^4$ is methyl, G is hydrogen and $R^7$, $R^8$ and $R^{14}$ are as defined in Table 1.

Table 40:
This table covers 126 compounds of the structural type T-1, wherein Y is S, $R^1$ is ethyl, $R^2$ and $R^3$ are methyl, $R^4$ is hydrogen, G is hydrogen and $R^7$, $R^8$ and $R^{14}$ are as defined in Table 1.

Table 41:
This table covers 126 compounds of the structural type T-1, wherein Y is S, $R^1$ is ethyl, $R^2$ is hydrogen, $R^3$ and $R^4$ are methyl, G is hydrogen and $R^7$, $R^8$ and $R^{14}$ are as defined in Table 1.

Table 42:
This table covers 126 compounds of the structural type T-1, wherein Y is S, $R^1$ is ethyl, $R^2$, $R^3$ and $R^4$ are methyl, G is hydrogen and $R^7$, $R^8$ and $R^{14}$ are as defined in Table 1.

Table 43:
This table covers 126 compounds of the structural type T-1, wherein Y is S, $R^1$ and $R^2$ are ethyl, $R^3$ and $R^4$ are methyl, G is hydrogen and $R^7$, $R^8$ and $R^{14}$ are as defined in Table 1.

Table 44:
This table covers 126 compounds of the structural type T-1, wherein Y is S, $R^1$ and $R^3$ are ethyl, $R^2$ and $R^4$ are methyl, G is hydrogen and $R^7$, $R^8$ and $R^{14}$ are as defined in Table 1.

Table 45:
This table covers 126 compounds of the structural type T-1, wherein Y is S, $R^1$ and $R^2$ are ethyl, $R^3$ and $R^4$ are hydrogen, G is hydrogen and $R^7$, $R^8$ and $R^{14}$ are as defined in Table 1.

Table 46:
This table covers 126 compounds of the structural type T-1, wherein Y is S, $R^1$ and $R^3$ are ethyl, $R^2$ and $R^4$ are hydrogen, G is hydrogen and $R^7$, $R^8$ and $R^{14}$ are as defined in Table 1.

Table 47:
This table covers 126 compounds of the structural type T-1, wherein Y is S, $R^1$ and $R^3$ are ethyl, $R^2$ is methyl, $R^4$ is hydrogen, G is hydrogen and $R^7$, $R^8$ and $R^{14}$ are as defined in Table 1.

Table 48:
This table covers 126 compounds of the structural type T-1, wherein Y is S, $R^1$ and $R^3$ are ethyl, $R^2$ and $R^4$ are methyl, G is hydrogen and $R^7$, $R^8$ and $R^{14}$ are as defined in Table 1.

Table 49:
This table covers 126 compounds of the structural type T-1, wherein Y is S, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 50:
This table covers 126 compounds of the structural type T-1, wherein Y is S, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 51:
This table covers 126 compounds of the structural type T-1, wherein Y is S, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 52:
This table covers 126 compounds of the structural type T-1, wherein Y is S, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 53:
This table covers 126 compounds of the structural type T-1, wherein Y is S, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 54:
This table covers 126 compounds of the structural type T-1, wherein Y is S, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 55:
This table covers 126 compounds of the structural type T-1, wherein Y is S, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 56:
This table covers 126 compounds of the structural type T-1, wherein Y is S, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 57:
This table covers 126 compounds of the structural type T-1, wherein Y is S, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 58:
This table covers 126 compounds of the structural type T-1, wherein Y is S, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 59:
This table covers 126 compounds of the structural type T-1, wherein Y is S, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 60:
This table covers 126 compounds of the structural type T-1, wherein Y is S, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 61:
This table covers 126 compounds of the structural type T-1, wherein Y is S(O), $R^1$, $R^2$, $R^3$ and $R^4$ are hydrogen, G is hydrogen and $R^7$, $R^8$ and $R^{14}$ are as defined in Table 1.

Table 62:
This table covers 126 compounds of the structural type T-1, wherein Y is S(O), $R^1$ is methyl $R^2$, $R^3$ and $R^4$ are hydrogen, G is hydrogen and $R^7$, $R^8$ and $R^{14}$ are as defined in Table 1.

Table 63:
This table covers 126 compounds of the structural type T-1, wherein Y is S(O), $R^1$ and $R^2$ are methyl, $R^3$ and $R^4$ are, hydrogen, G is hydrogen and $R^7$, $R^8$ and $R^{14}$ are as defined in Table 1.

Table 64:
This table covers 126 compounds of the structural type T-1, wherein Y is S(O), $R^1$ and $R^3$ are methyl, $R^2$ and $R^4$ are hydrogen, G is hydrogen and $R^7$, $R^8$ and $R^{14}$ are as defined in Table 1.

Table 65:
This table covers 126 compounds of the structural type T-1, wherein Y is S(O), $R^1$, $R^2$, and $R^3$ are methyl, $R^4$ is hydrogen, G is hydrogen and $R^7$, $R^8$ and $R^{14}$ are as defined in Table 1.

Table 66:
This table covers 126 compounds of the structural type T-1, wherein Y is S(O), $R^1$, $R^2$, $R^3$ and $R^4$ are methyl, G is hydrogen and $R^7$, $R^8$ and $R^{14}$ are as defined in Table 1.

Table 67:
This table covers 126 compounds of the structural type T-1, wherein Y is S(O), $R^1$ is ethyl, $R^2$, $R^3$ and $R^4$ are hydrogen, G is hydrogen and $R^7$, $R^8$ and $R^{14}$ are as defined in Table 1.

Table 68:
This table covers 126 compounds of the structural type T-1, wherein Y is S(O), $R^1$ is ethyl, $R^2$ is methyl, $R^3$ and $R^4$ are hydrogen, G is hydrogen and $R^7$, $R^8$ and $R^{14}$ are as defined in Table 1.

Table 69:
This table covers 126 compounds of the structural type T-1, wherein Y is S(O), $R^1$ is ethyl, $R^2$ and $R^3$ are hydrogen, $R^4$ is methyl, G is hydrogen and $R^7$, $R^8$ and $R^{14}$ are as defined in Table 1.

Table 70:
This table covers 126 compounds of the structural type T-1, wherein Y is S(O), $R^1$ is ethyl, $R^2$ and $R^3$ are methyl, $R^4$ is hydrogen, G is hydrogen and $R^7$, $R^8$ and $R^{14}$ are as defined in Table 1.

Table 71:
This table covers 126 compounds of the structural type T-1, wherein Y is S(O), $R^1$ is ethyl, $R^2$ is hydrogen, $R^3$ and $R^4$ are methyl, G is hydrogen and $R^7$, $R^8$ and $R^{14}$ are as defined in Table 1.

Table 72:
This table covers 126 compounds of the structural type T-1, wherein Y is S(O), $R^1$ is ethyl, $R^2$, $R^3$ and $R^4$ are methyl, G is hydrogen and $R^7$, $R^8$ and $R^{14}$ are as defined in Table 1.

Table 73:
This table covers 126 compounds of the structural type T-1, wherein Y is S(O), $R^1$ and $R^2$ are ethyl, $R^3$ and $R^4$ are methyl, G is hydrogen and $R^7$, $R^8$ and $R^{14}$ are as defined in Table 1.

Table 74:
This table covers 126 compounds of the structural type T-1, wherein Y is S(O), $R^1$ and $R^3$ are ethyl, $R^2$ and $R^4$ are methyl, G is hydrogen and $R^7$, $R^8$ and $R^{14}$ are as defined in Table 1.

Table 75:
This table covers 126 compounds of the structural type T-1, wherein Y is S(O), $R^1$ and $R^2$ are ethyl, $R^3$ and $R^4$ are hydrogen, G is hydrogen and $R^7$, $R^8$ and $R^{14}$ are as defined in Table 1.

Table 76:
This table covers 126 compounds of the structural type T-1, wherein Y is S(O), $R^1$ and $R^3$ are ethyl, $R^2$ and $R^4$ are hydrogen, G is hydrogen and $R^7$, $R^8$ and $R^{14}$ are as defined in Table 1.

Table 77:
This table covers 126 compounds of the structural type T-1, wherein Y is S(O), $R^1$ and $R^3$ are ethyl, $R^2$ is methyl, $R^4$ is hydrogen, G is hydrogen and $R^7$, $R^8$ and $R^{14}$ are as defined in Table 1.

Table 78:
This table covers 126 compounds of the structural type T-1, wherein Y is S(O), $R^1$ and $R^3$ are ethyl, $R^2$ and $R^4$ are methyl, G is hydrogen and $R^7$, $R^8$ and $R^{14}$ are as defined in Table 1.

Table 79:
This table covers 126 compounds of the structural type T-1, wherein Y is S(O), $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 80:
This table covers 126 compounds of the structural type T-1, wherein Y is S(O), $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 81:
This table covers 126 compounds of the structural type T-1, wherein Y is S(O), $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 82:
This table covers 126 compounds of the structural type T-1, wherein Y is S(O), $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 83:
This table covers 126 compounds of the structural type T-1, wherein Y is S(O), $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 84:
This table covers 126 compounds of the structural type T-1, wherein Y is S(O), $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 85:
This table covers 126 compounds of the structural type T-1, wherein Y is S(O), $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 86:
This table covers 126 compounds of the structural type T-1, wherein Y is S(O), $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 87:
This table covers 126 compounds of the structural type T-1, wherein Y is S(O), $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 88:
This table covers 126 compounds of the structural type T-1, wherein Y is S(O), $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 89:
This table covers 126 compounds of the structural type T-1, wherein Y is S(O), $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 90:
This table covers 126 compounds of the structural type T-1, wherein Y is S(O), $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 91:
This table covers 126 compounds of the structural type T-1, wherein Y is $S(O)_2$, $R^1$, $R^2$, $R^3$ and $R^4$ are hydrogen, G is hydrogen and $R^7$, $R^8$ and $R^{14}$ are as defined in Table 1.

Table 92:
This table covers 126 compounds of the structural type T-1, wherein Y is $S(O)_2$, W is methyl $R^2$, $R^3$ and $R^4$ are hydrogen, G is hydrogen and $R^7$, $R^8$ and $R^{14}$ are as defined in Table 1.

Table 93:
This table covers 126 compounds of the structural type T-1, wherein Y is $S(O)_2$, $R^1$ and $R^2$ are methyl, $R^3$ and $R^4$ are hydrogen, G is hydrogen and $R^7$, $R^8$ and $R^{14}$ are as defined in Table 1.

Table 94:
This table covers 126 compounds of the structural type T-1, wherein Y is $S(O)_2$, $R^1$ and $R^3$ are methyl, $R^2$ and $R^4$ are hydrogen, G is hydrogen and $R^7$, $R^8$ and $R^{14}$ are as defined in Table 1.

Table 95:
This table covers 126 compounds of the structural type T-1, wherein Y is $S(O)_2$, $R^1$, $R^2$, and $R^3$ are methyl, $R^4$ is hydrogen, G is hydrogen and $R^7$, $R^8$ and $R^{14}$ are as defined in Table 1.

Table 96:
This table covers 126 compounds of the structural type T-1, wherein Y is $S(O)_2$, $R^1$, $R^2$, $R^3$ and $R^4$ are methyl, G is hydrogen and $R^7$, $R^8$ and $R^{14}$ are as defined in Table 1.

Table 97:
This table covers 126 compounds of the structural type T-1, wherein Y is $S(O)_2$, $R^1$ is ethyl, $R^2$, $R^3$ and $R^4$ are hydrogen, G is hydrogen and $R^7$, $R^8$ and $R^{14}$ are as defined in Table 1.

Table 98:
This table covers 126 compounds of the structural type T-1, wherein Y is $S(O)_2$, $R^1$ is ethyl, $R^2$ is methyl, $R^3$ and $R^4$ are hydrogen, G is hydrogen and $R^7$, $R^8$ and $R^{14}$ are as defined in Table 1.

Table 99:
This table covers 126 compounds of the structural type T-1, wherein Y is $S(O)_2$, $R^1$ is ethyl, $R^2$ and R3 are hydrogen, $R^4$ is methyl, G is hydrogen and $R^7$, $R^8$ and $R^{14}$ are as defined in Table 1.

Table 100:
This table covers 126 compounds of the structural type T-1, wherein Y is $S(O)_2$, $R^1$ is ethyl, $R^2$ and R3 are methyl, $R^4$ is hydrogen, G is hydrogen and $R^7$, $R^8$ and $R^{14}$ are as defined in Table 1.

Table 101:
This table covers 126 compounds of the structural type T-1, wherein Y is $S(O)_2$, $R^1$ is ethyl, $R^2$ is hydrogen, $R^3$ and $R^4$ are methyl, G is hydrogen and $R^7$, $R^8$ and $R^{14}$ are as defined in Table 1.

Table 102:
This table covers 126 compounds of the structural type T-1, wherein Y is $S(O)_2$, $R^1$ is ethyl, $R^2$, $R^3$ and $R^4$ are methyl, G is hydrogen and $R^7$, $R^8$ and $R^{14}$ are as defined in Table 1.

Table 103:
This table covers 126 compounds of the structural type T-1, wherein Y is $S(O)_2$, $R^1$ and $R^2$ are ethyl, $R^3$ and $R^4$ are methyl, G is hydrogen and $R^7$, $R^8$ and $R^{14}$ are as defined in Table 1.

Table 104:
This table covers 126 compounds of the structural type T-1, wherein Y is $S(O)_2$, $R^1$ and $R^3$ are ethyl, $R^2$ and $R^4$ are methyl, G is hydrogen and $R^7$, $R^8$ and $R^{14}$ are as defined in Table 1.

Table 105:
This table covers 126 compounds of the structural type T-1, wherein Y is $S(O)_2$, $R^1$ and $R^2$ are ethyl, $R^3$ and $R^4$ are hydrogen, G is hydrogen and $R^7$, $R^8$ and $R^{14}$ are as defined in Table Table 106:
This table covers 126 compounds of the structural type T-1, wherein Y is $S(O)_2$, $R^1$ and $R^3$ are ethyl, $R^2$ and $R^4$ are hydrogen, G is hydrogen and $R^7$, $R^8$ and $R^{14}$ are as defined in Table 1.

Table 107:
This table covers 126 compounds of the structural type T-1, wherein Y is $S(O)_2$, $R^1$ and $R^3$ are ethyl, $R^2$ is methyl, $R^4$ is hydrogen, G is hydrogen and $R^7$, $R^8$ and $R^{14}$ are as defined in Table 1:

Table 108:
This table covers 126 compounds of the structural type T-1, wherein Y is $S(O)_2$, $R^1$ and $R^3$ are ethyl, $R^2$ and $R^4$ are methyl, G is hydrogen and $R^7$, $R^8$ and $R^{14}$ are as defined in Table 1.

Table 109:
This table covers 126 compounds of the structural type T-1, wherein Y is $S(O)_2$, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 110:
This table covers 126 compounds of the structural type T-1, wherein Y is $S(O)_2$, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 111:
This table covers 126 compounds of the structural type T-1, wherein Y is $S(O)_2$, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 112:
This table covers 126 compounds of the structural type T-1, wherein Y is $S(O)_2$, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 113:
This table covers 126 compounds of the structural type T-1, wherein Y is $S(O)_2$, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 114:
This table covers 126 compounds of the structural type T-1, wherein Y is $S(O)_2$, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 115:
This table covers 126 compounds of the structural type T-1, wherein Y is $S(O)_2$, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 116:
This table covers 126 compounds of the structural type T-1, wherein Y is $S(O)_2$, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 117:
This table covers 126 compounds of the structural type T-1, wherein Y is $S(O)_2$, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 118:
This table covers 126 compounds of the structural type T-1, wherein Y is $S(O)_2$, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 119:
This table covers 126 compounds of the structural type T-1, wherein Y is $S(O)_2$, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 120:
This table covers 126 compounds of the structural type T-1, wherein Y is $S(O)_2$, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 121:
This table covers 126 compounds of the structural type T-1, wherein Y is C=O, $R^1$ and $R^2$ are methyl, $R^3$ and $R^4$ are hydrogen, G is hydrogen and $R^7$, $R^8$ and $R^{14}$ are as defined in Table 1.

Table 122:
This table covers 126 compounds of the structural type T-1, wherein Y is C=O, $R^1$, $R^2$, and $R^3$ are methyl, $R^4$ is hydrogen, G is hydrogen and $R^7$, $R^8$ and $R^{14}$ are as defined in Table 1.

Table 123:
This table covers 126 compounds of the structural type T-1, wherein Y is C=O, $R^1$, $R^2$, $R^3$ and $R^4$ are methyl, G is hydrogen and $R^7$, $R^8$ and $R^{14}$ are as defined in Table 1.

Table 124:
This table covers 126 compounds of the structural type T-1, wherein Y is C=O, $R^1$ is ethyl, $R^2$ is methyl, $R^3$ and $R^4$ are hydrogen, G is hydrogen and $R^7$, $R^8$ and $R^{14}$ are as defined in Table 1.

Table 125:
This table covers 126 compounds of the structural type T-1, wherein Y is C=O, $R^1$ is ethyl, $R^2$ and $R^3$ are methyl, $R^4$ is hydrogen, G is hydrogen and $R^7$, $R^8$ and $R^{14}$ are as defined in Table 1.

Table 126:
This table covers 126 compounds of the structural type T-1, wherein Y is C=O, $R^1$ is ethyl, $R^2$ is hydrogen, $R^3$ and $R^4$ are methyl, G is hydrogen and $R^7$, $R^8$ and $R^{14}$ are as defined in Table 1.

Table 127:
This table covers 126 compounds of the structural type T-1, wherein Y is C=O, $R^1$ is ethyl, $R^2$, $R^3$ and $R^4$ are methyl, G is hydrogen and $R^7$, $R^8$ and $R^{14}$ are as defined in Table 1.

Table 128:
This table covers 126 compounds of the structural type T-1, wherein Y is C=O, $R^1$ and $R^2$ are ethyl, $R^3$ and $R^4$ are methyl, G is hydrogen and $R^7$, $R^8$ and $R^{14}$ are as defined in Table 1.

Table 129:
This table covers 126 compounds of the structural type T-1, wherein Y is C=O, $R^1$ and $R^3$ are ethyl, $R^2$ and $R^4$ are methyl, G is hydrogen and $R^7$, $R^8$ and $R^{14}$ are as defined in Table 1.

Table 130:
This table covers 126 compounds of the structural type T-1, wherein Y is C=O, $R^1$ and $R^2$ are ethyl, $R^3$ and $R^4$ are hydrogen, G is hydrogen and $R^7$, $R^8$ and $R^{14}$ are as defined in Table 1.

Table 131:
This table covers 126 compounds of the structural type T-1, wherein Y is C=O, $R^1$ and $R^3$ are ethyl, $R^2$ is methyl, $R^4$ is hydrogen, G is hydrogen and $R^7$, $R^8$ and $R^{14}$ are as defined in Table 1.

Table 132:
This table covers 126 compounds of the structural type T-1, wherein Y is C=O, $R^1$ and $R^3$ are ethyl, $R^2$ and $R^4$ are methyl, G is hydrogen and $R^7$, $R^8$ and $R^{14}$ are as defined in Table 1.

Table 133:
This table covers 126 compounds of the structural type T-1, wherein Y is C=O, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 134:
This table covers 126 compounds of the structural type T-1, wherein Y is C=O, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 135:
This table covers 126 compounds of the structural type T-1 wherein Y is C=O, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 136:
This table covers 126 compounds of the structural type T-1, wherein Y is C=O, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 137:
This table covers 126 compounds of the structural type T-1, wherein Y is C=O, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 138:
This table covers 126 compounds of the structural type T-1, wherein Y is C=O, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 139:
This table covers 126 compounds of the structural type T-1, wherein Y is C=O, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 140:
This table covers 126 compounds of the structural type T-1, wherein Y is C=O, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 141:
This table covers 126 compounds of the structural type T-1, wherein Y is C=O, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 142:
This table covers 126 compounds of the structural type T-1, wherein Y is C=O, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 143:
This table covers 126 compounds of the structural type T-1, wherein Y is C=O, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 144:
This table covers 126 compounds of the structural type T-1, wherein Y is C=O, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 145:
This table covers 126 compounds of the structural type T-2:

wherein Y is O, $R^1$, $R^2$, $R^3$ and $R^4$ are hydrogen, G is hydrogen and $R^7$, $R^8$ and $R^{14}$ are as defined in Table 1.

Table 146:
This table covers 126 compounds of the structural type T-2, wherein Y is O, $R^1$ is methyl $R^2$, $R^3$ and $R^4$ are hydrogen, G is hydrogen and $R^7$, $R^8$ and $R^{14}$ are as defined in Table 1.

Table 147:
This table covers 126 compounds of the structural type T-2, wherein Y is O, $R^1$ and $R^2$ are methyl, $R^3$ and $R^4$ are hydrogen, G is hydrogen and $R^7$, $R^8$ and $R^{14}$ are as defined in Table 1.

Table 148:
This table covers 126 compounds of the structural type T-2, wherein Y is O, $R^1$ and $R^3$ are methyl, $R^2$ and $R^4$ are hydrogen, G is hydrogen and $R^7$, $R^8$ and $R^{14}$ are as defined in Table 1.

Table 149:
This table covers 126 compounds of the structural type T-2, wherein Y is O, $R^1$, $R^2$, and $R^3$ are methyl, $R^4$ is hydrogen, G is hydrogen and $R^7$, $R^8$ and $R^{14}$ are as defined in Table 1.

Table 150:
This table covers 126 compounds of the structural type T-2, wherein Y is O, $R^1$, $R^2$, $R^3$ and $R^4$ are methyl, G is hydrogen and $R^7$, $R^8$ and $R^{14}$ are as defined in Table 1.

Table 151:
This table covers 126 compounds of the structural type T-2, wherein Y is O, $R^1$ is ethyl, $R^2$, $R^3$ and $R^4$ are hydrogen, G is hydrogen and $R^7$, $R^8$ and $R^{14}$ are as defined in Table 1.

Table 152:
This table covers 126 compounds of the structural type T-2, wherein Y is O, $R^1$ is ethyl, $R^2$ is methyl, $R^3$ and $R^4$ are hydrogen, G is hydrogen and $R^7$, $R^8$ and $R^{14}$ are as defined in Table 1.

Table 153:
This table covers 126 compounds of the structural type T-2, wherein Y is O, $R^1$ is ethyl, $R^2$ and $R^3$ are hydrogen, $R^4$ is methyl, G is hydrogen and $R^7$, $R^8$ and $R^{14}$ are as defined in Table 1.

Table 154:
This table covers 126 compounds of the structural type T-2, wherein Y is O, $R^1$ is ethyl, $R^2$ and $R^3$ are methyl, $R^4$ is hydrogen, G is hydrogen and $R^7$, $R^8$ and $R^{14}$ are as defined in Table 1.

Table 155:
This table covers 126 compounds of the structural type T-2, wherein Y is O, $R^1$ is ethyl, $R^2$ is hydrogen, $R^3$ and $R^4$ are methyl, G is hydrogen and $R^7$, $R^8$ and $R^{14}$ are as defined in Table 1.

Table 156:
This table covers 126 compounds of the structural type T-2, wherein Y is O, $R^1$ is ethyl, $R^2$, $R^3$ and $R^4$ are methyl, G is hydrogen and $R^7$, $R^8$ and $R^{14}$ are as defined in Table 1.

Table 157:
This table covers 126 compounds of the structural type T-2, wherein Y is O, $R^1$ and $R^2$ are ethyl, $R^3$ and $R^4$ are methyl, G is hydrogen and $R^7$, $R^8$ and $R^{14}$ are as defined in Table 1.

Table 158:
This table covers 126 compounds of the structural type T-2, wherein Y is O, $R^1$ and $R^3$ are ethyl, $R^2$ and $R^4$ are methyl, G is hydrogen and $R^7$, $R^8$ and $R^{14}$ are as defined in Table 1.

Table 159:
This table covers 126 compounds of the structural type T-2, wherein Y is O, $R^1$ and $R^2$ are ethyl, $R^3$ and $R^4$ are hydrogen, G is hydrogen and $R^7$, $R^8$ and $R^{14}$ are as defined in Table 1.

Table 160:
This table covers 126 compounds of the structural type T-2, wherein Y is O, $R^1$ and $R^3$ are ethyl, $R^2$ and $R^4$ are hydrogen, G is hydrogen and $R^7$, $R^8$ and $R^{14}$ are as defined in Table 1.

Table 161:
This table covers 126 compounds of the structural type T-2, wherein Y is O, $R^1$ and $R^3$ are ethyl, $R^2$ is methyl, $R^4$ is hydrogen, G is hydrogen and $R^7$, $R^8$ and $R^{14}$ are as defined in Table 1.

Table 162:
This table covers 126 compounds of the structural type T-2, wherein Y is O, $R^1$ and $R^3$ are ethyl, $R^2$ and $R^4$ are methyl, G is hydrogen and $R^7$, $R^8$ and $R^{14}$ are as defined in Table 1.

Table 163:
This table covers 126 compounds of the structural type T-2, wherein Y is O, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 164:
This table covers 126 compounds of the structural type T-2, wherein Y is O, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 165:
This table covers 126 compounds of the structural type T-2, wherein Y is O, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 166:
This table covers 126 compounds of the structural type T-2, wherein Y is O, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 167:
This table covers 126 compounds of the structural type T-2, wherein Y is O, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 168:
This table covers 126 compounds of the structural type T-2, wherein Y is O, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 169:
This table covers 126 compounds of the structural type T-2, wherein Y is O, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 170:
This table covers 126 compounds of the structural type T-2, wherein Y is O, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 171:
This table covers 126 compounds of the structural type T-2, wherein Y is O, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 172:
This table covers 126 compounds of the structural type T-2, wherein Y is O, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 173:
This table covers 126 compounds of the structural type T-2, wherein Y is O, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 174:
This table covers 126 compounds of the structural type T-2, wherein Y is O, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 175:
This table covers 126 compounds of the structural type T-2, wherein Y is S, $R^1$, $R^2$, $R^3$ and $R^4$ are hydrogen, G is hydrogen and $R^7$, $R^8$ and $R^{14}$ are as defined in Table 1.

Table 176:
This table covers 126 compounds of the structural type T-2, wherein Y is S, $R^1$ is methyl $R^2$, $R^3$ and $R^4$ are hydrogen, G is hydrogen and $R^7$, $R^8$ and $R^{14}$ are as defined in Table 1.

Table 177:
This table covers 126 compounds of the structural type T-2, wherein Y is S, $R^1$ and $R^2$ are methyl, R3 and $R^4$ are hydrogen, G is hydrogen and $R^7$, $R^8$ and $R^{14}$ are as defined in Table 1.

Table 178:
This table covers 126 compounds of the structural type T-2, wherein Y is S, $R^1$ and $R^3$ are methyl, $R^2$ and $R^4$ are hydrogen, G is hydrogen and $R^7$, $R^8$ and $R^{14}$ are as defined in Table 1.

Table 179:
This table covers 126 compounds of the structural type T-2, wherein Y is S, $R^1$, $R^2$, and $R^3$ are methyl, $R^4$ is hydrogen, G is hydrogen and $R^7$, $R^8$ and $R^{14}$ are as defined in Table 1.

Table 180:
This table covers 126 compounds of the structural type T-2, wherein Y is S, $R^1$, $R^2$, $R^3$ and $R^4$ are methyl, G is hydrogen and $R^7$, $R^8$ and $R^{14}$ are as defined in Table 1.

Table 181:
This table covers 126 compounds of the structural type T-2, wherein Y is S, $R^1$ is ethyl, $R^2$, $R^3$ and $R^4$ are hydrogen, G is hydrogen and $R^7$, $R^8$ and $R^{14}$ are as defined in Table 1.

Table 182:
This table covers 126 compounds of the structural type T-2, wherein Y is S, $R^1$ is ethyl, $R^2$ is methyl, $R^3$ and $R^4$ are hydrogen, G is hydrogen and $R^7$, $R^8$ and $R^{14}$ are as defined in Table 1.

Table 183:
This table covers 126 compounds of the structural type T-2, wherein Y is S, $R^1$ is ethyl, $R^2$ and $R^3$ are hydrogen, $R^4$ is methyl, G is hydrogen and $R^7$, $R^8$ and $R^{14}$ are as defined in Table 1.

Table 184:
This table covers 126 compounds of the structural type T-2, wherein Y is S, $R^1$ is ethyl, $R^2$ and $R^3$ are methyl, $R^4$ is hydrogen, G is hydrogen and $R^7$, $R^8$ and $R^{14}$ are as defined in Table 1.

Table 185:
This table covers 126 compounds of the structural type T-2, wherein Y is S, $R^1$ is ethyl, $R^2$ is hydrogen, $R^3$ and $R^4$ are methyl, G is hydrogen and $R^7$, $R^8$ and $R^{14}$ are as defined in Table 1.

Table 186:
This table covers 126 compounds of the structural type T-2, wherein Y is S, $R^1$ is ethyl, $R^2$, $R^3$ and $R^4$ are methyl, G is hydrogen and $R^7$, $R^8$ and $R^{14}$ are as defined in Table 1.

Table 187:
This table covers 126 compounds of the structural type T-2, wherein Y is S, $R^1$ and $R^2$ are ethyl, $R^3$ and $R^4$ are methyl, G is hydrogen and $R^7$, $R^8$ and $R^{14}$ are as defined in Table 1.

Table 188:
This table covers 126 compounds of the structural type T-2, wherein Y is S, $R^1$ and $R^3$ are ethyl, $R^2$ and $R^4$ are methyl, G is hydrogen and $R^7$, $R^8$ and $R^{14}$ are as defined in Table 1.

Table 189:
This table covers 126 compounds of the structural type T-2, wherein Y is S, $R^1$ and $R^2$ are ethyl, $R^3$ and $R^4$ are hydrogen, G is hydrogen and $R^7$, $R^8$ and $R^{14}$ are as defined in Table 1.

Table 190:
This table covers 126 compounds of the structural type T-2, wherein Y is S, $R^1$ and $R^3$ are ethyl, $R^2$ and $R^4$ are hydrogen, G is hydrogen and $R^7$, $R^8$ and $R^{14}$ are as defined in Table 1.

Table 191:
This table covers 126 compounds of the structural type T-2, wherein Y is S, $R^1$ and $R^3$ are ethyl, $R^2$ is methyl, $R^4$ is hydrogen, G is hydrogen and $R^7$, $R^8$ and $R^{14}$ are as defined in Table 1:

Table 192:
This table covers 126 compounds of the structural type T-2, wherein Y is S, $R^1$ and $R^3$ are ethyl, $R^2$ and $R^4$ are methyl, G is hydrogen and $R^7$, $R^8$ and $R^{14}$ are as defined in Table 1.

Table 193:
This table covers 126 compounds of the structural type T-2, wherein Y is S, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 194:
This table covers 126 compounds of the structural type T-2, wherein Y is S, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 195:
This table covers 126 compounds of the structural type T-2, wherein Y is S, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 196:
This table covers 126 compounds of the structural type T-2, wherein Y is S, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 197:
This table covers 126 compounds of the structural type T-2, wherein Y is S, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 198:
This table covers 126 compounds of the structural type T-2, wherein Y is S, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 199:
This table covers 126 compounds of the structural type T-2, wherein Y is S, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 200:
This table covers 126 compounds of the structural type T-2, wherein Y is S, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 201:
This table covers 126 compounds of the structural type T-2, wherein Y is S, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 202:
This table covers 126 compounds of the structural type T-2, wherein Y is S, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 203:
This table covers 126 compounds of the structural type T-2, wherein Y is S, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 204:
This table covers 126 compounds of the structural type T-2, wherein Y is S, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 205:
This table covers 126 compounds of the structural type T-2, wherein Y is S(O), $R^1$, $R^2$, $R^3$ and $R^4$ are hydrogen, G is hydrogen and $R^7$, $R^8$ and $R^{14}$ are as defined in Table 1

Table 206:
This table covers 126 compounds of the structural type T-2, wherein Y is S(O), $R^1$ is methyl $R^2$, $R^3$ and $R^4$ are hydrogen, G is hydrogen and $R^7$, $R^8$ and $R^{14}$ are as defined in Table 1.

Table 207:
This table covers 126 compounds of the structural type T-2, wherein Y is S(O), $R^1$ and $R^2$ are methyl, $R^3$ and $R^4$ are hydrogen, G is hydrogen and $R^7$, $R^8$ and $R^{14}$ are as defined in Table 1.

Table 208:
This table covers 126 compounds of the structural type T-2, wherein Y is S(O), $R^1$ and $R^3$ are methyl, $R^2$ and $R^4$ are hydrogen, G is hydrogen and $R^7$, $R^8$ and $R^{14}$ are as defined in Table 1.

Table 209:
This table covers 126 compounds of the structural type T-2, wherein Y is S(O), $R^1$, $R^2$, and $R^3$ are methyl, $R^4$ is hydrogen, G is hydrogen and $R^7$, $R^8$ and $R^{14}$ are as defined in Table 1.

Table 210:
This table covers 126 compounds of the structural type T-2, wherein Y is S(O), $R^1$, $R^2$, $R^3$ and $R^4$ are methyl, G is hydrogen and $R^7$, $R^8$ and $R^{14}$ are as defined in Table 1.

Table 211:
This table covers 126 compounds of the structural type T-2, wherein Y is S(O), $R^1$ is ethyl, $R^2$, $R^3$ and $R^4$ are hydrogen, G is hydrogen and $R^7$, $R^8$ and $R^{14}$ are as defined in Table 1.

Table 212:
This table covers 126 compounds of the structural type T-2, wherein Y is S(O), $R^1$ is ethyl, $R^2$ is methyl, $R^3$ and $R^4$ are hydrogen, G is hydrogen and $R^7$, $R^8$ and $R^{14}$ are as defined in Table 1.

Table 213:
This table covers 126 compounds of the structural type T-2, wherein Y is S(O), $R^1$ is ethyl, $R^2$ and $R^3$ are hydrogen, $R^4$ is methyl, G is hydrogen and $R^7$, $R^8$ and $R^{14}$ are as defined in Table 1.

Table 214:
This table covers 126 compounds of the structural type T-2, wherein Y is S(O), $R^1$ is ethyl, $R^2$ and $R^3$ are methyl, $R^4$ is hydrogen, G is hydrogen and $R^7$, $R^8$ and $R^{14}$ are as defined in Table 1.

Table 215:
This table covers 126 compounds of the structural type T-2, wherein Y is S(O), $R^1$ is ethyl, $R^2$ is hydrogen, $R^3$ and $R^4$ are methyl, G is hydrogen and $R^7$, $R^8$ and $R^{14}$ are as defined in Table 1.

Table 216:
This table covers 126 compounds of the structural type T-2, wherein Y is S(O), $R^1$ is ethyl, $R^2$, $R^3$ and $R^4$ are methyl, G is hydrogen and $R^7$, $R^8$ and $R^{14}$ are as defined in Table 1.

Table 217:
This table covers 126 compounds of the structural type T-2, wherein Y is S(O), $R^1$ and $R^2$ are ethyl, $R^3$ and $R^4$ are methyl, G is hydrogen and $R^7$, $R^8$ and $R^{14}$ are as defined in Table 1.

Table 218:
This table covers 126 compounds of the structural type T-2, wherein Y is S(O), $R^1$ and $R^3$ are ethyl, $R^2$ and $R^4$ are methyl, G is hydrogen and $R^7$, $R^8$ and $R^{14}$ are as defined in Table 1.

Table 219:
This table covers 126 compounds of the structural type T-2, wherein Y is S(O), $R^1$ and $R^2$ are ethyl, $R^3$ and $R^4$ are hydrogen, G is hydrogen and $R^7$, $R^8$ and $R^{14}$ are as defined in Table 1.

Table 220:
This table covers 126 compounds of the structural type T-2, wherein Y is S(O), $R^1$ and $R^3$ are ethyl, $R^2$ and $R^4$ are hydrogen, G is hydrogen and $R^7$, $R^8$ and $R^{14}$ are as defined in Table 1.

Table 221:
This table covers 126 compounds of the structural type T-2, wherein Y is S(O), $R^1$ and $R^3$ are ethyl, $R^2$ is methyl, $R^4$ is hydrogen, G is hydrogen and $R^7$, $R^8$ and $R^{14}$ are as defined in Table 1.

Table 222:
This table covers 126 compounds of the structural type T-2, wherein Y is S(O), $R^1$ and $R^3$ are ethyl, $R^2$ and $R^4$ are methyl, G is hydrogen and $R^7$, $R^8$ and $R^{14}$ are as defined in Table 1.

Table 223:
This table covers 126 compounds of the structural type T-2, wherein Y is S(O), $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 224:
This table covers 126 compounds of the structural type T-2, wherein Y is S(O), $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 225:
This table covers 126 compounds of the structural type T-2, wherein Y is S(O), $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 226:
This table covers 126 compounds of the structural type T-2, wherein Y is S(O), $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 227:
This table covers 126 compounds of the structural type T-2, wherein Y is S(O), $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 228:
This table covers 126 compounds of the structural type T-2, wherein Y is S(O), $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 229:
This table covers 126 compounds of the structural type T-2, wherein Y is S(O), $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 230:
This table covers 126 compounds of the structural type T-2, wherein Y is S(O), $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 231:
This table covers 126 compounds of the structural type T-2, wherein Y is S(O), $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 232:
This table covers 126 compounds of the structural type T-2, wherein Y is S(O), $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 233:
This table covers 126 compounds of the structural type T-2, wherein Y is S(O), $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 234:
This table covers 126 compounds of the structural type T-2, wherein Y is S(O), $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 235:
This table covers 126 compounds of the structural type T-2, wherein Y is $S(O)_2$, $R^1$, $R^2$, $R^3$ and $R^4$ are hydrogen, G is hydrogen and $R^7$, $R^8$ and $R^{14}$ are as defined in Table 1.

Table 236:
This table covers 126 compounds of the structural type T-2, wherein Y is $S(O)_2$, $R^1$ is methyl $R^2$, $R^3$ and $R^4$ are hydrogen, G is hydrogen and $R^7$, $R^8$ and $R^{14}$ are as defined in Table 1.

Table 237:
This table covers 126 compounds of the structural type T-2, wherein Y is $S(O)_2$, $R^1$ and $R^2$ are methyl, $R^3$ and $R^4$ are hydrogen, G is hydrogen and $R^7$, $R^8$ and $R^{14}$ are as defined in Table 1.

Table 238:
This table covers 126 compounds of the structural type T-2, wherein Y is $S(O)_2$, $R^1$ and $R^3$ are methyl, $R^2$ and $R^4$ are hydrogen, G is hydrogen and $R^7$, $R^8$ and $R^{14}$ are as defined in Table 1.

Table 239:
This table covers 126 compounds of the structural type T-2, wherein Y is $S(O)_2$, $R^1$, $R^2$, and $R^3$ are methyl, $R^4$ is hydrogen, G is hydrogen and $R^7$, $R^8$ and $R^{14}$ are as defined in Table 1.

Table 240:
This table covers 126 compounds of the structural type T-2, wherein Y is $S(O)_2$, $R^1$, $R^2$, $R^3$ and $R^4$ are methyl, G is hydrogen and $R^7$, $R^8$ and $R^{14}$ are as defined in Table 1.

Table 241:
This table covers 126 compounds of the structural type T-2, wherein Y is $S(O)_2$, $R^1$ is ethyl, $R^2$, $R^3$ and $R^4$ are hydrogen, G is hydrogen and $R^7$, $R^8$ and $R^{14}$ are as defined in Table 1.

Table 242:
This table covers 126 compounds of the structural type T-2, wherein Y is $S(O)_2$, $R^1$ is ethyl, $R^2$ is methyl, $R^3$ and $R^4$ are hydrogen, G is hydrogen and $R^7$, $R^8$ and $R^{14}$ are as defined in Table 1.

Table 243:
This table covers 126 compounds of the structural type T-2, wherein Y is $S(O)_2$, $R^1$ is ethyl, $R^2$ and $R^3$ are hydrogen, $R^4$ is methyl, G is hydrogen and $R^7$, $R^8$ and $R^{14}$ are as defined in Table 1.

Table 244:
This table covers 126 compounds of the structural type T-2, wherein Y is $S(O)_2$, $R^1$ is ethyl, $R^2$ and $R^3$ are methyl, $R^4$ is hydrogen, G is hydrogen and $R^7$, $R^8$ and $R^{14}$ are as defined in Table 1.

Table 245:
This table covers 126 compounds of the structural type T-2, wherein Y is $S(O)_2$, $R^1$ is ethyl, $R^2$ is hydrogen, $R^3$ and $R^4$ are methyl, G is hydrogen and $R^7$, $R^8$ and $R^{14}$ are as defined in Table 1.

Table 246:
This table covers 126 compounds of the structural type T-2, wherein Y is $S(O)_2$, $R^1$ is ethyl, $R^2$, $R^3$ and $R^4$ are methyl, G is hydrogen and $R^7$, $R^8$ and $R^{14}$ are as defined in Table 1.

Table 247:
This table covers 126 compounds of the structural type T-2, wherein Y is $S(O)_2$, $R^1$ and $R^2$ are ethyl, $R^3$ and $R^4$ are methyl, G is hydrogen and $R^7$, $R^8$ and $R^{14}$ are as defined in Table 1.

Table 248:
This table covers 126 compounds of the structural type T-2, wherein Y is $S(O)_2$, $R^1$ and $R^3$ are ethyl, $R^2$ and $R^4$ are methyl, G is hydrogen and $R^7$, $R^8$ and $R^{14}$ are as defined in Table 1.

Table 249:
This table covers 126 compounds of the structural type T-2, wherein Y is $S(O)_2$, $R^1$ and $R^2$ are ethyl, $R^3$ and $R^4$ are hydrogen, G is hydrogen and $R^7$, $R^8$ and $R^{14}$ are as defined in Table 1.

Table 250:
This table covers 126 compounds of the structural type T-2, wherein Y is $S(O)_2$, $R^1$ and $R^3$ are ethyl, $R^2$ and $R^4$ are hydrogen, G is hydrogen and $R^7$, $R^8$ and $R^{14}$ are as defined in Table 1.

Table 251:
This table covers 126 compounds of the structural type T-2, wherein Y is $S(O)_2$, $R^1$ and $R^3$ are ethyl, $R^2$ is methyl, $R^4$ is hydrogen, G is hydrogen and $R^7$, $R^8$ and $R^{14}$ are as defined in Table 1.

Table 252:
This table covers 126 compounds of the structural type T-2, wherein Y is $S(O)_2$, $R^1$ and $R^3$ are ethyl, $R^2$ and $R^4$ are methyl, G is hydrogen and $R^7$, $R^8$ and $R^{14}$ are as defined in Table 1.

Table 253:
This table covers 126 compounds of the structural type T-2, wherein Y is $S(O)_2$, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 254:
This table covers 126 compounds of the structural type T-2, wherein Y is $S(O)_2$, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 255:
This table covers 126 compounds of the structural type T-2, wherein Y is $S(O)_2$, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 256:
This table covers 126 compounds of the structural type T-2, wherein Y is $S(O)_2$, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 257:
This table covers 126 compounds of the structural type T-2, wherein Y is $S(O)_2$, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 258:
This table covers 126 compounds of the structural type T-2, wherein Y is $S(O)_2$, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 259:
This table covers 126 compounds of the structural type T-2, wherein Y is $S(O)_2$, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 260:
This table covers 126 compounds of the structural type T-2, wherein Y is $S(O)_2$, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 261:
This table covers 126 compounds of the structural type T-2, wherein Y is $S(O)_2$, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 262:
This table covers 126 compounds of the structural type T-2, wherein Y is $S(O)_2$, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 263:
This table covers 126 compounds of the structural type T-2, wherein Y is $S(O)_2$, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 264:
This table covers 126 compounds of the structural type T-2, wherein Y is $S(O)_2$, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 265:
This table covers 126 compounds of the structural type T-2, wherein Y is C=O, $R^1$ and $R^2$ are methyl, $R^3$ and $R^4$ are hydrogen, G is hydrogen and $R^7$, $R^8$ and $R^{14}$ are as defined in Table 1.

Table 266:
This table covers 126 compounds of the structural type T-2, wherein Y is C=O, $R^1$, $R^2$, and $R^3$ are methyl, $R^4$ is hydrogen, G is hydrogen and $R^7$, $R^8$ and $R^{14}$ are as defined in Table 1.

Table 267:
This table covers 126 compounds of the structural type T-2, wherein Y is C=O, $R^1$, $R^2$, $R^3$ and $R^4$ are methyl, G is hydrogen and $R^7$, $R^8$ and $R^{14}$ are as defined in Table 1.

Table 268:
This table covers 126 compounds of the structural type T-2, wherein Y is C=O, $R^1$ is ethyl, $R^2$ is methyl, $R^3$ and $R^4$ are hydrogen, G is hydrogen and $R^7$, $R^8$ and $R^{14}$ are as defined in Table 1.

Table 269:
This table covers 126 compounds of the structural type T-2, wherein Y is C=O, $R^1$ is ethyl, $R^2$ and $R^3$ are methyl, $R^4$ is hydrogen, G is hydrogen and $R^7$, $R^8$ and $R^{14}$ are as defined in Table 1.

Table 270:
This table covers 126 compounds of the structural type T-2, wherein Y is C=O, $R^1$ is ethyl, $R^2$ is hydrogen, $R^3$ and $R^4$ are methyl, G is hydrogen and $R^7$, $R^8$ and $R^{14}$ are as defined in Table 1.

Table 271:
This table covers 126 compounds of the structural type T-2, wherein Y is C=O, $R^1$ is ethyl, $R^2$, $R^3$ and $R^4$ are methyl, G is hydrogen and $R^7$, $R^8$ and $R^{14}$ are as defined in Table 1.

Table 272:
This table covers 126 compounds of the structural type T-2, wherein Y is C=O, $R^1$ and $R^2$ are ethyl, $R^3$ and $R^4$ are methyl, G is hydrogen and $R^7$, $R^8$ and $R^{14}$ are as defined in Table 1.

Table 273:
This table covers 126 compounds of the structural type T-2, wherein Y is C=O, $R^1$ and $R^3$ are ethyl, $R^2$ and $R^4$ are methyl, G is hydrogen and $R^7$, $R^8$ and $R^{14}$ are as defined in Table 1.

Table 274:
This table covers 126 compounds of the structural type T-2, wherein Y is C=O, $R^1$ and $R^2$ are ethyl, $R^3$ and $R^4$ are hydrogen, G is hydrogen and $R^7$, $R^8$ and $R^{14}$ are as defined in Table 1.

Table 275:
This table covers 126 compounds of the structural type T-2, wherein Y is C=O, $R^1$ and $R^2$ are ethyl, $R^3$ is methyl, $R^4$ is hydrogen, G is hydrogen and $R^7$, $R^8$ and $R^{14}$ are as defined in Table 1.

Table 276:
This table covers 126 compounds of the structural type T-2, wherein Y is C=O, $R^1$ and $R^3$ are ethyl, $R^2$ and $R^4$ are methyl, G is hydrogen and $R^7$, $R^8$ and $R^{14}$ are as defined in Table 1.

Table 277:
This table covers 126 compounds of the structural type T-2, wherein Y is C=O, $R^1$ and $R^2$, together with the carbon to which they are attached, are joined to form a cyclopropane ring, $R^3$ and $R^4$ are hydrogen, G is hydrogen and $R^7$, $R^8$ and $R^{14}$ are as defined in Table 1.

Table 278:
This table covers 126 compounds of the structural type T-2, wherein Y is C=O, $R^1$ and $R^2$, together with the carbon to which they are attached, are joined to form a cyclobutane ring, $R^3$ and $R^4$ are hydrogen, G is hydrogen and $R^7$, $R^8$ and $R^{14}$ are as defined in Table 1.

Table 279:
This table covers 126 compounds of the structural type T-2, wherein Y is C=O, $R^1$ and $R^2$, together with the carbon to which they are attached, are joined to form a cyclopentane ring, $R^3$ and $R^4$ are hydrogen, G is hydrogen and $R^7$, $R^8$ and $R^{14}$ are as defined in Table 1.

Table 280:
This table covers 126 compounds of the structural type T-2, wherein Y is C=O, $R^1$ and $R^2$, together with the carbon to which they are attached, are joined to form a cyclohexane ring, $R^3$ and $R^4$ are hydrogen, G is hydrogen and $R^7$, $R^8$ and $R^{14}$ are as defined in Table 1.

Table 281:
This table covers 126 compounds of the structural type T-2, wherein Y is C=O, $R^1$ and $R^2$, together with the carbon to which they are attached, are joined to form a cyclopropane ring, $R^3$ is hydrogen, $R^4$ is methyl, G is hydrogen and $R^7$, $R^8$ and $R^{14}$ are as defined in Table 1.

Table 282:
This table covers 126 compounds of the structural type T-2, wherein Y is C=O, $R^1$ and $R^2$, together with the carbon to which they are attached, are joined to form a cyclobutane ring, $R^3$ is hydrogen, $R^4$ is methyl, G is hydrogen and $R^7$, $R^8$ and $R^{14}$ are as defined in Table 1.

Table 283:
This table covers 126 compounds of the structural type T-2, wherein Y is C=O, $R^1$ and $R^2$, together with the carbon to which they are attached, are joined to form a cyclopentane ring, $R^3$ is hydrogen, $R^4$ is methyl, G is hydrogen and $R^7$, $R^8$ and $R^{14}$ are as defined in Table 1.

Table 284:
This table covers 126 compounds of the structural type T-2, wherein Y is C=O, $R^1$ and $R^2$, together with the carbon to which they are attached, are joined to form a cyclohexane ring, $R^3$ is hydrogen, $R^4$ is methyl, G is hydrogen and $R^7$, $R^8$ and $R^{14}$ are as defined in Table 1.

Table 285:
This table covers 126 compounds of the structural type T-2, wherein Y is C=O, $R^1$ and $R^2$, together with the carbon to which they are attached, are joined to form a cyclopropane ring, $R^3$ and $R^4$ are methyl, G is hydrogen and $R^7$, $R^8$ and $R^{14}$ are as defined in Table 1.

Table 286:
This table covers 126 compounds of the structural type T-2, wherein Y is C=O, $R^1$ and $R^2$, together with the carbon to which they are attached, are joined to form a cyclobutane ring, $R^3$ and $R^4$ are methyl, G is hydrogen and $R^7$, $R^8$ and $R^{14}$ are as defined in Table 1.

Table 287:
This table covers 126 compounds of the structural type T-2, wherein Y is C=O, $R^1$ and $R^2$, together with the carbon to which they are attached, are joined to form a cyclopentane ring, $R^3$ and $R^4$ are methyl, G is hydrogen and $R^7$, $R^8$ and $R^{14}$ are as defined in Table 1.

Table 288:
This table covers 126 compounds of the structural type T-2, wherein Y is C=O, $R^1$ and $R^2$, together with the carbon to which they are attached, are joined to form a cyclohexane ring, $R^3$ and $R^4$ are methyl, G is hydrogen and $R^7$, $R^8$ and $R^{14}$ are as defined in Table 1.

Table 289:
This table covers 118 compounds of structural type T-3:

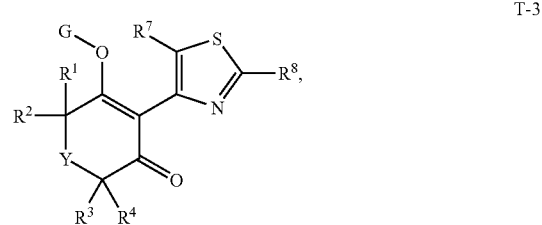

wherein Y is O, $R^1$, $R^2$, $R^3$ and $R^4$ are hydrogen, G is hydrogen and $R^7$ and $R^8$ are as defined below:

| Compound Number | $R^7$ | $R^8$ |
|---|---|---|
| 289.001 | $CH_3$ | H |
| 289.002 | $CH_3$ | $CH_3$ |
| 289.003 | $CH_3$ | $CH_3CH_2$ |
| 289.004 | $CH_3CH_2$ | H |
| 289.005 | $CH_3CH_2$ | $CH_3$ |
| 289.006 | $CH_3CH_2$ | $CH_3CH_2$ |
| 289.007 | $CH_3$ | phenyl |
| 289.008 | $CH_3$ | 2-fluorophenyl |
| 289.009 | $CH_3$ | 3-fluorophenyl |
| 289.010 | $CH_3$ | 4-fluorophenyl |
| 289.011 | $CH_3$ | 2-chlorophenyl |
| 289.012 | $CH_3$ | 3-chlorophenyl |
| 289.013 | $CH_3$ | 4-chlorophenyl |
| 289.014 | $CH_3$ | 2-bromophenyl |
| 289.015 | $CH_3$ | 3-bromophenyl |
| 289.016 | $CH_3$ | 4-bromophenyl |
| 289.017 | $CH_3$ | 2-methylphenyl |
| 289.018 | $CH_3$ | 3-methylphenyl |
| 289.019 | $CH_3$ | 4-methylphenyl |
| 289.020 | $CH_3$ | 2-cyanophenyl |
| 289.021 | $CH_3$ | 3-cyanophenyl |
| 289.022 | $CH_3$ | 4-cyanophenyl |
| 289.023 | $CH_3$ | 2-methoxyphenyl |
| 289.024 | $CH_3$ | 3-methoxyphenyl |
| 289.025 | $CH_3$ | 4-methoxyphenyl |
| 289.026 | $CH_3$ | 2-trifluoromethylphenyl |
| 289.027 | $CH_3$ | 3-trifluoromethylphenyl |
| 289.028 | $CH_3$ | 4-trifluoromethylphenyl |
| 289.029 | $CH_3$ | 4-trifluoromethoxyphenyl |
| 289.030 | $CH_3$ | 4-difluoromethoxyphenyl |
| 289.031 | $CH_3$ | 4-methylthiophenyl |
| 289.032 | $CH_3$ | 4-methylsulfinylphenyl |
| 289.033 | $CH_3$ | 4-methylsulfonylphenyl |
| 289.034 | $CH_3$ | 4-trifluoromethylthiophenyl |
| 289.035 | $CH_3$ | 4-trifluoromethylsulfinylphenyl |
| 289.036 | $CH_3$ | 4-trifluoromethylsulfonylphenyl |
| 289.037 | $CH_3$ | 2,3-difluorophenyl |
| 289.038 | $CH_3$ | 2,4-difluorophenyl |

| Compound Number | R⁷ | R⁸ |
|---|---|---|
| 289.039 | CH₃ | 2,5-difluorophenyl |
| 289.040 | CH₃ | 2,6-difluorophenyl |
| 289.041 | CH₃ | 3,4-difluorophenyl |
| 289.042 | CH₃ | 3,5-difluorophenyl |
| 289.043 | CH₃ | 2,3-dichlorophenyl |
| 289.044 | CH₃ | 2,4-dichlorophenyl |
| 289.045 | CH₃ | 2,5-dichlorophenyl |
| 289.046 | CH₃ | 2,6-dichlorophenyl |
| 289.047 | CH₃ | 3,4-dichlorophenyl |
| 289.048 | CH₃ | 3,5-dichlorophenyl |
| 289.049 | CH₃ | 4-chloro-2-fluorophenyl |
| 289.050 | CH₃ | 4-chloro-3-fluorophenyl |
| 289.051 | CH₃ | 4-chloro-2-methylphenyl |
| 289.052 | CH₃ | 4-chloro-3-methylphenyl |
| 289.053 | CH₃ | 2-fluoro-4-trifluoromethylphenyl |
| 289.054 | CH₃ | 3-fluoro-4-trifluoromethylphenyl |
| 289.055 | CH₃ | 2-chloropyridin-5-yl |
| 289.056 | CH₃ | 3-chloropyridinyl-5-yl |
| 289.057 | CH₃ | 2-methylpyridin-5-yl |
| 289.058 | CH₃ | 3-methylpyridinyl-5-yl |
| 289.059 | CH₃ | 2-trifluoromethylpyridin-5-yl |
| 289.060 | CH₃ | 3-trifluoromethylpyridin-5-yl |
| 289.061 | CH₃ | 2,6-dichloropyridin-3-yl |
| 289.062 | CH₃ | 4-chloropyrazol-1-yl |
| 289.063 | CH₃CH₂ | phenyl |
| 289.064 | CH₃CH₂ | 2-fluorophenyl |
| 289.065 | CH₃CH₂ | 3-fluorophenyl |
| 289.066 | CH₃CH₂ | 4-fluorophenyl |
| 289.067 | CH₃CH₂ | 2-chlorophenyl |
| 289.068 | CH₃CH₂ | 3-chlorophenyl |
| 289.069 | CH₃CH₂ | 4-chlorophenyl |
| 289.070 | CH₃CH₂ | 2-bromophenyl |
| 289.071 | CH₃CH₂ | 3-bromophenyl |
| 289.072 | CH₃CH₂ | 4-bromophenyl |
| 289.073 | CH₃CH₂ | 2-methylphenyl |
| 289.074 | CH₃CH₂ | 3-methylphenyl |
| 289.075 | CH₃CH₂ | 4-methylphenyl |
| 289.076 | CH₃CH₂ | 2-cyanophenyl |
| 289.077 | CH₃CH₂ | 3-cyanophenyl |
| 289.078 | CH₃CH₂ | 4-cyanophenyl |
| 289.079 | CH₃CH₂ | 2-methoxyphenyl |
| 289.080 | CH₃CH₂ | 3-methoxyphenyl |
| 289.081 | CH₃CH₂ | 4-methoxyphenyl |
| 289.082 | CH₃CH₂ | 2-trifluoromethylphenyl |
| 289.083 | CH₃CH₂ | 3-trifluoromethylphenyl |
| 289.084 | CH₃CH₂ | 4-trifluoromethylphenyl |
| 289.085 | CH₃CH₂ | 4-trifluoromethoxyphenyl |
| 289.086 | CH₃CH₂ | 4-difluoromethoxyphenyl |
| 289.087 | CH₃CH₂ | 4-methylthiophenyl |
| 289.088 | CH₃CH₂ | 4-methylsulfinylphenyl |
| 289.089 | CH₃CH₂ | 4-methylsulfonylphenyl |
| 289.090 | CH₃CH₂ | 4-trifluoromethylthiophenyl |
| 289.091 | CH₃CH₂ | 4-trifluoromethylsulfinylphenyl |
| 289.092 | CH₃CH₂ | 4-trifluoromethylsulfonylphenyl |
| 289.093 | CH₃CH₂ | 2,3-difluorophenyl |
| 289.094 | CH₃CH₂ | 2,4-difluorophenyl |
| 289.095 | CH₃CH₂ | 2,5-difluorophenyl |
| 289.096 | CH₃CH₂ | 2,6-difluorophenyl |
| 289.097 | CH₃CH₂ | 3,4-difluorophenyl |
| 289.098 | CH₃CH₂ | 3,5-difluorophenyl |
| 289.099 | CH₃CH₂ | 2,3-dichlorophenyl |
| 289.100 | CH₃CH₂ | 2,4-dichlorophenyl |
| 289.101 | CH₃CH₂ | 2,5-dichlorophenyl |
| 289.102 | CH₃CH₂ | 2,6-dichlorophenyl |
| 289.103 | CH₃CH₂ | 3,4-dichlorophenyl |
| 289.104 | CH₃CH₂ | 3,5-dichlorophenyl |
| 289.105 | CH₃CH₂ | 4-chloro-2-fluorophenyl |
| 289.106 | CH₃CH₂ | 4-chloro-3-fluorophenyl |
| 289.107 | CH₃CH₂ | 4-chloro-2-methylphenyl |
| 289.108 | CH₃CH₂ | 4-chloro-3-methylphenyl |
| 289.109 | CH₃CH₂ | 2-fluoro-4-trifluoromethylphenyl |
| 289.110 | CH₃CH₂ | 3-fluoro-4-trifluoromethylphenyl |
| 289.111 | CH₃CH₂ | 2-chloropyridin-5-yl |
| 289.112 | CH₃CH₂ | 3-chloropyridinyl-5-yl |
| 289.113 | CH₃CH₂ | 2-methylpyridin-5-yl |
| 289.114 | CH₃CH₂ | 3-methylpyridinyl-5-yl |
| 289.115 | CH₃CH₂ | 2-trifluoromethylpyridin-5-yl |
| 289.116 | CH₃CH₂ | 3-trifluoromethylpyridin-5-yl |
| 289.117 | CH₃CH₂ | 2,6-dichloropyridin-3-yl |
| 289.118 | CH₃CH₂ | 4-chloropyrazol-1-yl |

Table 290:

This table covers 118 compounds of structural type T-3, wherein Y is O, $R^1$ is methyl $R^2$, $R^3$ and $R^4$ are hydrogen, G is hydrogen and $R^7$ and $R^8$ are as defined in Table 289.

Table 291:

This table covers 118 compounds of structural type T-3, wherein Y is O, $R^1$ and $R^2$ are methyl, $R^3$ and $R^4$ are hydrogen, G is hydrogen and $R^7$ and $R^8$ are as defined in Table 289.

Table 292:

This table covers 118 compounds of structural type T-3, wherein Y is O, $R^1$ and $R^3$ are methyl, $R^2$ and $R^4$ are hydrogen, G is hydrogen and $R^7$ and $R^8$ are as defined in Table 289.

Table 293

This table covers 118 compounds of structural type T-3, wherein Y is O, $R^1$, $R^2$, and $R^3$ are methyl, $R^4$ is hydrogen, G is hydrogen and $R^7$ and $R^8$ are as defined in Table 289.

Table 294:

This table covers 118 compounds of structural type T-3, wherein Y is O, Fe, $R^2$, $R^3$ and $R^4$ are methyl, G is hydrogen and $R^7$ and $R^8$ are as defined in Table 289.

Table 295:

This table covers 118 compounds of structural type T-3, wherein Y is O, $R^1$ is ethyl, $R^2$, $R^3$ and $R^4$ are hydrogen, G is hydrogen and $R^7$ and $R^8$ are as defined in Table 88:

Table 296:

This table covers 118 compounds of structural type T-3, wherein Y is O, $R^1$ is ethyl, $R^2$ is methyl, $R^3$ and $R^4$ are hydrogen, G is hydrogen and $R^7$ and $R^8$ are as defined in Table 289.

Table 297:

This table covers 118 compounds of structural type T-3, wherein Y is O, $R^1$ is ethyl, $R^2$ and $R^3$ are hydrogen, $R^4$ is methyl, G is hydrogen and $R^7$ and $R^8$ are as defined in Table 289.

Table 298:

This table covers 118 compounds of structural type T-3, wherein Y is O, $R^1$ is ethyl, $R^2$ and $R^3$ are methyl, $R^4$ is hydrogen, G is hydrogen and $R^7$ and $R^8$ are as defined in Table 289.

Table 299:

This table covers 118 compounds of structural type T-3, wherein Y is O, $R^1$ is ethyl, $R^2$ is hydrogen, $R^3$ and $R^4$ are methyl, G is hydrogen and $R^7$ and $R^8$ are as defined in Table 289.

Table 300:

This table covers 118 compounds of structural type T-3, wherein Y is O, $R^1$ is ethyl, $R^2$, $R^3$ and $R^4$ are methyl, G is hydrogen and $R^7$ and $R^8$ are as defined in Table 289.

Table 301:

This table covers 118 compounds of structural type T-3, wherein Y is O, $R^1$ and $R^2$ are ethyl, $R^3$ and $R^4$ are methyl, G is hydrogen and $R^7$ and $R^8$ are as defined in Table 289.

Table 302:

This table covers 118 compounds of structural type T-3, wherein Y is O, $R^1$ and $R^3$ are ethyl, $R^2$ and $R^4$ are methyl, G is hydrogen and $R^7$ and $R^8$ are as defined in Table 289.

Table 303:
This table covers 118 compounds of structural type T-3, wherein Y is O, $R^1$ and $R^2$ are ethyl, $R^3$ and $R^4$ are hydrogen, G is hydrogen and $R^7$ and $R^8$ are as defined in Table 289.

Table 304:
This table covers 118 compounds of structural type T-3, wherein Y is O, $R^1$ and $R^3$ are ethyl, $R^2$ and $R^4$ are hydrogen, G is hydrogen and $R^7$ and $R^8$ are as defined in Table 289.

Table 305:
This table covers 118 compounds of structural type T-3, wherein Y is O, $R^1$ and $R^3$ are ethyl, $R^2$ is methyl, $R^4$ is hydrogen, G is hydrogen and $R^7$ and $R^8$ are as defined in Table 289.

Table 306:
This table covers 118 compounds of structural type T-3, wherein Y is O, $R^1$ and $R^3$ are ethyl, $R^2$ and $R^4$ are methyl, G is hydrogen and $R^7$ and $R^8$ are as defined in Table 289.

Table 307:
This table covers 118 compounds of structural type T-3, wherein Y is O, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 308:
This table covers 118 compounds of structural type T-3, wherein Y is O, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 309:
This table covers 118 compounds of structural type T-3, wherein Y is O, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 310:
This table covers 118 compounds of structural type T-3, wherein Y is O, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 311:
This table covers 118 compounds of structural type T-3, wherein Y is O, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 312:
This table covers 118 compounds of structural type T-3, wherein Y is O, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 313:
This table covers 118 compounds of structural type T-3, wherein Y is O, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 314:
This table covers 118 compounds of structural type T-3, wherein Y is O, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 315:
This table covers 118 compounds of structural type T-3, wherein Y is O, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 316:
This table covers 118 compounds of structural type T-3, wherein Y is O, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 317:
This table covers 118 compounds of structural type T-3, wherein Y is O, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 318:
This table covers 118 compounds of structural type T-3, wherein Y is O, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 319:
This table covers 118 compounds of structural type T-3, wherein Y is S, $R^1$, $R^2$, $R^3$ and $R^4$ are hydrogen, G is hydrogen and $R^7$ and $R^8$ are as defined in Table 289.

Table 320:
This table covers 118 compounds of structural type T-3, wherein Y is S, $R^1$ is methyl $R^2$, $R^3$ and $R^4$ are hydrogen, G is hydrogen and $R^7$ and $R^8$ are as defined in Table 289.

Table 321:
This table covers 118 compounds of structural type T-3, wherein Y is S, $R^1$ and $R^2$ are methyl, R3 and $R^4$ are hydrogen, G is hydrogen and $R^7$ and $R^8$ are as defined in Table 289.

Table 322:
This table covers 118 compounds of structural type T-3, wherein Y is S, $R^1$ and $R^3$ are methyl, $R^2$ and $R^4$ are hydrogen, G is hydrogen and $R^7$ and $R^8$ are as defined in Table 289.

Table 323:
This table covers 118 compounds of structural type T-3, wherein Y is S, $R^1$, $R^2$, and $R^3$ are methyl, $R^4$ is hydrogen, G is hydrogen and $R^7$ and $R^8$ are as defined in Table 289.

Table 324:
This table covers 118 compounds of structural type T-3, wherein Y is S, $R^1$, $R^2$, $R^3$ and $R^4$ are methyl, G is hydrogen and $R^7$ and $R^8$ are as defined in Table 289.

Table 325:
This table covers 118 compounds of structural type T-3, wherein Y is S, $R^1$ is ethyl, $R^2$, $R^3$ and $R^4$ are hydrogen, G is hydrogen and $R^7$ and $R^8$ are as defined in Table 289.

Table 326:
This table covers 118 compounds of structural type T-3, wherein Y is S, $R^1$ is ethyl, $R^2$ is methyl, $R^3$ and $R^4$ are hydrogen, G is hydrogen and $R^7$ and $R^8$ are as defined in Table 289.

Table 327:
This table covers 118 compounds of structural type T-3, wherein Y is S, $R^1$ is ethyl, $R^2$ and R3 are hydrogen, $R^4$ is methyl, G is hydrogen and $R^7$ and $R^8$ are as defined in Table 289.

Table 328:
This table covers 118 compounds of structural type T-3, wherein Y is S, $R^1$ is ethyl, $R^2$ and $R^3$ are methyl, $R^4$ is hydrogen, G is hydrogen and $R^7$ and $R^8$ are as defined in Table 289.

Table 329:
This table covers 118 compounds of structural type T-3, wherein Y is S, $R^1$ is ethyl, $R^2$ is hydrogen, $R^3$ and $R^4$ are methyl, G is hydrogen and $R^7$ and $R^8$ are as defined in Table 289.

Table 330:
This table covers 118 compounds of structural type T-3, wherein Y is S, $R^1$ is ethyl, $R^2$, $R^3$ and $R^4$ are methyl, G is hydrogen and $R^7$ and $R^8$ are as defined in Table 289.

Table 331:
This table covers 118 compounds of structural type T-3, wherein Y is S, $R^1$ and $R^2$ are ethyl, $R^3$ and $R^4$ are methyl, G is hydrogen and $R^7$ and $R^8$ are as defined in Table 289.

Table 332:
This table covers 118 compounds of structural type T-3, wherein Y is S, $R^1$ and $R^3$ are ethyl, $R^2$ and $R^4$ are methyl, G is hydrogen and $R^7$ and $R^8$ are as defined in Table 289.

Table 333:
This table covers 118 compounds of structural type T-3, wherein Y is S, $R^1$ and $R^2$ are ethyl, $R^3$ and $R^4$ are hydrogen, G is hydrogen and $R^7$ and $R^8$ are as defined in Table 289.

Table 334:
This table covers 118 compounds of structural type T-3, wherein Y is S, $R^1$ and $R^3$ are ethyl, $R^2$ and $R^4$ are hydrogen, G is hydrogen and $R^7$ and $R^8$ are as defined in Table 289.

Table 335:
This table covers 118 compounds of structural type T-3, wherein Y is S, $R^1$ and $R^3$ are ethyl, $R^2$ is methyl, $R^4$ is hydrogen, G is hydrogen and $R^7$ and $R^8$ are as defined in Table 289.

Table 336:
This table covers 118 compounds of structural type T-3, wherein Y is S, $R^1$ and $R^3$ are ethyl, $R^2$ and $R^4$ are methyl, G is hydrogen and $R^7$ and $R^8$ are as defined in Table 289.

Table 337:
This table covers 118 compounds of structural type T-3, wherein Y is S, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 338:
This table covers 118 compounds of structural type T-3, wherein Y is S, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 339:
This table covers 118 compounds of structural type T-3, wherein Y is S, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 340:
This table covers 118 compounds of structural type T-3, wherein Y is S, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 341:
This table covers 118 compounds of structural type T-3, wherein Y is S, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 342:
This table covers 118 compounds of structural type T-3, wherein Y is S, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 343:
This table covers 118 compounds of structural type T-3, wherein Y is S, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 344:
This table covers 118 compounds of structural type T-3, wherein Y is S, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 345:
This table covers 118 compounds of structural type T-3, wherein Y is S, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 346:
This table covers 118 compounds of structural type T-3, wherein Y is S, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 347:
This table covers 118 compounds of structural type T-3, wherein Y is S, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 348:
This table covers 118 compounds of structural type T-3, wherein Y is S, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 349:
This table covers 118 compounds of structural type T-3, wherein Y is S(O), $R^1$, $R^2$, $R^3$ and $R^4$ are hydrogen, G is hydrogen and $R^7$ and $R^8$ are as defined in Table 289.

Table 350:
This table covers 118 compounds of structural type T-3, wherein Y is S(O), $R^1$ is methyl $R^2$, $R^3$ and $R^4$ are hydrogen, G is hydrogen and $R^7$ and $R^8$ are as defined in Table 289.

Table 351:
This table covers 118 compounds of structural type T-3, wherein Y is S(O), $R^1$ and $R^2$ are methyl, $R^3$ and $R^4$ are hydrogen, G is hydrogen and $R^7$ and $R^8$ are as defined in Table 289.

Table 352:
This table covers 118 compounds of structural type T-3, wherein Y is S(O), $R^1$ and $R^3$ are methyl, $R^2$ and $R^4$ are hydrogen, G is hydrogen and $R^7$ and $R^8$ are as defined in Table 289.

Table 353:
This table covers 118 compounds of structural type T-3, wherein Y is S(O), $R^1$, $R^2$, and $R^3$ are methyl, $R^4$ is hydrogen, G is hydrogen and $R^7$ and $R^8$ are as defined in Table 289.

Table 354:
This table covers 118 compounds of structural type T-3, wherein Y is S(O), $R^1$, $R^2$, $R^3$ and $R^4$ are methyl, G is hydrogen and $R^7$ and $R^8$ are as defined in Table 289.

Table 355:
This table covers 118 compounds of structural type T-3, wherein Y is S(O), $R^1$ is ethyl, $R^2$, $R^3$ and $R^4$ are hydrogen, G is hydrogen and $R^7$ and $R^8$ are as defined in Table 289.

Table 356:
This table covers 118 compounds of structural type T-3, wherein Y is S(O), $R^1$ is ethyl, $R^2$ is methyl, $R^3$ and $R^4$ are hydrogen, G is hydrogen and $R^7$ and $R^8$ are as defined in Table 289.

Table 357:
This table covers 118 compounds of structural type T-3, wherein Y is S(O), Fe is ethyl, $R^2$ and $R^3$ are hydrogen, $R^4$ is methyl, G is hydrogen and $R^7$ and $R^8$ are as defined in Table 289.

Table 358:
This table covers 118 compounds of structural type T-3, wherein Y is S(O), $R^1$ is ethyl, $R^2$ and $R^3$ are methyl, $R^4$ is hydrogen, G is hydrogen and $R^7$ and $R^8$ are as defined in Table 289.

Table 359:
This table covers 118 compounds of structural type T-3, wherein Y is S(O), $R^1$ is ethyl, $R^2$ is hydrogen, $R^3$ and $R^4$ are methyl, G is hydrogen and $R^7$ and $R^8$ are as defined in Table 289.

Table 360:
This table covers 118 compounds of structural type T-3, wherein Y is S(O), $R^1$ is ethyl, $R^2$, $R^3$ and $R^4$ are methyl, G is hydrogen and $R^7$ and $R^8$ are as defined in Table 289.

Table 361:
This table covers 118 compounds of structural type T-3, wherein Y is S(O), $R^1$ and $R^2$ are ethyl, $R^3$ and $R^4$ are methyl, G is hydrogen and $R^7$ and $R^8$ are as defined in Table 289.

Table 362:
This table covers 118 compounds of structural type T-3, wherein Y is S(O), $R^1$ and $R^3$ are ethyl, $R^2$ and $R^4$ are methyl, G is hydrogen and $R^7$ and $R^8$ are as defined in Table 289.

Table 363:
This table covers 118 compounds of structural type T-3, wherein Y is S(O), $R^1$ and $R^2$ are ethyl, $R^3$ and $R^4$ are hydrogen, G is hydrogen and $R^7$ and $R^8$ are as defined in Table 289.

Table 364:
This table covers 118 compounds of structural type T-3, wherein Y is S(O), $R^1$ and $R^3$ are ethyl, $R^2$ and $R^4$ are hydrogen, G is hydrogen and $R^7$ and $R^8$ are as defined in Table 289.

Table 365:
This table covers 118 compounds of structural type T-3, wherein Y is S(O), $R^1$ and $R^3$ are ethyl, $R^2$ is methyl, $R^4$ is hydrogen, G is hydrogen and $R^7$ and $R^8$ are as defined in Table 289.

Table 366:
This table covers 118 compounds of structural type T-3, wherein Y is S(O), $R^1$ and $R^3$ are ethyl, $R^2$ and $R^4$ are methyl, G is hydrogen and $R^7$ and $R^8$ are as defined in Table 289.

Table 367:
This table covers 118 compounds of structural type T-3, wherein Y is S(O), $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 368:
This table covers 118 compounds of structural type T-3, wherein Y is S(O), $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 369:
This table covers 118 compounds of structural type T-3, wherein Y is S(O), $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 370:
This table covers 118 compounds of structural type T-3, wherein Y is S(O), $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 371:
This table covers 118 compounds of structural type T-3, wherein Y is S(O), $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 372:
This table covers 118 compounds of structural type T-3, wherein Y is S(O), Fe and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 373:
This table covers 118 compounds of structural type T-3, wherein Y is S(O), $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 374:
This table covers 118 compounds of structural type T-3, wherein Y is S(O), $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 375:
This table covers 118 compounds of structural type T-3, wherein Y is S(O), $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 376:
This table covers 118 compounds of structural type T-3, wherein Y is S(O), $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 377:
This table covers 118 compounds of structural type T-3, wherein Y is S(O), $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 378:
This table covers 118 compounds of structural type T-3, wherein Y is S(O), $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 379:
This table covers 118 compounds of structural type T-3, wherein Y is $S(O)_2$, $R^1$, $R^2$, $R^3$ and $R^4$ are hydrogen, G is hydrogen and $R^7$ and $R^8$ are as defined in Table 289.

Table 380:
This table covers 118 compounds of structural type T-3, wherein Y is $S(O)_2$, $R^1$ is methyl $R^2$, $R^3$ and $R^4$ are hydrogen, G is hydrogen and $R^7$ and $R^8$ are as defined in Table 289.

Table 381:
This table covers 118 compounds of structural type T-3, wherein Y is $S(O)_2$, $R^1$ and $R^2$ are methyl, R3 and $R^4$ are hydrogen, G is hydrogen and $R^7$ and $R^8$ are as defined in Table 289.

Table 382:
This table covers 118 compounds of structural type T-3, wherein Y is $S(O)_2$, $R^1$ and $R^3$ are methyl, $R^2$ and $R^4$ are hydrogen, G is hydrogen and $R^7$ and $R^8$ are as defined in Table 289.

Table 383:
This table covers 118 compounds of structural type T-3, wherein Y is $S(O)_2$, $R^1$, $R^2$, and $R^3$ are methyl, $R^4$ is hydrogen, G is hydrogen and $R^7$ and $R^8$ are as defined in Table 289.

Table 384:
This table covers 118 compounds of structural type T-3, wherein Y is $S(O)_2$, Fe, $R^2$, $R^3$ and $R^4$ are methyl, G is hydrogen and $R^7$ and $R^8$ are as defined in Table 289.

Table 385:
This table covers 118 compounds of structural type T-3, wherein Y is $S(O)_2$, $R^1$ is ethyl, $R^2$, $R^3$ and $R^4$ are hydrogen, G is hydrogen and $R^7$ and $R^8$ are as defined in Table 289.

Table 386:
This table covers 118 compounds of structural type T-3, wherein Y is $S(O)_2$, $R^1$ is ethyl, $R^2$ is methyl, $R^3$ and $R^4$ are hydrogen, G is hydrogen and $R^7$ and $R^8$ are as defined in Table 289.

Table 387:
This table covers 118 compounds of structural type T-3, wherein Y is $S(O)_2$, $R^1$ is ethyl, $R^2$ and R3 are hydrogen, $R^4$ is methyl, G is hydrogen and $R^7$ and $R^8$ are as defined in Table 289.

Table 388:
This table covers 118 compounds of structural type T-3, wherein Y is $S(O)_2$, $R^1$ is ethyl, $R^2$ and $R^3$ are methyl, $R^4$ is hydrogen, G is hydrogen and $R^7$ and $R^8$ are as defined in Table 289.

Table 389:
This table covers 118 compounds of structural type T-3, wherein Y is $S(O)_2$, $R^1$ is ethyl, $R^2$ is hydrogen, $R^3$ and $R^4$ are methyl, G is hydrogen and $R^7$ and $R^8$ are as defined in Table 289.

Table 390:
This table covers 118 compounds of structural type T-3, wherein Y is $S(O)_2$, $R^1$ is ethyl, $R^2$, $R^3$ and $R^4$ are methyl, G is hydrogen and $R^7$ and $R^8$ are as defined in Table 289.

Table 391:
This table covers 118 compounds of structural type T-3, wherein Y is $S(O)_2$, $R^1$ and $R^2$ are ethyl, $R^3$ and $R^4$ are methyl, G is hydrogen and $R^7$ and $R^8$ are as defined in Table 289.

Table 392:
This table covers 118 compounds of structural type T-3, wherein Y is $S(O)_2$, $R^1$ and $R^3$ are ethyl, $R^2$ and $R^4$ are methyl, G is hydrogen and $R^7$ and $R^8$ are as defined in Table 289.

Table 393:
This table covers 118 compounds of structural type T-3, wherein Y is $S(O)_2$, $R^1$ and $R^2$ are ethyl, $R^3$ and $R^4$ are hydrogen, G is hydrogen and $R^7$ and $R^8$ are as defined in Table 289.

Table 394:
This table covers 118 compounds of structural type T-3, wherein Y is $S(O)_2$, $R^1$ and $R^3$ are ethyl, $R^2$ and $R^4$ are hydrogen, G is hydrogen and $R^7$ and $R^8$ are as defined in Table 289.

Table 395:
This table covers 118 compounds of structural type T-3, wherein Y is $S(O)_2$, $R^1$ and $R^3$ are ethyl, $R^2$ is methyl, $R^4$ is hydrogen, G is hydrogen and $R^7$ and $R^8$ are as defined in Table 289.

Table 396:
This table covers 118 compounds of structural type T-3, wherein Y is $S(O)_2$, $R^1$ and $R^3$ are ethyl, $R^2$ and $R^4$ are methyl, G is hydrogen and $R^7$ and $R^8$ are as defined in Table 289.

Table 397:
This table covers 118 compounds of structural type T-3, wherein Y is $S(O)_2$, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 398:
This table covers 118 compounds of structural type T-3, wherein Y is $S(O)_2$, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 399:
This table covers 118 compounds of structural type T-3, wherein Y is $S(O)_2$, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 400:
This table covers 118 compounds of structural type T-3, wherein Y is $S(O)_2$, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 401:
This table covers 118 compounds of structural type T-3, wherein Y is $S(O)_2$, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 402:
This table covers 118 compounds of structural type T-3, wherein Y is $S(O)_2$, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 403:
This table covers 118 compounds of structural type T-3, wherein Y is $S(O)_2$, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 404:
This table covers 118 compounds of structural type T-3, wherein Y is $S(O)_2$, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 405:
This table covers 118 compounds of structural type T-3, wherein Y is $S(O)_2$, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 406:
This table covers 118 compounds of structural type T-3, wherein Y is $S(O)_2$, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 407:
This table covers 118 compounds of structural type T-3, wherein Y is $S(O)_2$, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 408:
This table covers 118 compounds of structural type T-3, wherein Y is $S(O)_2$, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 409:
This table covers 118 compounds of structural type T-3, wherein Y is C=O, $R^1$ and $R^2$ are methyl, $R^3$ and $R^4$ are hydrogen, G is hydrogen and $R^7$ and $R^8$ are as defined in Table 289.

Table 410:
This table covers 118 compounds of structural type T-3, wherein Y is C=O, $R^1$, $R^2$, and $R^3$ are methyl, $R^4$ is hydrogen, G is hydrogen and $R^7$ and $R^8$ are as defined in Table 289.

Table 411:
This table covers 118 compounds of structural type T-3, wherein Y is C=O, $R^1$, $R^2$, $R^3$ and $R^4$ are methyl, G is hydrogen and $R^7$ and $R^8$ are as defined in Table 289.

Table 412:
This table covers 118 compounds of structural type T-3, wherein Y is C=O, $R^1$ is ethyl, $R^2$ is methyl, $R^3$ and $R^4$ are hydrogen, G is hydrogen and $R^7$ and $R^8$ are as defined in Table 289.

Table 413:
This table covers 118 compounds of structural type T-3, wherein Y is C=O, $R^1$ is ethyl, $R^2$ and $R^3$ are methyl, $R^4$ is hydrogen, G is hydrogen and $R^7$ and $R^8$ are as defined in Table 289.

Table 414:
This table covers 118 compounds of structural type T-3, wherein Y is C=O, $R^1$ is ethyl, $R^2$ is hydrogen, $R^3$ and $R^4$ are methyl, G is hydrogen and $R^7$ and $R^8$ are as defined in Table 289.

Table 415:
This table covers 118 compounds of structural type T-3, wherein Y is C=O, $R^1$ is ethyl, $R^2$, $R^3$ and $R^4$ are methyl, G is hydrogen and $R^7$ and $R^8$ are as defined in Table 289.

Table 416:
This table covers 118 compounds of structural type T-3, wherein Y is C=O, $R^1$ and $R^2$ are ethyl, $R^3$ and $R^4$ are methyl, G is hydrogen and $R^7$ and $R^8$ are as defined in Table 289.

Table 417:
This table covers 118 compounds of structural type T-3, wherein Y is C=O, $R^1$ and $R^3$ are ethyl, $R^2$ and $R^4$ are methyl, G is hydrogen and $R^7$ and $R^8$ are as defined in Table 289.

Table 418:
This table covers 118 compounds of structural type T-3, wherein Y is C=O, $R^1$ and $R^2$ are ethyl, $R^3$ and $R^4$ are hydrogen, G is hydrogen and $R^7$ and $R^8$ are as defined in Table 289.

Table 419:
This table covers 118 compounds of structural type T-3, wherein Y is C=O, $R^1$ and $R^3$ are ethyl, $R^2$ is methyl, $R^4$ is hydrogen, G is hydrogen and $R^7$ and $R^8$ are as defined in Table 289.

Table 420:
This table covers 118 compounds of structural type T-3, wherein Y is C=O, $R^1$ and $R^3$ are ethyl, $R^2$ and $R^4$ are methyl, G is hydrogen and $R^7$ and $R^8$ are as defined in Table 289.

Table 421:
This table covers 118 compounds of structural type T-3, wherein Y is C=O, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 422:
This table covers 118 compounds of structural type T-3, wherein Y is C=O, Fe and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 423:
This table covers 118 compounds of structural type T-3, wherein Y is C=O, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 424:
This table covers 118 compounds of structural type T-3, wherein Y is C=O, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 425:
This table covers 118 compounds of structural type T-3, wherein Y is C=O, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 426:
This table covers 118 compounds of structural type T-3, wherein Y is C=O, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 427:
This table covers 118 compounds of structural type T-3, wherein Y is C=O, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 428:
This table covers 118 compounds of structural type T-3, wherein Y is C=O, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 429:
This table covers 118 compounds of structural type T-3, wherein Y is C=O, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 430:
This table covers 118 compounds of structural type T-3, wherein Y is C=O, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 431:
This table covers 118 compounds of structural type T-3, wherein Y is C=O, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 432:

This table covers 118 compounds of structural type T-3, wherein Y is C=O, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 433:

This table covers 118 compounds of structural type T-4:

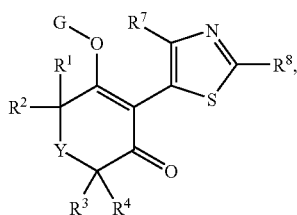

T-4 wherein Y is O, $R^1$, $R^2$, $R^3$ and $R^4$ are hydrogen, G is hydrogen and $R^7$ and $R^8$ are as defined in Table 289.

Table 434:

This table covers 118 compounds of structural type T-4, wherein Y is O, $R^1$ is methyl $R^2$, $R^3$ and $R^4$ are hydrogen, G is hydrogen and $R^7$ and $R^8$ are as defined in Table 289.

Table 435:

This table covers 118 compounds of structural type T-4, wherein Y is O, $R^1$ and $R^2$ are methyl, $R^3$ and $R^4$ are hydrogen, G is hydrogen and $R^7$ and $R^8$ are as defined in Table 289.

Table 436:

This table covers 118 compounds of structural type T-4, wherein Y is O, $R^1$ and $R^3$ are methyl, $R^2$ and $R^4$ are hydrogen, G is hydrogen and $R^7$ and $R^8$ are as defined in Table 289.

Table 437

This table covers 118 compounds of structural type T-4, wherein Y is O, $R^1$, $R^2$, and $R^3$ are methyl, $R^4$ is hydrogen, G is hydrogen and $R^7$ and $R^8$ are as defined in Table 289.

Table 438:

This table covers 118 compounds of structural type T-4, wherein Y is O, $R^1$, $R^2$, $R^3$ and $R^4$ are methyl, G is hydrogen and $R^7$ and $R^8$ are as defined in Table 289.

Table 439:

This table covers 118 compounds of structural type T-4, wherein Y is O, $R^1$ is ethyl, $R^2$, $R^3$ and $R^4$ are hydrogen, G is hydrogen and $R^7$ and $R^8$ are as defined in Table 88:

Table 440:

This table covers 118 compounds of structural type T-4, wherein Y is O, $R^1$ is ethyl, $R^2$ is methyl, $R^3$ and $R^4$ are hydrogen, G is hydrogen and $R^7$ and $R^8$ are as defined in Table 289.

Table 441:

This table covers 118 compounds of structural type T-4, wherein Y is O, $R^1$ is ethyl, $R^2$ and $R^3$ are hydrogen, $R^4$ is methyl, G is hydrogen and $R^7$ and $R^8$ are as defined in Table 289.

Table 442:

This table covers 118 compounds of structural type T-4, wherein Y is O, $R^1$ is ethyl, $R^2$ and $R^3$ are methyl, $R^4$ is hydrogen, G is hydrogen and $R^7$ and $R^8$ are as defined in Table 289.

Table 443:

This table covers 118 compounds of structural type T-4, wherein Y is O, $R^1$ is ethyl, $R^2$ is hydrogen, $R^3$ and $R^4$ are methyl, G is hydrogen and $R^7$ and $R^8$ are as defined in Table 289.

Table 444:

This table covers 118 compounds of structural type T-4, wherein Y is O, $R^1$ is ethyl, $R^2$, $R^3$ and $R^4$ are methyl, G is hydrogen and $R^7$ and $R^8$ are as defined in Table 289.

Table 445:

This table covers 118 compounds of structural type T-4, wherein Y is O, $R^1$ and $R^2$ are ethyl, $R^3$ and $R^4$ are methyl, G is hydrogen and $R^7$ and $R^8$ are as defined in Table 289.

Table 446:

This table covers 118 compounds of structural type T-4, wherein Y is O, $R^1$ and $R^3$ are ethyl, $R^2$ and $R^4$ are methyl, G is hydrogen and $R^7$ and $R^8$ are as defined in Table 289.

Table 447:

This table covers 118 compounds of structural type T-4, wherein Y is O, $R^1$ and $R^2$ are ethyl, $R^3$ and $R^4$ are hydrogen, G is hydrogen and $R^7$ and $R^8$ are as defined in Table 289.

Table 448:

This table covers 118 compounds of structural type T-4, wherein Y is O, $R^1$ and $R^3$ are ethyl, $R^2$ and $R^4$ are hydrogen, G is hydrogen and $R^7$ and $R^8$ are as defined in Table 289.

Table 449:

This table covers 118 compounds of structural type T-4, wherein Y is O, $R^1$ and $R^3$ are ethyl, $R^2$ is methyl, $R^4$ is hydrogen, G is hydrogen and $R^7$ and $R^8$ are as defined in Table 289.

Table 450:

This table covers 118 compounds of structural type T-4, wherein Y is O, $R^1$ and $R^3$ are ethyl, $R^2$ and $R^4$ are methyl, G is hydrogen and $R^7$ and $R^8$ are as defined in Table 289.

Table 451:

This table covers 118 compounds of structural type T-4, wherein Y is O, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 452:

This table covers 118 compounds of structural type T-4, wherein Y is O, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 453:

This table covers 118 compounds of structural type T-4, wherein Y is O, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 454:

This table covers 118 compounds of structural type T-4, wherein Y is O, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 455:

This table covers 118 compounds of structural type T-4, wherein Y is O, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 456:
This table covers 118 compounds of structural type T-4, wherein Y is O, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 457:
This table covers 118 compounds of structural type T-4, wherein Y is O, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 458:
This table covers 118 compounds of structural type T-4, wherein Y is O, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 459:
This table covers 118 compounds of structural type T-4, wherein Y is O, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 460:
This table covers 118 compounds of structural type T-4, wherein Y is O, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 461:
This table covers 118 compounds of structural type T-4, wherein Y is O, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 462:
This table covers 118 compounds of structural type T-4, wherein Y is O, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 463:
This table covers 118 compounds of structural type T-4, wherein Y is S, $R^1$, $R^2$, $R^3$ and $R^4$ are hydrogen, G is hydrogen and $R^7$ and $R^8$ are as defined in Table 289.

Table 464:
This table covers 118 compounds of structural type T-4, wherein Y is S, $R^1$ is methyl $R^2$, $R^3$ and $R^4$ are hydrogen, G is hydrogen and $R^7$ and $R^8$ are as defined in Table 289.

Table 465:
This table covers 118 compounds of structural type T-4, wherein Y is S, $R^1$ and $R^2$ are methyl, $R^3$ and $R^4$ are hydrogen, G is hydrogen and $R^7$ and $R^8$ are as defined in Table 289.

Table 466:
This table covers 118 compounds of structural type T-4, wherein Y is S, $R^1$ and $R^3$ are methyl, $R^2$ and $R^4$ are hydrogen, G is hydrogen and $R^7$ and $R^8$ are as defined in Table 289.

Table 467:
This table covers 118 compounds of structural type T-4, wherein Y is S, $R^1$, $R^2$, and $R^3$ are methyl, $R^4$ is hydrogen, G is hydrogen and $R^7$ and $R^8$ are as defined in Table 289.

Table 468:
This table covers 118 compounds of structural type T-4, wherein Y is S, $R^1$, $R^2$, $R^3$ and $R^4$ are methyl, G is hydrogen and $R^7$ and $R^8$ are as defined in Table 289.

Table 469:
This table covers 118 compounds of structural type T-4, wherein Y is S, $R^1$ is ethyl, $R^2$, $R^3$ and $R^4$ are hydrogen, G is hydrogen and $R^7$ and $R^8$ are as defined in Table 289.

Table 470:
This table covers 118 compounds of structural type T-4, wherein Y is S, $R^1$ is ethyl, $R^2$ is methyl, $R^3$ and $R^4$ are hydrogen, G is hydrogen and $R^7$ and $R^8$ are as defined in Table 289.

Table 471:
This table covers 118 compounds of structural type T-4, wherein Y is S, $R^1$ is ethyl, $R^2$ and $R^3$ are hydrogen, $R^4$ is methyl, G is hydrogen and $R^7$ and $R^8$ are as defined in Table 289.

Table 472:
This table covers 118 compounds of structural type T-4, wherein Y is S, $R^1$ is ethyl, $R^2$ and $R^3$ are methyl, $R^4$ is hydrogen, G is hydrogen and $R^7$ and $R^8$ are as defined in Table 289.

Table 473:
This table covers 118 compounds of structural type T-4, wherein Y is S, $R^1$ is ethyl, $R^2$ is hydrogen, $R^3$ and $R^4$ are methyl, G is hydrogen and $R^7$ and $R^8$ are as defined in Table 289.

Table 474:
This table covers 118 compounds of structural type T-4, wherein Y is S, $R^1$ is ethyl, $R^2$, $R^3$ and $R^4$ are methyl, G is hydrogen and $R^7$ and $R^8$ are as defined in Table 289.

Table 475:
This table covers 118 compounds of structural type T-4, wherein Y is S, $R^1$ and $R^2$ are ethyl, $R^3$ and $R^4$ are methyl, G is hydrogen and $R^7$ and $R^8$ are as defined in Table 289.

Table 476:
This table covers 118 compounds of structural type T-4, wherein Y is S, $R^1$ and $R^3$ are ethyl, $R^2$ and $R^4$ are methyl, G is hydrogen and $R^7$ and $R^8$ are as defined in Table 289.

Table 477:
This table covers 118 compounds of structural type T-4, wherein Y is S, $R^1$ and $R^2$ are ethyl, $R^3$ and $R^4$ are hydrogen, G is hydrogen and $R^7$ and $R^8$ are as defined in Table 289.

Table 478:
This table covers 118 compounds of structural type T-4, wherein Y is S, $R^1$ and $R^3$ are ethyl, $R^2$ and $R^4$ are hydrogen, G is hydrogen and $R^7$ and $R^8$ are as defined in Table 289.

Table 479:
This table covers 118 compounds of structural type T-4, wherein Y is S, $R^1$ and $R^3$ are ethyl, $R^2$ is methyl, $R^4$ is hydrogen, G is hydrogen and $R^7$ and $R^8$ are as defined in Table 289.

Table 480:
This table covers 118 compounds of structural type T-4, wherein Y is S, $R^1$ and $R^3$ are ethyl, $R^2$ and $R^4$ are methyl, G is hydrogen and $R^7$ and $R^8$ are as defined in Table 289.

Table 481:
This table covers 118 compounds of structural type T-4, wherein Y is S, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 482:
This table covers 118 compounds of structural type T-4, wherein Y is S, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 483:
This table covers 118 compounds of structural type T-4, wherein Y is S, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 484:
This table covers 118 compounds of structural type T-4, wherein Y is S, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 485:
This table covers 118 compounds of structural type T-4, wherein Y is S, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 486:
This table covers 118 compounds of structural type T-4, wherein Y is S, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 487:
This table covers 118 compounds of structural type T-4, wherein Y is S, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 488:
This table covers 118 compounds of structural type T-4, wherein Y is S, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 489:
This table covers 118 compounds of structural type T-4, wherein Y is S, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 490:
This table covers 118 compounds of structural type T-4, wherein Y is S, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 491:
This table covers 118 compounds of structural type T-4, wherein Y is S, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 492:
This table covers 118 compounds of structural type T-4, wherein Y is S, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 493:
This table covers 118 compounds of structural type T-4, wherein Y is S(O), $R^1$, $R^2$, $R^3$ and $R^4$ are hydrogen, G is hydrogen and $R^7$ and $R^8$ are as defined in Table 289.

Table 494:
This table covers 118 compounds of structural type T-4, wherein Y is S(O), $R^1$ is methyl $R^2$, $R^3$ and $R^4$ are hydrogen, G is hydrogen and $R^7$ and $R^8$ are as defined in Table 289.

Table 495:
This table covers 118 compounds of structural type T-4, wherein Y is S(O), $R^1$ and $R^2$ are methyl, $R^3$ and $R^4$ are hydrogen, G is hydrogen and $R^7$ and $R^8$ are as defined in Table 289.

Table 496:
This table covers 118 compounds of structural type T-4, wherein Y is S(O), Fe and $R^3$ are methyl, $R^2$ and $R^4$ are hydrogen, G is hydrogen and $R^7$ and $R^8$ are as defined in Table 289.

Table 497:
This table covers 118 compounds of structural type T-4, wherein Y is S(O), $R^1$, $R^2$, and $R^3$ are methyl, $R^4$ is hydrogen, G is hydrogen and $R^7$ and $R^8$ are as defined in Table 289.

Table 498:
This table covers 118 compounds of structural type T-4, wherein Y is S(O), $R^1$, $R^2$, $R^3$ and $R^4$ are methyl, G is hydrogen and $R^7$ and $R^8$ are as defined in Table 289.

Table 499:
This table covers 118 compounds of structural type T-4, wherein Y is S(O), $R^1$ is ethyl, $R^2$, $R^3$ and $R^4$ are hydrogen, G is hydrogen and $R^7$ and $R^8$ are as defined in Table 289.

Table 500:
This table covers 118 compounds of structural type T-4, wherein Y is S(O), $R^1$ is ethyl, $R^2$ is methyl, $R^3$ and $R^4$ are hydrogen, G is hydrogen and $R^7$ and $R^8$ are as defined in Table 289.

Table 501:
This table covers 118 compounds of structural type T-4, wherein Y is S(O), $R^1$ is ethyl, $R^2$ and $R^3$ are hydrogen, $R^4$ is methyl, G is hydrogen and $R^7$ and $R^8$ are as defined in Table 289.

Table 502:
This table covers 118 compounds of structural type T-4, wherein Y is S(O), $R^1$ is ethyl, $R^2$ and $R^3$ are methyl, $R^4$ is hydrogen, G is hydrogen and $R^7$ and $R^8$ are as defined in Table 289.

Table 503:
This table covers 118 compounds of structural type T-4, wherein Y is S(O), $R^1$ is ethyl, $R^2$ is hydrogen, $R^3$ and $R^4$ are methyl, G is hydrogen and $R^7$ and $R^8$ are as defined in Table 289.

Table 504:
This table covers 118 compounds of structural type T-4, wherein Y is S(O), $R^1$ is ethyl, $R^2$, $R^3$ and $R^4$ are methyl, G is hydrogen and $R^7$ and $R^8$ are as defined in Table 289.

Table 505:
This table covers 118 compounds of structural type T-4, wherein Y is S(O), $R^1$ and $R^2$ are ethyl, $R^3$ and $R^4$ are methyl, G is hydrogen and $R^7$ and $R^8$ are as defined in Table 289.

Table 506:
This table covers 118 compounds of structural type T-4, wherein Y is S(O), $R^1$ and $R^3$ are ethyl, $R^2$ and $R^4$ are methyl, G is hydrogen and $R^7$ and $R^8$ are as defined in Table 289.

Table 507:
This table covers 118 compounds of structural type T-4, wherein Y is S(O), $R^1$ and $R^2$ are ethyl, $R^3$ and $R^4$ are hydrogen, G is hydrogen and $R^7$ and $R^8$ are as defined in Table 289.

Table 508:
This table covers 118 compounds of structural type T-4, wherein Y is S(O), $R^1$ and $R^3$ are ethyl, $R^2$ and $R^4$ are hydrogen, G is hydrogen and $R^7$ and $R^8$ are as defined in Table 289.

Table 509:
This table covers 118 compounds of structural type T-4, wherein Y is S(O), $R^1$ and $R^3$ are ethyl, $R^2$ is methyl, $R^4$ is hydrogen, G is hydrogen and $R^7$ and $R^8$ are as defined in Table 289.

Table 510:
This table covers 118 compounds of structural type T-4, wherein Y is S(O), $R^1$ and $R^3$ are ethyl, $R^2$ and $R^4$ are methyl, G is hydrogen and $R^7$ and $R^8$ are as defined in Table 289.

Table 511:
This table covers 118 compounds of structural type T-4, wherein Y is S(O), $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 512:
This table covers 118 compounds of structural type T-4, wherein Y is S(O), $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 513:
This table covers 118 compounds of structural type T-4, wherein Y is S(O), $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 514:
This table covers 118 compounds of structural type T-4, wherein Y is S(O), $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 515:
This table covers 118 compounds of structural type T-4, wherein Y is S(O), $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 516:
This table covers 118 compounds of structural type T-4, wherein Y is S(O), $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 517:
This table covers 118 compounds of structural type T-4, wherein Y is S(O), $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 518:
This table covers 118 compounds of structural type T-4, wherein Y is S(O), $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 519:
This table covers 118 compounds of structural type T-4, wherein Y is S(O), $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 520:
This table covers 118 compounds of structural type T-4, wherein Y is S(O), $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 521:
This table covers 118 compounds of structural type T-4, wherein Y is S(O), $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 522:
This table covers 118 compounds of structural type T-4, wherein Y is S(O), Fe and $R^2$, together with the carbon to which they are attached, are joined to form a cyclohexane ring, $R^3$ and $R^4$ are methyl, G is hydrogen and $R^7$ and $R^8$ are as defined in Table 289.

Table 523:
This table covers 118 compounds of structural type T-4, wherein Y is $S(O)_2$, $R^1$, $R^2$, $R^3$ and $R^4$ are hydrogen, G is hydrogen and $R^7$ and $R^8$ are as defined in Table 289.

Table 524:
This table covers 118 compounds of structural type T-4, wherein Y is $S(O)_2$, $R^1$ is methyl $R^2$, $R^3$ and $R^4$ are hydrogen, G is hydrogen and $R^7$ and $R^8$ are as defined in Table 289.

Table 525:
This table covers 118 compounds of structural type T-4, wherein Y is $S(O)_2$, $R^1$ and $R^2$ are methyl, $R^3$ and $R^4$ are hydrogen, G is hydrogen and $R^7$ and $R^8$ are as defined in Table 289.

Table 526:
This table covers 118 compounds of structural type T-4, wherein Y is $S(O)_2$, $R^1$ and $R^3$ are methyl, $R^2$ and $R^4$ are hydrogen, G is hydrogen and $R^7$ and $R^8$ are as defined in Table 289.

Table 527:
This table covers 118 compounds of structural type T-4, wherein Y is $S(O)_2$, $R^1$, $R^2$, and $R^3$ are methyl, $R^4$ is hydrogen, G is hydrogen and $R^7$ and $R^8$ are as defined in Table 289.

Table 528:
This table covers 118 compounds of structural type T-4, wherein Y is $S(O)_2$, $R^1$, $R^2$, $R^3$ and $R^4$ are methyl, G is hydrogen and $R^7$ and $R^8$ are as defined in Table 289.

Table 529:
This table covers 118 compounds of structural type T-4, wherein Y is $S(O)_2$, $R^1$ is ethyl, $R^2$, $R^3$ and $R^4$ are hydrogen, G is hydrogen and $R^7$ and $R^8$ are as defined in Table 289.

Table 530:
This table covers 118 compounds of structural type T-4, wherein Y is $S(O)_2$, $R^1$ is ethyl, $R^2$ is methyl, $R^3$ and $R^4$ are hydrogen, G is hydrogen and $R^7$ and $R^8$ are as defined in Table 289.

Table 531:
This table covers 118 compounds of structural type T-4, wherein Y is $S(O)_2$, $R^1$ is ethyl, $R^2$ and R3 are hydrogen, $R^4$ is methyl, G is hydrogen and $R^7$ and $R^8$ are as defined in Table 289.

Table 532:
This table covers 118 compounds of structural type T-4, wherein Y is $S(O)_2$, $R^1$ is ethyl, $R^2$ and $R^3$ are methyl, $R^4$ is hydrogen, G is hydrogen and $R^7$ and $R^8$ are as defined in Table 289.

Table 533:
This table covers 118 compounds of structural type T-4, wherein Y is $S(O)_2$, $R^1$ is ethyl, $R^2$ is hydrogen, $R^3$ and $R^4$ are methyl, G is hydrogen and $R^7$ and $R^8$ are as defined in Table 289.

Table 534:
This table covers 118 compounds of structural type T-4, wherein Y is $S(O)_2$, $R^1$ is ethyl, $R^2$, $R^3$ and $R^4$ are methyl, G is hydrogen and $R^7$ and $R^8$ are as defined in Table 289.

Table 535:
This table covers 118 compounds of structural type T-4, wherein Y is $S(O)_2$, $R^1$ and $R^2$ are ethyl, $R^3$ and $R^4$ are methyl, G is hydrogen and $R^7$ and $R^8$ are as defined in Table 289.

Table 536:
This table covers 118 compounds of structural type T-4, wherein Y is $S(O)_2$, $R^1$ and $R^3$ are ethyl, $R^2$ and $R^4$ are methyl, G is hydrogen and $R^7$ and $R^8$ are as defined in Table 289.

Table 537:
This table covers 118 compounds of structural type T-4, wherein Y is $S(O)_2$, $R^1$ and $R^2$ are ethyl, $R^3$ and $R^4$ are hydrogen, G is hydrogen and $R^7$ and $R^8$ are as defined in Table 289.

Table 538:
This table covers 118 compounds of structural type T-4, wherein Y is $S(O)_2$, $R^1$ and $R^3$ are ethyl, $R^2$ and $R^4$ are hydrogen, G is hydrogen and $R^7$ and $R^8$ are as defined in Table 289.

Table 539:
This table covers 118 compounds of structural type T-4, wherein Y is $S(O)_2$, $R^1$ and $R^3$ are ethyl, $R^2$ is methyl, $R^4$ is hydrogen, G is hydrogen and $R^7$ and $R^8$ are as defined in Table 289.

Table 540:
This table covers 118 compounds of structural type T-4, wherein Y is $S(O)_2$, $R^1$ and $R^3$ are ethyl, $R^2$ and $R^4$ are methyl, G is hydrogen and $R^7$ and $R^8$ are as defined in Table 289.

Table 541:
This table covers 118 compounds of structural type T-4, wherein Y is $S(O)_2$, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 542:
This table covers 118 compounds of structural type T-4, wherein Y is $S(O)_2$, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 543:
This table covers 118 compounds of structural type T-4, wherein Y is $S(O)_2$, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 544:
This table covers 118 compounds of structural type T-4, wherein Y is $S(O)_2$, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 545:
This table covers 118 compounds of structural type T-4, wherein Y is $S(O)_2$, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 546:
This table covers 118 compounds of structural type T-4, wherein Y is $S(O)_2$, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 547:
This table covers 118 compounds of structural type T-4, wherein Y is $S(O)_2$, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 548:
This table covers 118 compounds of structural type T-4, wherein Y is $S(O)_2$, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 549:
This table covers 118 compounds of structural type T-4, wherein Y is $S(O)_2$, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 550:
This table covers 118 compounds of structural type T-4, wherein Y is $S(O)_2$, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 551:
This table covers 118 compounds of structural type T-4, wherein Y is $S(O)_2$, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 552:
This table covers 118 compounds of structural type T-4, wherein Y is $S(O)_2$, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 553:
This table covers 118 compounds of structural type T-4, wherein Y is C=O, $R^1$ and $R^2$ are methyl, $R^3$ and $R^4$ are hydrogen, G is hydrogen and $R^7$ and $R^8$ are as defined in Table 289.

Table 554:
This table covers 118 compounds of structural type T-4, wherein Y is C=O, $R^1$, $R^2$, and $R^3$ are methyl, $R^4$ is hydrogen, G is hydrogen and $R^7$ and $R^8$ are as defined in Table 289.

Table 555:
This table covers 118 compounds of structural type T-4, wherein Y is C=O, $R^1$, $R^2$, $R^3$ and $R^4$ are methyl, G is hydrogen and $R^7$ and $R^8$ are as defined in Table 289.

Table 556:
This table covers 118 compounds of structural type T-4, wherein Y is C=O, $R^1$ is ethyl, $R^2$ is methyl, $R^3$ and $R^4$ are hydrogen, G is hydrogen and $R^7$ and $R^8$ are as defined in Table 289.

Table 557:
This table covers 118 compounds of structural type T-4, wherein Y is C=O, $R^1$ is ethyl, $R^2$ and $R^3$ are methyl, $R^4$ is hydrogen, G is hydrogen and $R^7$ and $R^8$ are as defined in Table 289.

Table 558:
This table covers 118 compounds of structural type T-4, wherein Y is C=O, $R^1$ is ethyl, $R^2$ is hydrogen, $R^3$ and $R^4$ are methyl, G is hydrogen and $R^7$ and $R^8$ are as defined in Table 289.

Table 559:
This table covers 118 compounds of structural type T-4, wherein Y is C=O, $R^1$ is ethyl, $R^2$, $R^3$ and $R^4$ are methyl, G is hydrogen and $R^7$ and $R^8$ are as defined in Table 289.

Table 560:
This table covers 118 compounds of structural type T-4, wherein Y is C=O, $R^1$ and $R^2$ are ethyl, $R^3$ and $R^4$ are methyl, G is hydrogen and $R^7$ and $R^8$ are as defined in Table 289.

Table 561:
This table covers 118 compounds of structural type T-4, wherein Y is C=O, $R^1$ and $R^3$ are ethyl, $R^2$ and $R^4$ are methyl, G is hydrogen and $R^7$ and $R^8$ are as defined in Table 289.

Table 562:
This table covers 118 compounds of structural type T-4, wherein Y is C=O, $R^1$ and $R^2$ are ethyl, $R^3$ and $R^4$ are hydrogen, G is hydrogen and $R^7$ and $R^8$ are as defined in Table 289.

Table 563:
This table covers 118 compounds of structural type T-4, wherein Y is C=O, $R^1$ and $R^3$ are ethyl, $R^2$ is methyl, $R^4$ is hydrogen, G is hydrogen and $R^7$ and $R^8$ are as defined in Table 289.

Table 564:
This table covers 118 compounds of structural type T-4, wherein Y is C=O, $R^1$ and $R^3$ are ethyl, $R^2$ and $R^4$ are methyl, G is hydrogen and $R^7$ and $R^8$ are as defined in Table 289.

Table 565:
This table covers 118 compounds of structural type T-4, wherein Y is C=O, $R^1$ and $R^2$, together with the carbon to which they are attached, are joined to form a cyclopropane ring, $R^3$ and $R^4$ are hydrogen, G is hydrogen and $R^7$ and $R^8$ are as defined in Table 289.

Table 566:
This table covers 118 compounds of structural type T-4, wherein Y is C=O, $R^1$ and $R^2$, together with the carbon to which they are attached, are joined to form a cyclobutane ring, $R^3$ and $R^4$ are hydrogen, G is hydrogen and $R^7$ and $R^8$ are as defined in Table 289.

Table 567:
This table covers 118 compounds of structural type T-4, wherein Y is C=O, $R^1$ and $R^2$, together with the carbon to which they are attached, are joined to form a cyclopentane ring, $R^3$ and $R^4$ are hydrogen, G is hydrogen and $R^7$ and $R^8$ are as defined in Table 289.

Table 568:
This table covers 118 compounds of structural type T-4, wherein Y is C=O, $R^1$ and $R^2$, together with the carbon to which they are attached, are joined to form a cyclohexane ring, $R^3$ and $R^4$ are hydrogen, G is hydrogen and $R^7$ and $R^8$ are as defined in Table 289.

Table 569:
This table covers 118 compounds of structural type T-4, wherein Y is C=O, $R^1$ and $R^2$, together with the carbon to which they are attached, are joined to form a cyclopropane ring, $R^3$ is hydrogen, $R^4$ is methyl, G is hydrogen and $R^7$ and $R^8$ are as defined in Table 289.

Table 570:
This table covers 118 compounds of structural type T-4, wherein Y is C=O, $R^1$ and $R^2$, together with the carbon to which they are attached, are joined to form a cyclobutane ring, $R^3$ is hydrogen, $R^4$ is methyl, G is hydrogen and $R^7$ and $R^8$ are as defined in Table 289.

Table 571:
This table covers 118 compounds of structural type T-4, wherein Y is C=O, $R^1$ and $R^2$, together with the carbon to which they are attached, are joined to form a cyclopentane ring, $R^3$ is hydrogen, $R^4$ is methyl, G is hydrogen and $R^7$ and $R^8$ are as defined in Table 289.

Table 572:
This table covers 118 compounds of structural type T-4, wherein Y is C=O, $R^1$ and $R^2$, together with the carbon to which they are attached, are joined to form a cyclohexane ring, $R^3$ is hydrogen, $R^4$ is methyl, G is hydrogen and $R^7$ and $R^8$ are as defined in Table 289.

Table 573:
This table covers 118 compounds of structural type T-4, wherein Y is C=O, $R^1$ and $R^2$, together with the carbon to which they are attached, are joined to form a cyclopropane ring, $R^3$ and $R^4$ are methyl, G is hydrogen and $R^7$ and $R^8$ are as defined in Table 289.

Table 574:
This table covers 118 compounds of structural type T-4, wherein Y is C=O, $R^1$ and $R^2$, together with the carbon to which they are attached, are joined to form a cyclobutane ring, $R^3$ and $R^4$ are methyl, G is hydrogen and $R^7$ and $R^8$ are as defined in Table 289.

Table 575:
This table covers 118 compounds of structural type T-4, wherein Y is C=O, $R^1$ and $R^2$, together with the carbon to which they are attached, are joined to form a cyclopentane ring, $R^3$ and $R^4$ are methyl, G is hydrogen and $R^7$ and $R^8$ are as defined in Table 289.

Table 576:
This table covers 118 compounds of structural type T-4, wherein Y is C=O, $R^1$ and $R^2$, together with the carbon to which they are attached, are joined to form a cyclohexane ring, $R^3$ and $R^4$ are methyl, G is hydrogen and $R^7$ and $R^8$ are as defined in Table 289.

Table 577:
This table covers 122 compounds of the structural type T-5 wherein Y is O, $R^2$ and $R^4$ are hydrogen, G is hydrogen and $R^7$, $R^8$ and $R^{14}$ are as defined in Table 1:

Table 578:
This table covers 122 compounds of the structural type T-5, wherein Y is O, $R^2$ is hydrogen, $R^4$ is methyl, G is hydrogen and $R^7$, $R^8$ and $R^{14}$ are as defined in Table 1:

Table 579:
This table covers 122 compounds of the structural type T-5, wherein Y is O, $R^2$ and $R^4$ are methyl, G is hydrogen and $R^7$, $R^8$ and $R^{14}$ are as defined in Table 1.

Table 580:
This table covers 122 compounds of the structural type T-5, wherein Y is O, $R^2$ is hydrogen, $R^4$ is ethyl, G is hydrogen and $R^7$, $R^8$ and $R^{14}$ are as defined in Table 1:

Table 581:
This table covers 122 compounds of the structural type T-6

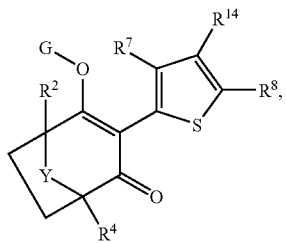

T-6 wherein Y is O, $R^2$ and $R^4$ are hydrogen, G is hydrogen and $R^7$, $R^8$ and $R^{14}$ are as defined in Table 1:

Table 582:
This table covers 122 compounds of the structural type T-6, wherein Y is O, $R^2$ is hydrogen, $R^4$ is methyl, G is hydrogen and $R^7$, $R^8$ and $R^{14}$ are as defined in Table 1:

Table 583:
This table covers 122 compounds of the structural type T-6, wherein Y is O, $R^2$ and $R^4$ are methyl, G is hydrogen and $R^7$, $R^8$ and $R^{14}$ are as defined in Table 1.

Table 584:
This table covers 122 compounds of the structural type T-6, wherein Y is O, $R^2$ is hydrogen, $R^4$ is ethyl, G is hydrogen and $R^7$, $R^8$ and $R^{14}$ are as defined in Table 1:

Table 585:
This table covers 118 compounds of structural type T-7:

T-7 wherein Y is O, $R^2$ and $R^4$ are hydrogen, G is hydrogen and $R^7$ and $R^8$ are as defined in Table 289.

Table 586:
This table covers 118 compounds of structural type T-7, wherein Y is O, $R^2$ is hydrogen, $R^4$ is methyl, G is hydrogen and $R^7$ and $R^8$ are as defined in Table 289.

Table 587:
This table covers 118 compounds of structural type T-7, wherein Y is O, $R^2$ and $R^4$ are methyl, G is hydrogen and $R^7$ and $R^8$ are as defined in Table 289.

Table 588:
This table covers 118 compounds of structural type T-7, wherein Y is O, $R^2$ is hydrogen, $R^4$ is ethyl, G is hydrogen and $R^7$ and $R^8$ are as defined in Table 289.

Table 589:
This table covers 118 compounds of structural type T-8:

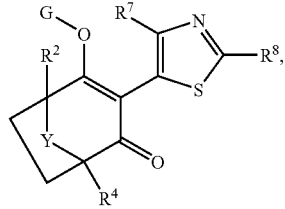

T-8 wherein Y is O, $R^2$ and $R^4$ are hydrogen, G is hydrogen and $R^7$ and $R^8$ are as defined in Table 289.

Table 590:
This table covers 118 compounds of structural type T-8, wherein Y is O, $R^2$ is hydrogen, $R^4$ is methyl, G is hydrogen and $R^7$ and $R^8$ are as defined in Table 289.

Table 591:
This table covers 118 compounds of structural type T-8, wherein Y is O, $R^2$ and $R^4$ are methyl, G is hydrogen and $R^7$ and $R^8$ are as defined in Table 289.

Table 592:
This table covers 118 compounds of structural type T-8, wherein Y is O, $R^2$ is hydrogen, $R^4$ is ethyl, G is hydrogen and $R^7$ and $R^8$ are as defined in Table 289.

BIOLOGICAL EXAMPLES

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 14 or 15 days later for post-emergence and 20 days for pre-emergence, the test was evaluated (100=total damage to plant; 0=no damage to plant).

Test Plants:
*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

| | | Pre-Emergence Activity | | | | | |
|---|---|---|---|---|---|---|---|
| Compound Number | Rate g/ha | ALOMY | AVEFA | LOLPE | SETFA | DIGSA | ECHCG |
| T6 | 250 | 50 | 20 | 80 | 60 | 70 | 50 |
| T11 | 250 | 100 | 100 | 100 | 100 | 100 | 100 |
| T12 | 250 | 30 | 0 | 0 | 0 | 20 | 40 |
| T13 | 250 | 100 | 50 | 100 | 100 | 100 | 100 |
| T16 | 250 | 90 | 50 | 100 | 0 | 100 | 60 |

Post-Emergence Activity

| Compound Number | Rate g/ha | ALOMY | AVEFA | LOLPE | SETFA | DIGSA | ECHCG |
|---|---|---|---|---|---|---|---|
| T6 | 125 | 70 | 60 | 30 | 70 | 70 | 70 |
| T11 | 125 | 90 | 80 | 60 | 100 | 100 | 100 |
| T12 | 125 | 80 | 70 | 70 | 80 | 90 | 100 |
| T13 | 125 | 90 | 80 | 70 | 100 | 100 | 100 |
| T16 | 125 | 70 | 70 | 60 | 90 | 90 | 100 |

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Alopecurus myosuroides* (ALOMY), *Avena fatua* (AVEFA), *Setaria faberi* (SETFA), *Echinochloa crus-galli* (ECHCG), *Solanum nigrum* (SOLNI) and *Amaranthus retoflexus* (AMARE)

Pre-Emergence Activity

| Compound Number | Rate g/ha | AVEFA | SOLNI | AMARE | SETFA | ALOMY | ECHCG |
|---|---|---|---|---|---|---|---|
| T2 | 1000 | 0 | 60 | 50 | 0 | 0 | 0 |
| T8 | 1000 | 20 | 0 | 0 | 0 | 30 | 0 |
| T10 | 1000 | 20 | 0 | 0 | 0 | 30 | 0 |
| T14 | 1000 | 0 | 0 | 0 | 0 | 40 | 0 |
| T20 | 1000 | 0 | 70 | 80 | 0 | 30 | 0 |
| P2 | 1000 | 30 | 0 | 80 | 80 | 60 | 50 |

| Compound Number | Rate g/ha | AMARE | SEFTA | ALOMY | ECHGG | AVEFA |
|---|---|---|---|---|---|---|
| T21 | 250 | 0 | 100 | 60 | 100 | 0 |
| T9 | 250 | 0 | 40 | 0 | 20 | 0 |
| T14 | 250 | 0 | 50 | 0 | 0 | 0 |
| T22 | 250 | 0 | 100 | 70 | 90 | 20 |
| T42 | 250 | 40 | 0 | 0 | 40 | 0 |
| T43 | 250 | 0 | 0 | 0 | 0 | 0 |
| T44 | 250 | 0 | 0 | 0 | 30 | 0 |
| T47 | 250 | 20 | 90 | 70 | 70 | 90 |
| T48 | 250 | 0 | 70 | 30 | 50 | 60 |
| T49 | 250 | 0 | 80 | 60 | 60 | 20 |
| T50 | 250 | 0 | 100 | 90 | 100 | 90 |
| T51 | 250 | 0 | 100 | 40 | 60 | 80 |
| T52 | 250 | 0 | 100 | 60 | 80 | 0 |
| T53 | 250 | 0 | 90 | 30 | 60 | 0 |
| T54 | 250 | 20 | 100 | 100 | 100 | 90 |
| T55 | 250 | 0 | 50 | 0 | 20 | 0 |
| T56 | 250 | 0 | 20 | 0 | 10 | 0 |
| T57 | 250 | 0 | 90 | 20 | 50 | 30 |
| T58 | 250 | 20 | 100 | 0 | 50 | 0 |
| T59 | 250 | 0 | 0 | 0 | 0 | 0 |
| T60 | 250 | 0 | 70 | 40 | 20 | 0 |
| T61 | 250 | 0 | 100 | 80 | 100 | 0 |
| T62 | 250 | 0 | 100 | 90 | 60 | 0 |
| T63 | 250 | 0 | 20 | 20 | 30 | 20 |
| T64 | 250 | 0 | 100 | 0 | 70 | 0 |
| T68 | 250 | 0 | 20 | 0 | 20 | 0 |
| T69 | 250 | 0 | 20 | 0 | 20 | 0 |
| T70 | 250 | 0 | 70 | 30 | 70 | 0 |
| T71 | 250 | 0 | 50 | 20 | 60 | 0 |
| P3 | 250 | 0 | 20 | 20 | 30 | 0 |
| P4 | 250 | 0 | 20 | 0 | 10 | 0 |
| P5 | 250 | 0 | 0 | 0 | 0 | 0 |
| P6 | 250 | 0 | 100 | 90 | 70 | 80 |
| P7 | 250 | 0 | 100 | 70 | 80 | 0 |
| P9 | 250 | 0 | 40 | 20 | 50 | 0 |

| Post-Emergence Activity | | | | | | | |
|---|---|---|---|---|---|---|---|
| Compound Number | Rate g/ha | AVEFA | SOLNI | AMARE | SETFA | ALOMY | ECHCG |
| T1 | 1000 | 80 | 0 | 0 | 90 | 90 | 90 |
| T2 | 1000 | 0 | 40 | 0 | 0 | 0 | 0 |
| T6 | 1000 | 90 | 0 | 0 | 100 | 90 | 90 |
| T8 | 1000 | 0 | 20 | 0 | 80 | 40 | 70 |
| T10 | 1000 | 0 | 20 | 0 | 80 | 40 | 70 |
| T15 | 1000 | 0 | 0 | 0 | 0 | 40 | 70 |
| T20 | 1000 | 0 | 0 | 0 | 10 | 0 | 0 |
| P2 | 1000 | 90 | 0 | 0 | 100 | 90 | 100 |

| Compound Number | Rate g/ha | AMARE | SEFTA | ALOMY | ECHGG | AVEFA |
|---|---|---|---|---|---|---|
| T5 | 250 | 0 | 50 | 40 | 70 | 0 |
| T9 | 250 | 0 | 80 | 90 | 90 | 40 |
| T14 | 250 | 0 | 90 | 40 | 70 | 0 |
| T21 | 250 | 0 | 100 | 100 | 100 | 90 |
| T22 | 250 | 0 | 100 | 100 | 100 | 90 |
| T25 | 250 | 0 | 20 | 0 | 20 | 0 |
| T27 | 250 | 30 | 50 | 20 | 30 | 0 |
| T42 | 250 | 0 | 0 | 0 | 20 | 0 |
| T43 | 250 | 0 | 0 | 0 | 30 | 0 |
| T45 | 250 | 0 | 70 | 30 | 70 | 0 |
| T47 | 250 | 0 | 100 | 100 | 100 | 100 |
| T48 | 250 | 0 | 100 | 100 | 100 | 100 |
| T49 | 250 | 20 | 100 | 100 | 100 | 100 |
| T50 | 250 | 0 | 100 | 100 | 100 | 100 |
| T51 | 250 | 0 | 100 | 100 | 90 | 90 |
| T52 | 250 | 0 | 100 | 100 | 100 | 100 |
| T53 | 250 | 0 | 100 | 90 | 100 | 90 |
| T54 | 250 | 0 | 100 | 100 | 100 | 100 |
| T55 | 250 | 0 | 60 | 40 | 70 | 0 |
| T56 | 250 | 0 | 90 | 30 | 80 | 20 |
| T57 | 250 | 0 | 100 | 100 | 100 | 90 |
| T58 | 250 | 0 | 100 | 90 | 100 | 80 |
| T59 | 250 | 0 | 30 | 30 | 70 | 0 |
| T60 | 250 | 0 | 90 | 50 | 90 | 40 |
| T61 | 250 | 0 | 90 | 90 | 100 | 70 |
| T62 | 250 | 0 | 100 | 100 | 100 | 100 |
| T63 | 250 | 0 | 100 | 80 | 100 | 90 |
| T64 | 250 | 0 | 100 | 20 | 100 | 60 |
| T65 | 250 | 0 | 100 | 90 | 100 | 70 |
| T66 | 250 | 0 | 80 | 70 | 90 | 40 |
| T67 | 250 | 0 | 70 | 0 | 90 | 0 |
| T68 | 250 | 0 | 70 | 0 | 80 | 0 |
| T69 | 250 | 0 | 90 | 60 | 100 | 40 |
| T70 | 250 | 0 | 90 | 70 | 90 | 10 |
| T71 | 250 | 0 | 90 | 20 | 90 | 40 |
| P3 | 250 | 0 | 90 | 50 | 90 | 30 |
| P4 | 250 | 0 | 90 | 40 | 90 | 0 |
| P5 | 250 | 0 | 0 | 0 | 0 | 0 |
| P6 | 250 | 0 | 100 | 100 | 100 | 90 |
| P7 | 250 | 0 | 100 | 80 | 100 | 80 |
| P9 | 250 | 30 | 80 | 90 | 100 | 80 |

What is claimed is:

1. A compound of formula I

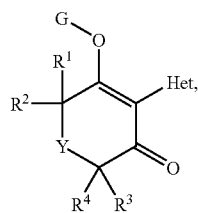

wherein $R^1$, $R^2$, $R^3$ and $R^4$, independently of each other, are hydrogen, $C_1$-$C_4$ alkyl, $C_1$-$C_4$ haloalkyl, $C_1$-$C_4$ alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$ haloalkyl or halogen; cyclobutyl or cyclobutyl substituted by $C_1$- or $C_2$ alkyl; oxetanyl or oxetanyl substituted by $C_1$- or $C_2$ alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutylC$_1$-C$_5$alkyl substituted by C$_1$-C$_2$ alkyl; oxetanylC$_1$-C$_5$alkyl or oxetanylC$_1$-C$_5$alkyl substituted by C$_1$- or C$_2$alkyl; C$_5$-C$_7$cycloalkylC$_1$-C$_5$alkyl or C$_5$-C$_7$cycloalkylC$_1$-C$_5$alkyl substituted by C$_1$- or C$_2$alkyl or C$_1$- or C$_2$haloalkyl, where a methylene group of the cycloalkyl moiety is optionally replaced by an oxygen or sulfur atom or a sulfinyl or sulfonyl group; C$_4$-C$_7$cycloalkenylC$_1$-C$_5$alkyl or C$_4$-C$_7$cycloalkenylC$_1$-C$_5$alkyl which is substituted by C$_1$- or C$_2$alkyl or C$_1$- or C$_2$haloalkyl, where a methylene group of the cycloalkenyl moiety is optionally replaced by an oxygen or sulfur atom or a sulfinyl or sulfonyl group; phenyl or phenyl substituted by C$_1$-C$_4$alkyl, C$_1$-C$_4$alkoxy, C$_1$-C$_4$haloalkyl, halogen, nitro, cyano, C$_1$-C$_4$ alkylthio, C$_1$-C$_4$alkylsulfinyl, C$_1$-C$_4$alkylsulfonyl or C$_1$-C$_4$alkylcarbonyl; benzyl or benzyl substituted by C$_1$-C$_4$alkyl, C$_1$-C$_4$ alkoxy, C$_1$-C$_4$haloalkyl, halogen, nitro, cyano, C$_1$-C$_4$ alkylthio, C$_1$-C$_4$alkylsulfinyl, C$_1$-C$_4$alkylsulfonyl or C$_1$-C$_4$alkylcarbonyl; heteroaryl or heteroaryl substituted by C$_1$-C$_4$alkyl, C$_1$-C$_4$alkoxy, C$_1$-C$_4$haloalkyl, halogen, nitro, cyano, C$_1$-C$_4$alkylthio, C$_1$-C$_4$alkylsulfinyl, C$_1$-C$_4$alkylsulfonyl or C$_1$-C$_4$alkylcarbonyl; or R$^1$ and R$^2$, or R$^3$ and R$^4$, are joined to form a 3-7 membered saturated ring in which a methylene group is optionally replaced by an oxygen or sulfur atom, and which may be optionally substituted by C$_1$- or C$_2$-alkyl, halogen or C$_1$-C$_2$ alkoxy, or a 5-7 membered unsaturated ring in which a methylene group is optionally replaced by an oxygen or sulfur atom, and which may be optionally substituted by C$_1$- or C$_2$-alkyl, halogen or C$_1$-C$_2$ alkoxy;

Y is O;

Het is a group of the formula R$_1$ to R$_{10}$:

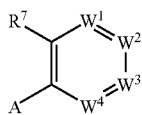
(R$_1$)

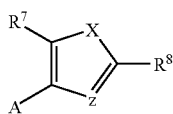
(R$_2$)

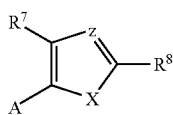
(R$_3$)

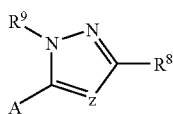
(R$_4$)

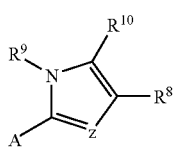
(R$_5$)

-continued

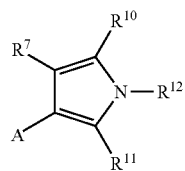
(R$_6$)

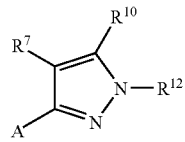
(R$_7$)

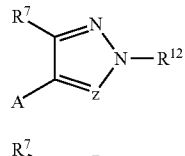
(R$_8$)

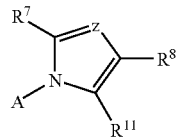
(R$_9$)

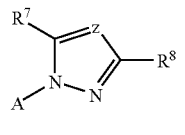
(R$_{10}$)

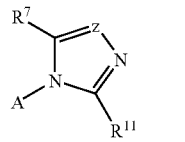
(R$_{11}$)

(R$_{12}$)

wherein A designates the point of attachment to the ketoenol moiety, and

W$^1$ is N or CR$^{10}$;
W$^2$ is N or CR$^8$;
W$^3$ is CR$^8$;
W$^4$ is N or CR$^{11}$;
with the proviso that at least one of W$^1$, W$^2$ or W$^4$ is N;
X is O, S, Se, or NR$^{13}$;
Z is N or CR$^{14}$;
R$^7$ is halogen, C$_1$-C$_4$ alkyl, C$_3$-C$_6$ cycloalkyl, C$_1$-C$_4$ haloalkyl, C$_2$-C$_4$ alkenyl, C$_2$-C$_4$ haloalkenyl, C$_2$-C$_4$ alkynyl, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, nitro or cyano;
R$^8$ is C$_1$-C$_4$ alkyl, C$_2$-C$_4$ alkenyl, C$_1$-C$_4$ alkoxy, C$_2$-C$_4$ alkenyloxy, C$_1$-C$_4$ alkylthio, C$_1$-C$_4$ alkylsulphinyl, C$_1$-C$_4$ alkylsulphonyl, C$_1$-C$_4$ alkoxy C$_1$-C$_4$ alkyl, or C$_1$-C$_4$ alkylthio C$_1$-C$_4$ alkyl, each of which is unsubstituted or substituted by halogen;
or R$^8$ is halogen, cyano, or nitro;
or R$^8$ is thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl, pyridazinyl, quinolinyl, isoquinolinyl, cinnolinyl, quinazolinyl or quinoxalinyl, or a salt thereof, each of these being unsubstituted or substituted by halogen, $C_1$-$C_4$ alkyl, halo$C_1$-$C_4$ alkyl, $C_1$-$C_4$ alkoxy, $C_2$-$C_4$ alkenyloxy, $C_1$-$C_4$ alkylthio, $C_1$-$C_4$ alkylsulphinyl, $C_1$-$C_4$ alkyl-sulphonyl, halo$C_1$-$C_4$ alkoxy, cyano or nitro;

$R^9$ is $C_1$-$C_4$ alkyl, $C_2$-$C_3$alkenyl, $C_2$-$C_3$alkynyl, $C_1$-$C_4$ haloalkyl or $C_2$-$C_3$ haloalkenyl;

$R^{10}$ is hydrogen, methyl, halomethyl or halogen;

$R^{11}$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano;

$R^{12}$ is methyl, ethyl, halomethyl, haloethyl, aryl, aryl substituted by $C_1$-$C_2$-alkyl, $C_1$-$C_2$-alkoxy, $C_1$-$C_2$ haloalkyl, $C_1$-$C_2$ haloalkoxy, cyano or nitro, heteroaryl or heteroaryl substituted by $C_1$-$C_2$-alkyl, $C_1$-$C_2$-alkoxy, $C_1$-$C_2$ haloalkyl, $C_1$-$C_2$ haloalkoxy, cyano or nitro;

$R^{13}$ is hydrogen, methyl or halomethyl; and $R^{14}$ is hydrogen, methyl, ethyl, halomethyl, haloethyl, halogen, cyano or nitro;

or Het is a group of the formula $R_{2A}$:

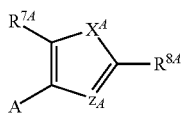

wherein A designates the point of attachment to the ketoenol moiety, and $X^A$ is sulfur;

$R^{7A}$ is methyl or ethyl;

$R^{8A}$ is phenyl, or phenyl substituted one to three times by halogen, $C_1$-$C_2$-alkyl, $C_1$-$C_2$-alkoxy, $C_1$-$C_2$ haloalkyl, $C_1$-$C_2$ haloalkoxy, cyano or nitro; and $Z_A$ is nitrogen or C—H;

and

G is hydrogen, an alkali metal, alkaline earth metal, sulfonium, ammonium or a latentiating group;

wherein, when G is a latentiating group, then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$alkenyl, $C_3$haloalkenyl, $C_3$alkenyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;

wherein $X^a$, $X^b$, $X^c$, $X^d$, $X^e$ and $X^f$ are independently of each other oxygen or sulfur;

and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, amino, $C_1$-$C_3$alkylamino, $C_1$-$C_3$dialkylamino, $C_1$-$C_3$alkoxy or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S and optionally substituted by 1 or 2 $C_1$-$C_3$alkyl groups; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, nitro, amino, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, amino, hydroxyl, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl,
$C_1$-$C_5$alkylcarbonyl$C_1$-$C_5$alkyl,
$C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl,
$C_2$-$C_8$dialkylaminocarbonyl$C_1$-$C_5$alkyl,
$C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl,
$C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;
and wherein, within $r^1$, $R^2$, $R^3$, $R^4$, and $R^{12}$, "heteroaryl" means thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl or pyridazinyl, or, where appropriate, a salt thereof.

2. A compound according to claim 1, wherein $R^1$, $R^2$, $R^3$ and $R^4$, independently of each other, are hydrogen or $C_1$-$C_4$ alkyl.

3. A compound according to claim 2, wherein $R^1$, $R^2$, $R^3$ and $R^4$, independently of each other, are hydrogen, methyl or ethyl.

4. A compound according to claim 3, wherein $R^1$, $R^2$, $R^3$ and $R^4$ are methyl.

5. A compound according to claim 1, wherein G is hydrogen, an alkali metal or an alkaline earth metal.

6. A compound according to claim 5, wherein G is hydrogen.

7. A compound according to claim 1, wherein Het is selected from the groups of the formulae $R_2$ to $R_{10}$ and $R_{2A}$, as defined in claim 1, and wherein Het is a substituted monocyclic 5-membered nitrogen or sulfur containing heteroaryl.

8. A compound according to claim 1, wherein Het is a group of the formula $R_2$, wherein
X is sulfur;
$R^8$ is thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl, pyridazinyl, quinolinyl, isoquinolinyl, cinnolinyl, quinazolinyl or quinoxalinyl, or a salt thereof, each of which is optionally substituted one to three times by halogen, $C_1$-$C_2$-alkyl, $C_1$-$C_2$-alkoxy, $C_1$-$C_2$ haloalkyl, $C_1$-$C_2$ haloalkoxy, cyano or nitro; and
Z is nitrogen or C—H.

9. A compound according to claim 1, wherein Het is a group of the formula $R_{2A}$, wherein
$X^A$ is sulfur;
$R^{7A}$ is methyl or ethyl;
$R^{8A}$ is phenyl, or phenyl substituted one to three times by halogen, $C_1$-$C_2$-alkyl, $C_1$-$C_2$-alkoxy, $C_1$-$C_2$ haloalkyl, $C_1$-$C_2$ haloalkoxy, cyano or nitro; and
$Z_A$ is nitrogen or C—H.

10. A method of controlling grasses and weeds in crops of useful plants, which comprises applying a herbicidally effective amount of a compound of formula I according to claim 1, or of a composition comprising such a compound, to the plants or to the locus thereof.

11. A herbicidal composition comprising a herbicidally effective amount of a compound of formula I as defined in claim 1, and formulation adjuvants.

12. A composition according to claim 11 comprising a further herbicide as mixing partner.

13. A composition according to claim 11 further comprising a safener.

14. A composition according to claim 11 comprising a further herbicide as mixing partner and a safener.

15. A compound according to claim 1, wherein G is $C(X^a)$—$R^a$ or $C(X^b)$—$X^c$—$R^b$, and the meanings of $X^a$, $R^a$, $X^b$, $X^c$ and $R^b$ are as defined in claim 1.

16. A compound of structural type T-1:

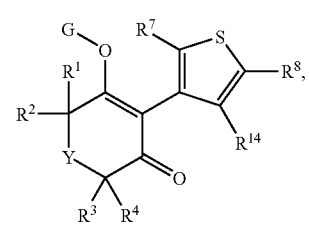

T-1 wherein:
Y is O;
G is hydrogen;
$R^7$ is $CH_3$ or $CH_3CH_2$;
$R^8$ is 4-methylthiophenyl, 4-methylsulfinylphenyl, 4-methylsulfonylphenyl, 4-trifluoromethylthiophenyl, 4-trifluoromethylsulfinylphenyl, or 4-trifluoromethylsulfonylphenyl; and
$R^{14}$ is H;
and wherein:
(1) $R^1$, $R^2$, $R^3$ and $R^4$ are hydrogen,
(2) $R^1$ is methyl, and $R^2$, $R^3$ and $R^4$ are hydrogen,
(3) $R^1$ and $R^2$ are methyl, and $R^3$ and $R^4$ are hydrogen,
(4) $R^1$ and $R^3$ are methyl, and $R^2$ and $R^4$ are hydrogen,
(5) $R^1$, $R^2$, and $R^3$ are methyl, and $R^4$ is hydrogen,
(6) $R^1$, $R^2$, $R^3$ and $R^4$ are methyl,
(7) $R^1$ is ethyl, and $R^2$, $R^3$ and $R^4$ are hydrogen,
(8) $R^1$ is ethyl, $R^2$ is methyl, and $R^3$ and $R^4$ are hydrogen,
(9) $R^1$ is ethyl, $R^2$ and $R^3$ are hydrogen, and $R^4$ is methyl,
(10) $R^1$ is ethyl, $R^2$ and $R^3$ are methyl, and $R^4$ is hydrogen,
(11) $R^1$ is ethyl, $R^2$ is hydrogen, and $R^3$ and $R^4$ are methyl,
(12) $R^1$ is ethyl, and $R^2$, $R^3$ and $R^4$ are methyl,
(13) $R^1$ and $R^2$ are ethyl, and $R^3$ and $R^4$ are methyl,
(14) $R^1$ and $R^3$ are ethyl, and $R^2$ and $R^4$ are methyl,
(15) $R^1$ and $R^2$ are ethyl, and $R^3$ and $R^4$ are hydrogen,
(16) $R^1$ and $R^3$ are ethyl, and $R^2$ and $R^4$ are hydrogen,
(17) $R^1$ and $R^3$ are ethyl, $R^2$ is methyl, and $R^4$ is hydrogen,
(18) $R^1$ and $R^3$ are ethyl, and $R^2$ and $R^4$ are methyl,

(19) $R^1$ and $R^2$, together with the carbon to which they are attached, are joined to form a cyclopropane ring, and $R^3$ and $R^4$ are hydrogen,
(20) $R^1$ and $R^2$, together with the carbon to which they are attached, are joined to form a cyclobutane ring, and $R^3$ and $R^4$ are hydrogen,
(21) $R^1$ and $R^2$, together with the carbon to which they are attached, are joined to form a cyclopentane ring, and $R^3$ and $R^4$ are hydrogen,
(22) $R^1$ and $R^2$, together with the carbon to which they are attached, are joined to form a cyclohexane ring, and $R^3$ and $R^4$ are hydrogen,
(23) $R^1$ and $R^2$, together with the carbon to which they are attached, are joined to form a cyclopropane ring, $R^3$ is hydrogen, and $R^4$ is methyl,
(24) $R^1$ and $R^2$, together with the carbon to which they are attached, are joined to form a cyclobutane ring, $R^3$ is hydrogen, and $R^4$ is methyl,
(25) $R^1$ and $R^2$, together with the carbon to which they are attached, are joined to form a cyclopentane ring, $R^3$ is hydrogen, and $R^4$ is methyl,
(26) $R^1$ and $R^2$, together with the carbon to which they are attached, are joined to form a cyclohexane ring, $R^3$ is hydrogen, and $R^4$ is methyl,
(27) $R^1$ and $R^2$, together with the carbon to which they are attached, are joined to form a cyclopropane ring, and $R^3$ and $R^4$ are methyl,
(28) $R^1$ and $R^2$, together with the carbon to which they are attached, are joined to form a cyclobutane ring, and $R^3$ and $R^4$ are methyl,
(29) $R^1$ and $R^2$, together with the carbon to which they are attached, are joined to form a cyclopentane ring, and $R^3$ and $R^4$ are methyl,
or
(30) $R^1$ and $R^2$, together with the carbon to which they are attached, are joined to form a cyclohexane ring, and $R^3$ and $R^4$ are methyl.

17. A compound of structural type T-3:

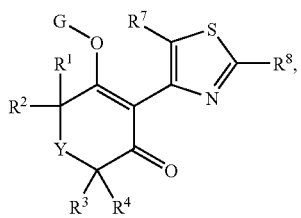

T-3 wherein:
Y is O;
G is hydrogen;
$R^7$ is $CH_3$ or $CH_3CH_2$; and
$R^8$ is 4-methylthiophenyl, 4-methylsulfinylphenyl, 4-methylsulfonylphenyl, 4-trifluoromethylthiophenyl, 4-trifluoromethylsulfinylphenyl, or 4-trifluoromethylsulfonylphenyl;
and wherein:
(1) $R^1$, $R^2$, $R^3$ and $R^4$ are hydrogen,
(2) $R^1$ is methyl, and $R^2$, $R^3$ and $R^4$ are hydrogen,
(3) $R^1$ and $R^2$ are methyl, and $R^3$ and $R^4$ are hydrogen,
(4) $R^1$ and $R^3$ are methyl, and $R^2$ and $R^4$ are hydrogen,
(5) $R^1$, $R^2$, and $R^3$ are methyl, and $R^4$ is hydrogen,
(6) $R^1$, $R^2$, $R^3$ and $R^4$ are methyl,
(7) $R^1$ is ethyl, and $R^2$, $R^3$ and $R^4$ are hydrogen,
(8) $R^1$ is ethyl, $R^2$ is methyl, and $R^3$ and $R^4$ are hydrogen,
(9) $R^1$ is ethyl, $R^2$ and $R^3$ are hydrogen, and $R^4$ is methyl,
(10) $R^1$ is ethyl, $R^2$ and $R^3$ are methyl, and $R^4$ is hydrogen,
(11) $R^1$ is ethyl, $R^2$ is hydrogen, and $R^3$ and $R^4$ are methyl,
(12) $R^1$ is ethyl, and $R^2$, $R^3$ and $R^4$ are methyl,
(13) $R^1$ and $R^2$ are ethyl, and $R^3$ and $R^4$ are methyl,
(14) $R^1$ and $R^3$ are ethyl, and $R^2$ and $R^4$ are methyl,
(15) $R^1$ and $R^2$ are ethyl, and $R^3$ and $R^4$ are hydrogen,
(16) $R^1$ and $R^3$ are ethyl, and $R^2$ and $R^4$ are hydrogen,
(17) $R^1$ and $R^3$ are ethyl, $R^2$ is methyl, and $R^4$ is hydrogen,
(18) $R^1$ and $R^3$ are ethyl, and $R^2$ and $R^4$ are methyl,
(19) $R^1$ and $R^2$, together with the carbon to which they are attached, are joined to form a cyclopropane ring, and $R^3$ and $R^4$ are hydrogen,
(20) $R^1$ and $R^2$, together with the carbon to which they are attached, are joined to form a cyclobutane ring, and $R^3$ and $R^4$ are hydrogen,
(21) $R^1$ and $R^2$, together with the carbon to which they are attached, are joined to form a cyclopentane ring, and $R^3$ and $R^4$ are hydrogen,
(22) $R^1$ and $R^2$, together with the carbon to which they are attached, are joined to form a cyclohexane ring, and $R^3$ and $R^4$ are hydrogen,
(23) $R^1$ and $R^2$, together with the carbon to which they are attached, are joined to form a cyclopropane ring, $R^3$ is hydrogen, and $R^4$ is methyl,
(24) $R^1$ and $R^2$, together with the carbon to which they are attached, are joined to form a cyclobutane ring, $R^3$ is hydrogen, and $R^4$ is methyl,
(25) $R^1$ and $R^2$, together with the carbon to which they are attached, are joined to form a cyclopentane ring, $R^3$ is hydrogen, and $R^4$ is methyl,
(26) $R^1$ and $R^2$, together with the carbon to which they are attached, are joined to form a cyclohexane ring, $R^3$ is hydrogen, and $R^4$ is methyl,
(27) $R^1$ and $R^2$, together with the carbon to which they are attached, are joined to form a cyclopropane ring, and $R^3$ and $R^4$ are methyl,
(28) $R^1$ and $R^2$, together with the carbon to which they are attached, are joined to form a cyclobutane ring, and $R^3$ and $R^4$ are methyl,
(29) $R^1$ and $R^2$, together with the carbon to which they are attached, are joined to form a cyclopentane ring, and $R^3$ and $R^4$ are methyl,
or
(30) $R^1$ and $R^2$, together with the carbon to which they are attached, are joined to form a cyclohexane ring, and $R^3$ and $R^4$ are methyl.

18. A compound according to claim 17, which is:

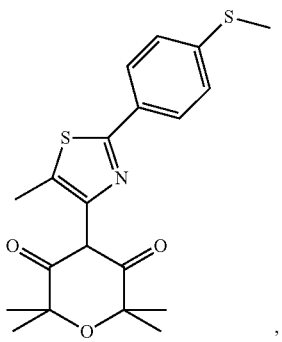

-continued

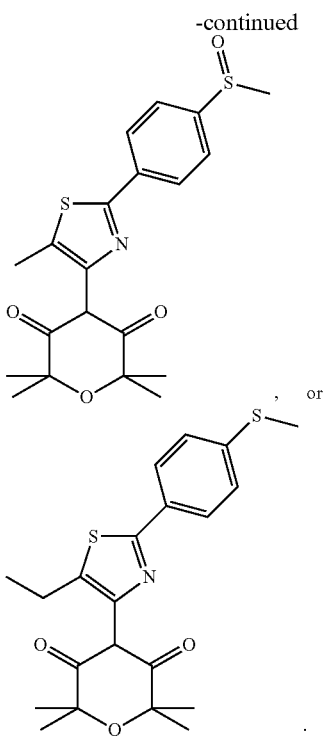

, or

19. A compound of the structural type T-2:

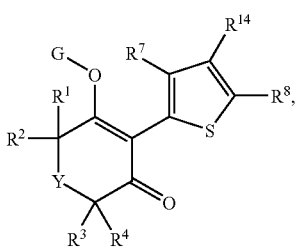

T-2 wherein $R^7$, $R^8$ and $R^{14}$ are as defined in one of Compound Types 001 to 126 below:

| Compound Types | $R^7$ | $R^8$ | $R^{14}$ |
|---|---|---|---|
| 001 | $CH_3$ | H | H |
| 002 | $CH_3$ | H | $CH_3$ |
| 003 | $CH_3$ | $CH_3$ | H |
| 004 | $CH_3$ | $CH_3$ | $CH_3$ |
| 005 | $CH_3$ | $CH_3CH_2$ | $CH_3$ |
| 006 | $CH_3CH_2$ | H | H |
| 007 | $CH_3CH_2$ | H | $CH_3$ |
| 008 | $CH_3CH_2$ | $CH_3$ | H |
| 009 | $CH_3CH_2$ | $CH_3$ | $CH_3$ |
| 010 | $CH_3CH_2$ | H | $CH_3CH_2$ |
| 011 | $CH_3CH_2$ | $CH_3$ | $CH_3CH_2$ |
| 012 | $CH_3CH_2$ | $CH_3CH_2$ | H |
| 013 | $CH_3CH_2$ | $CH_3CH_2$ | $CH_3$ |
| 014 | $CH_3CH_2$ | $CH_3CH_2$ | $CH_3CH_2$ |
| 015 | $CH_3$ | phenyl | H |
| 016 | $CH_3$ | 2-fluorophenyl | H |
| 017 | $CH_3$ | 3-fluorophenyl | H |
| 018 | $CH_3$ | 4-fluorophenyl | H |
| 019 | $CH_3$ | 2-chlorophenyl | H |
| 020 | $CH_3$ | 3-chlorophenyl | H |
| 021 | $CH_3$ | 4-chlorophenyl | H |
| 022 | $CH_3$ | 2-bromophenyl | H |
| 023 | $CH_3$ | 3-bromophenyl | H |
| 024 | $CH_3$ | 4-bromophenyl | H |
| 025 | $CH_3$ | 2-methylphenyl | H |
| 026 | $CH_3$ | 3-methylphenyl | H |
| 027 | $CH_3$ | 4-methylphenyl | H |
| 028 | $CH_3$ | 2-cyanophenyl | H |
| 029 | $CH_3$ | 3-cyanophenyl | H |
| 030 | $CH_3$ | 4-cyanophenyl | H |
| 031 | $CH_3$ | 2-methoxyphenyl | H |
| 032 | $CH_3$ | 3-methoxyphenyl | H |
| 033 | $CH_3$ | 4-methoxyphenyl | H |
| 034 | $CH_3$ | 2-trifluoromethylphenyl | H |
| 035 | $CH_3$ | 3-trifluoromethylphenyl | H |
| 036 | $CH_3$ | 4-trifluoromethylphenyl | H |
| 037 | $CH_3$ | 4-trifluoromethoxyphenyl | H |
| 038 | $CH_3$ | 4-difluoromethoxyphenyl | H |
| 039 | $CH_3$ | 4-methylthiophenyl | H |
| 040 | $CH_3$ | 4-methylsulfinylphenyl | H |
| 041 | $CH_3$ | 4-methylsulfonylphenyl | H |
| 042 | $CH_3$ | 4-trifluoromethylthiophenyl | H |
| 043 | $CH_3$ | 4-trifluoromethylsulfinylphenyl | H |
| 044 | $CH_3$ | 4-trifluoromethylsulfonylphenyl | H |
| 045 | $CH_3$ | 2,3-difluorophenyl | H |
| 046 | $CH_3$ | 2,4-difluorophenyl | H |
| 047 | $CH_3$ | 2,5-difluorophenyl | H |
| 048 | $CH_3$ | 2,6-difluorophenyl | H |
| 049 | $CH_3$ | 3,4-difluorophenyl | H |
| 050 | $CH_3$ | 3,5-difluorophenyl | H |
| 051 | $CH_3$ | 2,3-dichlorophenyl | H |
| 052 | $CH_3$ | 2,4-dichlorophenyl | H |
| 053 | $CH_3$ | 2,5-dichlorophenyl | H |
| 054 | $CH_3$ | 2,6-dichlorophenyl | H |
| 055 | $CH_3$ | 3,4-dichlorophenyl | H |
| 056 | $CH_3$ | 3,5-dichlorophenyl | H |
| 057 | $CH_3$ | 4-chloro-2-fluorophenyl | H |
| 058 | $CH_3$ | 4-chloro-3-fluorophenyl | H |
| 059 | $CH_3$ | 4-chloro-2-methylphenyl | H |
| 060 | $CH_3$ | 4-chloro-3-methylphenyl | H |
| 061 | $CH_3$ | 2-fluoro-4-trifluoromethylphenyl | H |
| 062 | $CH_3$ | 3-fluoro-4-trifluoromethylphenyl | H |
| 063 | $CH_3$ | 2-chloropyridin-5-yl | H |
| 064 | $CH_3$ | 3-chloropyridinyl-5-yl | H |
| 065 | $CH_3$ | 2-methylpyridin-5-yl | H |
| 066 | $CH_3$ | 3-methylpyridinyl-5-yl | H |
| 067 | $CH_3$ | 2-trifluoromethylpyridin-5-yl | H |
| 068 | $CH_3$ | 3-trifluoromethylpyridin-5-yl | H |
| 069 | $CH_3$ | 2,6-dichloropyridin-3-yl | H |
| 070 | $CH_3$ | 4-chloropyrazol-1-yl | H |
| 071 | $CH_3CH_2$ | phenyl | H |
| 072 | $CH_3CH_2$ | 2-fluorophenyl | H |
| 073 | $CH_3CH_2$ | 3-fluorophenyl | H |
| 074 | $CH_3CH_2$ | 4-fluorophenyl | H |
| 075 | $CH_3CH_2$ | 2-chlorophenyl | H |
| 076 | $CH_3CH_2$ | 3-chlorophenyl | H |
| 077 | $CH_3CH_2$ | 4-chlorophenyl | H |
| 078 | $CH_3CH_2$ | 2-bromophenyl | H |
| 079 | $CH_3CH_2$ | 3-bromophenyl | H |
| 080 | $CH_3CH_2$ | 4-bromophenyl | H |
| 081 | $CH_3CH_2$ | 2-methylphenyl | H |
| 082 | $CH_3CH_2$ | 3-methylphenyl | H |
| 083 | $CH_3CH_2$ | 4-methylphenyl | H |
| 084 | $CH_3CH_2$ | 2-cyanophenyl | H |
| 085 | $CH_3CH_2$ | 3-cyanophenyl | H |
| 086 | $CH_3CH_2$ | 4-cyanophenyl | H |
| 087 | $CH_3CH_2$ | 2-methoxyphenyl | H |
| 088 | $CH_3CH_2$ | 3-methoxyphenyl | H |
| 089 | $CH_3CH_2$ | 4-methoxyphenyl | H |
| 090 | $CH_3CH_2$ | 2-trifluoromethylphenyl | H |
| 091 | $CH_3CH_2$ | 3-trifluoromethylphenyl | H |
| 092 | $CH_3CH_2$ | 4-trifluoromethylphenyl | H |
| 093 | $CH_3CH_2$ | 4-trifluoromethoxyphenyl | H |
| 094 | $CH_3CH_2$ | 4-difluoromethoxyphenyl | H |
| 095 | $CH_3CH_2$ | 4-methylthiophenyl | H |
| 096 | $CH_3CH_2$ | 4-methylsulfinylphenyl | H |

-continued

| Compound Types | $R^7$ | $R^8$ | $R^{14}$ |
|---|---|---|---|
| 097 | $CH_3CH_2$ | 4-methylsulfonylphenyl | H |
| 098 | $CH_3CH_2$ | 4-trifluoromethylthiophenyl | H |
| 099 | $CH_3CH_2$ | 4-trifluoromethylsulfinylphenyl | H |
| 100 | $CH_3CH_2$ | 4-trifluoromethylsulfonylphenyl | H |
| 101 | $CH_3CH_2$ | 2,3-difluorophenyl | H |
| 102 | $CH_3CH_2$ | 2,4-difluorophenyl | H |
| 103 | $CH_3CH_2$ | 2,5-difluorophenyl | H |
| 104 | $CH_3CH_2$ | 2,6-difluorophenyl | H |
| 105 | $CH_3CH_2$ | 3,4-difluorophenyl | H |
| 106 | $CH_3CH_2$ | 3,5-difluorophenyl | H |
| 107 | $CH_3CH_2$ | 2,3-dichlorophenyl | H |
| 108 | $CH_3CH_2$ | 2,4-dichlorophenyl | H |
| 109 | $CH_3CH_2$ | 2,5-dichlorophenyl | H |
| 110 | $CH_3CH_2$ | 2,6-dichlorophenyl | H |
| 111 | $CH_3CH_2$ | 3,4-dichlorophenyl | H |
| 112 | $CH_3CH_2$ | 3,5-dichlorophenyl | H |
| 113 | $CH_3CH_2$ | 4-chloro-2-fluorophenyl | H |
| 114 | $CH_3CH_2$ | 4-chloro-3-fluorophenyl | H |
| 115 | $CH_3CH_2$ | 4-chloro-2-methylphenyl | H |
| 116 | $CH_3CH_2$ | 4-chloro-3-methylphenyl | H |
| 117 | $CH_3CH_2$ | 2-fluoro-4-trifluoromethylphenyl | H |
| 118 | $CH_3CH_2$ | 3-fluoro-4-trifluoromethylphenyl | H |
| 119 | $CH_3CH_2$ | 2-chloropyridin-5-yl | H |
| 120 | $CH_3CH_2$ | 3-chloropyridinyl-5-yl | H |
| 121 | $CH_3CH_2$ | 2-methylpyridin-5-yl | H |
| 122 | $CH_3CH_2$ | 3-methylpyridinyl-5-yl | H |
| 123 | $CH_3CH_2$ | 2-trifluoromethylpyridin-5-yl | H |
| 124 | $CH_3CH_2$ | 3-trifluoromethylpyridin-5-yl | H |
| 125 | $CH_3CH_2$ | 2,6-dichloropyridin-3-yl | H |
| 126 | $CH_3CH_2$ | 4-chloropyrazol-1-yl | H | and wherein:
Y is O;
G is hydrogen; and
(1) $R^1$, $R^2$, $R^3$ and $R^4$ are hydrogen,
(2) $R^1$ is methyl, and $R^2$, $R^3$ and $R^4$ are hydrogen,
(3) $R^1$ and $R^2$ are methyl, and $R^3$ and $R^4$ are hydrogen,
(4) $R^1$ and $R^3$ are methyl, and $R^2$ and $R^4$ are hydrogen,
(5) $R^1$, $R^2$, and $R^3$ are methyl, and $R^4$ is hydrogen,
(6) $R^1$, $R^2$, $R^3$ and $R^4$ are methyl,
(7) $R^1$ is ethyl, and $R^2$, $R^3$ and $R^4$ are hydrogen,
(8) $R^1$ is ethyl, $R^2$ is methyl, and $R^3$ and $R^4$ are hydrogen,
(9) $R^1$ is ethyl, $R^2$ and $R^3$ are hydrogen, and $R^4$ is methyl,
(10) $R^1$ is ethyl, $R^2$ and $R^3$ are methyl, and $R^4$ is hydrogen,
(11) $R^1$ is ethyl, $R^2$ is hydrogen, and $R^3$ and $R^4$ are methyl,
(12) $R^1$ is ethyl, and $R^2$, $R^3$ and $R^4$ are methyl,
(13) $R^1$ and $R^2$ are ethyl, and $R^3$ and $R^4$ are methyl,
(14) $R^1$ and $R^3$ are ethyl, and $R^2$ and $R^4$ are methyl,
(15) $R^1$ and $R^2$ are ethyl, and $R^3$ and $R^4$ are hydrogen,
(16) $R^1$ and $R^3$ are ethyl, and $R^2$ and $R^4$ are hydrogen,
(17) $R^1$ and $R^3$ are ethyl, $R^2$ is methyl, and $R^4$ is hydrogen,
(18) $R^1$ and $R^3$ are ethyl, and $R^2$ and $R^4$ are methyl,
(19) $R^1$ and $R^2$, together with the carbon to which they are attached, are joined to form a cyclopropane ring, and $R^3$ and $R^4$ are hydrogen,
(20) $R^1$ and $R^2$, together with the carbon to which they are attached, are joined to form a cyclobutane ring, and $R^3$ and $R^4$ are hydrogen,
(21) $R^1$ and $R^2$, together with the carbon to which they are attached, are joined to form a cyclopentane ring, and $R^3$ and $R^4$ are hydrogen,
(22) $R^1$ and $R^2$, together with the carbon to which they are attached, are joined to form a cyclohexane ring, and $R^3$ and $R^4$ are hydrogen,
(23) $R^1$ and $R^2$, together with the carbon to which they are attached, are joined to form a cyclopropane ring, $R^3$ is hydrogen, and $R^4$ is methyl,
(24) $R^1$ and $R^2$, together with the carbon to which they are attached, are joined to form a cyclobutane ring, $R^3$ is hydrogen, and $R^4$ is methyl,
(25) $R^1$ and $R^2$, together with the carbon to which they are attached, are joined to form a cyclopentane ring, $R^3$ is hydrogen, and $R^4$ is methyl,
(26) $R^1$ and $R^2$, together with the carbon to which they are attached, are joined to form a cyclohexane ring, $R^3$ is hydrogen, and $R^4$ is methyl,
(27) $R^1$ and $R^2$, together with the carbon to which they are attached, are joined to form a cyclopropane ring, and $R^3$ and $R^4$ are methyl,
(28) $R^1$ and $R^2$, together with the carbon to which they are attached, are joined to form a cyclobutane ring, and $R^3$ and $R^4$ are methyl,
(29) $R^1$ and $R^2$, together with the carbon to which they are attached, are joined to form a cyclopentane ring, and $R^3$ and $R^4$ are methyl, or
(30) $R^1$ and $R^2$, together with the carbon to which they are attached, are joined to form a cyclohexane ring, and $R^3$ and $R^4$ are methyl.

20. A compound of the structural type T-4:

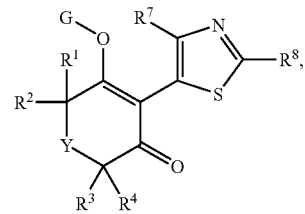

T-4 wherein $R^7$ and $R^8$ are as defined in one of Compound Types 289.001 to 289.118 below:

| Compound Type | $R^7$ | $R^8$ |
|---|---|---|
| 289.001 | $CH_3$ | H |
| 289.002 | $CH_3$ | $CH_3$ |
| 289.003 | $CH_3$ | $CH_3CH_2$ |
| 289.004 | $CH_3CH_2$ | H |
| 289.005 | $CH_3CH_2$ | $CH_3$ |
| 289.006 | $CH_3CH_2$ | $CH_3CH_2$ |
| 289.007 | $CH_3$ | phenyl |
| 289.008 | $CH_3$ | 2-fluorophenyl |
| 289.009 | $CH_3$ | 3-fluorophenyl |
| 289.010 | $CH_3$ | 4-fluorophenyl |
| 289.011 | $CH_3$ | 2-chlorophenyl |
| 289.012 | $CH_3$ | 3-chlorophenyl |
| 289.013 | $CH_3$ | 4-chlorophenyl |
| 289.014 | $CH_3$ | 2-bromophenyl |
| 289.015 | $CH_3$ | 3-bromophenyl |
| 289.016 | $CH_3$ | 4-bromophenyl |
| 289.017 | $CH_3$ | 2-methylphenyl |
| 289.018 | $CH_3$ | 3-methylphenyl |
| 289.019 | $CH_3$ | 4-methylphenyl |
| 289.020 | $CH_3$ | 2-cyanophenyl |
| 289.021 | $CH_3$ | 3-cyanophenyl |
| 289.022 | $CH_3$ | 4-cyanophenyl |
| 289.023 | $CH_3$ | 2-methoxyphenyl |
| 289.024 | $CH_3$ | 3-methoxyphenyl |
| 289.025 | $CH_3$ | 4-methoxyphenyl |
| 289.026 | $CH_3$ | 2-trifluoromethylphenyl |
| 289.027 | $CH_3$ | 3-trifluoromethylphenyl |
| 289.028 | $CH_3$ | 4-trifluoromethylphenyl |
| 289.029 | $CH_3$ | 4-trifluoromethoxyphenyl |
| 289.030 | $CH_3$ | 4-difluoromethoxyphenyl |
| 289.031 | $CH_3$ | 4-methylthiophenyl |
| 289.032 | $CH_3$ | 4-methylsulfinylphenyl |

| Compound Type | R⁷ | R⁸ |
|---|---|---|
| 289.033 | CH₃ | 4-methylsulfonylphenyl |
| 289.034 | CH₃ | 4-trifluoromethylthiophenyl |
| 289.035 | CH₃ | 4-trifluoromethylsulfinylphenyl |
| 289.036 | CH₃ | 4-trifluoromethylsulfonylphenyl |
| 289.037 | CH₃ | 2,3-difluorophenyl |
| 289.038 | CH₃ | 2,4-difluorophenyl |
| 289.039 | CH₃ | 2,5-difluorophenyl |
| 289.040 | CH₃ | 2,6-difluorophenyl |
| 289.041 | CH₃ | 3,4-difluorophenyl |
| 289.042 | CH₃ | 3,5-difluorophenyl |
| 289.043 | CH₃ | 2,3-dichlorophenyl |
| 289.044 | CH₃ | 2,4-dichlorophenyl |
| 289.045 | CH₃ | 2,5-dichlorophenyl |
| 289.046 | CH₃ | 2,6-dichlorophenyl |
| 289.047 | CH₃ | 3,4-dichlorophenyl |
| 289.048 | CH₃ | 3,5-dichlorophenyl |
| 289.049 | CH₃ | 4-chloro-2-fluorophenyl |
| 289.050 | CH₃ | 4-chloro-3-fluorophenyl |
| 289.051 | CH₃ | 4-chloro-2-methylphenyl |
| 289.052 | CH₃ | 4-chloro-3-methylphenyl |
| 289.053 | CH₃ | 2-fluoro-4-trifluoromethylphenyl |
| 289.054 | CH₃ | 3-fluoro-4-trifluoromethylphenyl |
| 289.055 | CH₃ | 2-chloropyridin-5-yl |
| 289.056 | CH₃ | 3-chloropyridinyl-5-yl |
| 289.057 | CH₃ | 2-methylpyridin-5-yl |
| 289.058 | CH₃ | 3-methylpyridinyl-5-yl |
| 289.059 | CH₃ | 2-trifluoromethylpyridin-5-yl |
| 289.060 | CH₃ | 3-trifluoromethylpyridin-5-yl |
| 289.061 | CH₃ | 2,6-dichloropyridin-3-yl |
| 289.062 | CH₃ | 4-chloropyrazol-1-yl |
| 289.063 | CH₃CH₂ | phenyl |
| 289.064 | CH₃CH₂ | 2-fluorophenyl |
| 289.065 | CH₃CH₂ | 3-fluorophenyl |
| 289.066 | CH₃CH₂ | 4-fluorophenyl |
| 289.067 | CH₃CH₂ | 2-chlorophenyl |
| 289.068 | CH₃CH₂ | 3-chlorophenyl |
| 289.069 | CH₃CH₂ | 4-chlorophenyl |
| 289.070 | CH₃CH₂ | 2-bromophenyl |
| 289.071 | CH₃CH₂ | 3-bromophenyl |
| 289.072 | CH₃CH₂ | 4-bromophenyl |
| 289.073 | CH₃CH₂ | 2-methylphenyl |
| 289.074 | CH₃CH₂ | 3-methylphenyl |
| 289.075 | CH₃CH₂ | 4-methylphenyl |
| 289.076 | CH₃CH₂ | 2-cyanophenyl |
| 289.077 | CH₃CH₂ | 3-cyanophenyl |
| 289.078 | CH₃CH₂ | 4-cyanophenyl |
| 289.079 | CH₃CH₂ | 2-methoxyphenyl |
| 289.080 | CH₃CH₂ | 3-methoxyphenyl |
| 289.081 | CH₃CH₂ | 4-methoxyphenyl |
| 289.082 | CH₃CH₂ | 2-trifluoromethylphenyl |
| 289.083 | CH₃CH₂ | 3-trifluoromethylphenyl |
| 289.084 | CH₃CH₂ | 4-trifluoromethylphenyl |
| 289.085 | CH₃CH₂ | 4-trifluoromethoxyphenyl |
| 289.086 | CH₃CH₂ | 4-difluoromethoxyphenyl |
| 289.087 | CH₃CH₂ | 4-methylthiophenyl |
| 289.088 | CH₃CH₂ | 4-methylsulfinylphenyl |
| 289.089 | CH₃CH₂ | 4-methylsulfonylphenyl |
| 289.090 | CH₃CH₂ | 4-trifluoromethylthiophenyl |
| 289.091 | CH₃CH₂ | 4-trifluoromethylsulfinylphenyl |
| 289.092 | CH₃CH₂ | 4-trifluoromethylsulfonylphenyl |
| 289.093 | CH₃CH₂ | 2,3-difluorophenyl |
| 289.094 | CH₃CH₂ | 2,4-difluorophenyl |
| 289.095 | CH₃CH₂ | 2,5-difluorophenyl |
| 289.096 | CH₃CH₂ | 2,6-difluorophenyl |
| 289.097 | CH₃CH₂ | 3,4-difluorophenyl |
| 289.098 | CH₃CH₂ | 3,5-difluorophenyl |
| 289.099 | CH₃CH₂ | 2,3-dichlorophenyl |
| 289.100 | CH₃CH₂ | 2,4-dichlorophenyl |
| 289.101 | CH₃CH₂ | 2,5-dichlorophenyl |
| 289.102 | CH₃CH₂ | 2,6-dichlorophenyl |
| 289.103 | CH₃CH₂ | 3,4-dichlorophenyl |
| 289.104 | CH₃CH₂ | 3,5-dichlorophenyl |
| 289.105 | CH₃CH₂ | 4-chloro-2-fluorophenyl |
| 289.106 | CH₃CH₂ | 4-chloro-3-fluorophenyl |
| 289.107 | CH₃CH₂ | 4-chloro-2-methylphenyl |
| 289.108 | CH₃CH₂ | 4-chloro-3-methylphenyl |
| 289.109 | CH₃CH₂ | 2-fluoro-4-trifluoromethylphenyl |
| 289.110 | CH₃CH₂ | 3-fluoro-4-trifluoromethylphenyl |
| 289.111 | CH₃CH₂ | 2-chloropyridin-5-yl |
| 289.112 | CH₃CH₂ | 3-chloropyridinyl-5-yl |
| 289.113 | CH₃CH₂ | 2-methylpyridin-5-yl |
| 289.114 | CH₃CH₂ | 3-methylpyridinyl-5-yl |
| 289.115 | CH₃CH₂ | 2-trifluoromethylpyridin-5-yl |
| 289.116 | CH₃CH₂ | 3-trifluoromethylpyridin-5-yl |
| 289.117 | CH₃CH₂ | 2,6-dichloropyridin-3-yl |
| 289.118 | CH₃CH₂ | 4-chloropyrazol-1-yl | and wherein:

Y is O;

G is hydrogen; and (1) $R^1$, $R^2$, $R^3$ and $R^4$ are hydrogen,
(2) $R^1$ is methyl, and $R^2$, $R^3$ and $R^4$ are hydrogen,
(3) $R^1$ and $R^2$ are methyl, and $R^3$ and $R^4$ are hydrogen,
(4) $R^1$ and $R^3$ are methyl, and $R^2$ and $R^4$ are hydrogen,
(5) $R^1$, $R^2$, and $R^3$ are methyl, and $R^4$ is hydrogen,
(6) $R^1$, $R^2$, $R^3$ and $R^4$ are methyl,
(7) $R^1$ is ethyl, and $R^2$, $R^3$ and $R^4$ are hydrogen,
(8) $R^1$ is ethyl, $R^2$ is methyl, and $R^3$ and $R^4$ are hydrogen,
(9) $R^1$ is ethyl, $R^2$ and $R^3$ are hydrogen, and $R^4$ is methyl,
(10) $R^1$ is ethyl, $R^2$ and $R^3$ are methyl, and $R^4$ is hydrogen,
(11) $R^1$ is ethyl, $R^2$ is hydrogen, and $R^3$ and $R^4$ are methyl,
(12) $R^1$ is ethyl, and $R^2$, $R^3$ and $R^4$ are methyl,
(13) $R^1$ and $R^2$ are ethyl, and $R^3$ and $R^4$ are methyl,
(14) $R^1$ and $R^3$ are ethyl, and $R^2$ and $R^4$ are methyl,
(15) $R^1$ and $R^2$ are ethyl, and $R^3$ and $R^4$ are hydrogen,
(16) $R^1$ and $R^3$ are ethyl, and $R^2$ and $R^4$ are hydrogen,
(17) $R^1$ and $R^3$ are ethyl, $R^2$ is methyl, and $R^4$ is hydrogen,
(18) $R^1$ and $R^3$ are ethyl, and $R^2$ and $R^4$ are methyl,
(19) $R^1$ and $R^2$, together with the carbon to which they are attached, are joined to form a cyclopropane ring, and $R^3$ and $R^4$ are hydrogen,
(20) $R^1$ and $R^2$, together with the carbon to which they are attached, are joined to form a cyclobutane ring, and $R^3$ and $R^4$ are hydrogen,
(21) $R^1$ and $R^2$, together with the carbon to which they are attached, are joined to form a cyclopentane ring, and $R^3$ and $R^4$ are hydrogen,
(22) $R^1$ and $R^2$, together with the carbon to which they are attached, are joined to form a cyclohexane ring, and $R^3$ and $R^4$ are hydrogen,
(23) $R^1$ and $R^2$, together with the carbon to which they are attached, are joined to form a cyclopropane ring, $R^3$ is hydrogen, and $R^4$ is methyl,
(24) $R^1$ and $R^2$, together with the carbon to which they are attached, are joined to form a cyclobutane ring, $R^3$ is hydrogen, and $R^4$ is methyl,
(25) $R^1$ and $R^2$, together with the carbon to which they are attached, are joined to form a cyclopentane ring, $R^3$ is hydrogen, and $R^4$ is methyl,
(26) $R^1$ and $R^2$, together with the carbon to which they are attached, are joined to form a cyclohexane ring, $R^3$ is hydrogen, and $R^4$ is methyl,
(27) $R^1$ and $R^2$, together with the carbon to which they are attached, are joined to form a cyclopropane ring, and $R^3$ and $R^4$ are methyl,
(28) $R^1$ and $R^2$, together with the carbon to which they are attached, are joined to form a cyclobutane ring, and $R^3$ and $R^4$ are methyl,

(29) $R^1$ and $R^2$, together with the carbon to which they are attached, are joined to form a cyclopentane ring, and $R^3$ and $R^4$ are methyl, or

(30) $R^1$ and $R^2$, together with the carbon to which they are attached, are joined to form a cyclohexane ring, and $R^3$ and $R^4$ are methyl.

21. A compound of the structure:

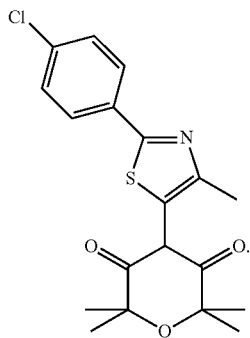 [SMILES: Cc1nc(-c2ccc(Cl)cc2)sc1C1C(=O)C(C)(C)OC(C)(C)C1=O]

22. A compound of the structure:

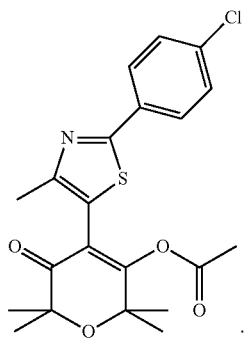 [SMILES: CC(=O)OC1=C(c2sc(-c3ccc(Cl)cc3)nc2C)C(=O)C(C)(C)OC1(C)C]

23. A compound of the structure:

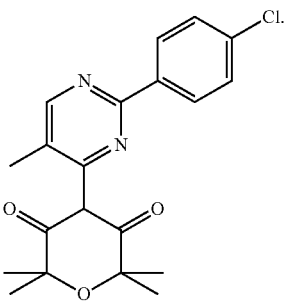 [SMILES: Cc1cnc(-c2ccc(Cl)cc2)nc1C1C(=O)C(C)(C)OC(C)(C)C1=O]

24. A compound according to claim 1, wherein $R^8$ is halogen, methyl, ethyl, methyl substituted by halogen, ethyl substituted by halogen, vinyl, methoxy, ethoxy, methoxy substituted by halogen, or ethoxy substituted by halogen;

or $R^8$ is thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl, or pyridazinyl, or a salt thereof, each of these being unsubstituted or substituted by halogen, methyl, ethyl, halo$C_1$alkyl, methoxy, ethoxy or halo$C_1$alkoxy.

25. A compound according to claim 24, wherein:

$R^1$, $R^2$, $R^3$ and $R^4$, independently of each other, are hydrogen, methyl or ethyl; and Het is selected from the groups of the formulae $R_2$ to $R_{10}$ and $R_{24}$, and Het is a substituted monocyclic 5-membered nitrogen or sulfur containing heteroaryl.

* * * * *